(12) United States Patent
Carter et al.

(10) Patent No.: US 7,872,113 B2
(45) Date of Patent: Jan. 18, 2011

(54) NUCLEIC ACIDS ENCODING ANTIBODIES THAT BIND INTERLEUKIN-4 RECEPTOR

(75) Inventors: Paul J. Carter, Mercer Island, WA (US); Hongxing Zhou, Bellevue, WA (US)

(73) Assignee: Immunex Corporation, Thousand Oaks, CA (US)

( * ) Notice: Subject to any disclaimer, the term of this patent is extended or adjusted under 35 U.S.C. 154(b) by 0 days.

(21) Appl. No.: 12/535,648

(22) Filed: Aug. 4, 2009

(65) Prior Publication Data

US 2010/0203590 A1    Aug. 12, 2010

Related U.S. Application Data

(62) Division of application No. 10/578,410, filed as application No. PCT/US2004/037242 on Nov. 4, 2004, now Pat. No. 7,638,606.

(60) Provisional application No. 60/518,166, filed on Nov. 7, 2003.

(51) Int. Cl.
C07H 21/04     (2006.01)
(52) U.S. Cl. .................... 536/23.53; 536/24.3
(58) Field of Classification Search .............. None
See application file for complete search history.

(56) References Cited

U.S. PATENT DOCUMENTS 5,717,072 A    2/1998    Mosley et al.
6,716,587 B2   4/2004    Mosley et al.

FOREIGN PATENT DOCUMENTS

| EP | 0 604 693 | 7/1994 |
| WO | WO 90/05183 | 5/1990 |
| WO | WO 91/09059 | 6/1991 |
| WO | WO 94/21282 | 9/1994 |
| WO | WO 96/33735 | 10/1996 |
| WO | WO 96/34096 | 10/1996 |
| WO | WO 00/18932 | 4/2000 |
| WO | WO 01/92340 | 12/2001 |

OTHER PUBLICATIONS

Hultgren O., et al., "*Staphylococcus aureus*-induced septic arthritis and septic death is decreased in IL-4-deficient mice: role of IL-4 as promoter for bacterial growth." *J. Immunol* 1998:1605082-5087, May 1998.
Wills-Karp., et al., "Interleukin-13: Central Mediator of Allergic Asthma." *Science* 282:2258-2261, Dec. 1998.
Holt LJ, et al., "Domain antibodies: proteins for therapy," *Trends in Biotech*, 21(11):484-490, Nov. 2003.
Zurawski SM, et al., "The primary binding subunit of the human interleukin-4 receptor is also a component of the interleukin-13 receptor," *J. Biol Chem* 270(23):13869-13878, Jun. 9, 1995.
Database EPOP: Accession No. AX356126, Jun. 13, 2005.
Related International Search Report for PCT/US01/17094.

*Primary Examiner*—Zachary Skelding
(74) *Attorney, Agent, or Firm*—Nathan A. Machin

(57) ABSTRACT

The present invention relates to antibodies that bind to the IL-4 receptor, fragments, muteins, and derivatives of such antibodies, nucleic acids encoding such antibodies, fragments, muteins and derivatives, and methods of making and using such antibodies, fragments, muteins, derivatives and nucleic acids. Methods for treating medical conditions induced by interleukin-4 involve administering an IL-4 receptor binding antibody, or an IL-4 receptor binding fragment, mutein, or derivative of an IL-4 receptor binding antibody, to a patient afflicted with such a condition. Particular antibodies provided herein include human monoclonal antibodies. Certain of the antibodies inhibit both IL-4-induced and IL-13-induced biological activities.

12 Claims, 8 Drawing Sheets

FIGURE 1A

```
ATG GGG TGG CTT TGC TCT GGG CTC CTG TTC CCT GTG AGC TGC CTG  -31
Met Gly Trp Leu Cys Ser Gly Leu Leu Phe Pro Val Ser Cys Leu  -11

GTC CTG CTG CAG GTG GCA AGC TCT GGG AAC ATG AAG GTC TTG CAG   15
Val Leu Leu Gln Val Ala Ser Ser Gly Asn Met Lys Val Leu Gln    5

GAG CCC ACC TGC GTC TCC GAC TAC ATG AGC ATC TCT ACT TGC GAG   60
Glu Pro Thr Cys Val Ser Asp Tyr Met Ser Ile Ser Thr Cys Glu   20

TGG AAG ATG AAT GGT CCC ACC AAT TGC AGC ACC GAG CTC CGC CTG  105
Trp Lys Met Asn Gly Pro Thr Asn Cys Ser Thr Glu Leu Arg Leu   35

TTG TAC CAG CTG GTT TTT CTG CTC TCC GAA GCC CAC ACG TGT ATC  150
Leu Tyr Gln Leu Val Phe Leu Leu Ser Glu Ala His Thr Cys Ile   50

CCT GAG AAC AAC GGA GGC GCG GGG TGC GTG TGC CAC CTG CTC ATG  195
Pro Glu Asn Asn Gly Gly Ala Gly Cys Val Cys His Leu Leu Met   65

GAT GAC GTG GTC AGT GCG GAT AAC TAT ACA CTG GAC CTG TGG GCT  240
Asp Asp Val Val Ser Ala Asp Asn Tyr Thr Leu Asp Leu Trp Ala   80

GGG CAG CAG CTG CTG TGG AAG GGC TCC TTC AAG CCC AGC GAG CAT  285
Gly Gln Gln Leu Leu Trp Lys Gly Ser Phe Lys Pro Ser Glu His   95

GTG AAA CCC AGG GCC CCA GGA AAC CTG ACA GTT CAC ACC AAT GTC  330
Val Lys Pro Arg Ala Pro Gly Asn Leu Thr Val His Thr Asn Val  110

TCC GAC ACT CTG CTG CTG ACC TGG AGC AAC CCG TAT CCC CCT GAC  375
Ser Asp Thr Leu Leu Leu Thr Trp Ser Asn Pro Tyr Pro Pro Asp  125

AAT TAC CTG TAT AAT CAT CTC ACC TAT GCA GTC AAC ATT TGG AGT  420
Asn Tyr Leu Tyr Asn His Leu Thr Tyr Ala Val Asn Ile Trp Ser  140

GAA AAC GAC CCG GCA GAT TTC AGA ATC TAT AAC GTG ACC TAC CTA  465
Glu Asn Asp Pro Ala Asp Phe Arg Ile Tyr Asn Val Thr Tyr Leu  155

GAA CCC TCC CTC CGC ATC GCA GCC AGC ACC CTG AAG TCT GGG ATT  510
Glu Pro Ser Leu Arg Ile Ala Ala Ser Thr Leu Lys Ser Gly Ile  170

TCC TAC AGG GCA CGG GTG AGG GCC TGG GCT CAG TGC TAT AAC ACC  555
Ser Tyr Arg Ala Arg Val Arg Ala Trp Ala Gln Cys Tyr Asn Thr  185

ACC TGG AGT GAG TGG AGC CCC AGC ACC AAG TGG CAC AAC TCC TAC  600
Thr Trp Ser Glu Trp Ser Pro Ser Thr Lys Trp His Asn Ser Tyr  200

AGG GAG CCC TTC GAG CAG CAC CTC CTG CTG GGC GTC AGC GTT TCC  645
Arg Glu Pro Phe Glu Gln His Leu Leu Leu Gly Val Ser Val Ser  215

TGC ATT GTC ATC CTG GCC GTC TGC CTG TTG TGC TAT GTC AGC ATC  690
Cys Ile Val Ile Leu Ala Val Cys Leu Leu Cys Tyr Val Ser Ile  230

ACC AAG ATT AAG AAA GAA TGG TGG GAT CAG ATT CCC AAC CCA GCC  735
Thr Lys Ile Lys Lys Glu Trp Trp Asp Gln Ile Pro Asn Pro Ala  245
```

FIGURE 1B

```
CGC AGC CGC CTC GTG GCT ATA ATA ATC CAG GAT GCT CAG GGG TCA  780
Arg Ser Arg Leu Val Ala Ile Ile Ile Gln Asp Ala Gln Gly Ser  260

CAG TGG GAG AAG CGG TCC CGA GGC CAG GAA CCA GCC AAG TGC CCA  825
Gln Trp Glu Lys Arg Ser Arg Gly Gln Glu Pro Ala Lys Cys Pro  275

CAC TGG AAG AAT TGT CTT ACC AAG CTC TTG CCC TGT TTT CTG GAG  870
His Trp Lys Asn Cys Leu Thr Lys Leu Leu Pro Cys Phe Leu Glu  290

CAC AAC ATG AAA AGG GAT GAA GAT CCT CAC AAG GCT GCC AAA GAG  915
His Asn Met Lys Arg Asp Glu Asp Pro His Lys Ala Ala Lys Glu  305

ATG CCT TTC CAG GGC TCT GGA AAA TCA GCA TGG TGC CCA GTG GAG  960
Met Pro Phe Gln Gly Ser Gly Lys Ser Ala Trp Cys Pro Val Glu  320

ATC AGC AAG ACA GTC CTC TGG CCA GAG AGC ATC AGC GTG GTG CGA 1005
Ile Ser Lys Thr Val Leu Trp Pro Glu Ser Ile Ser Val Val Arg  335

TGT GTG GAG TTG TTT GAG GCC CCG GTG GAG TGT GAG GAG GAG GAG 1050
Cys Val Glu Leu Phe Glu Ala Pro Val Glu Cys Glu Glu Glu Glu  350

GAG GTA GAG GAA GAA AAA GGG AGC TTC TGT GCA TCG CCT GAG AGC 1095
Glu Val Glu Glu Glu Lys Gly Ser Phe Cys Ala Ser Pro Glu Ser  365

AGC AGG GAT GAC TTC CAG GAG GGA AGG GAG GGC ATT GTG GCC CGG 1140
Ser Arg Asp Asp Phe Gln Glu Gly Arg Glu Gly Ile Val Ala Arg  380

CTA ACA GAG AGC CTG TTC CTG GAC CTG CTC GGA GAG GAG AAT GGG 1185
Leu Thr Glu Ser Leu Phe Leu Asp Leu Leu Gly Glu Glu Asn Gly  395

GGC TTT TGC CAG CAG GAC ATG GGG GAG TCA TGC CTT CTT CCA CCT 1230
Gly Phe Cys Gln Gln Asp Met Gly Glu Ser Cys Leu Leu Pro Pro  410

TCG GGA AGT ACG AGT GCT CAC ATG CCC TGG GAT GAG TTC CCA AGT 1275
Ser Gly Ser Thr Ser Ala His Met Pro Trp Asp Glu Phe Pro Ser  425

GCA GGG CCC AAG GAG GCA CCT CCC TGG GGC AAG GAG CAG CCT CTC 1320
Ala Gly Pro Lys Glu Ala Pro Pro Trp Gly Lys Glu Gln Pro Leu  440

CAC CTG GAG CCA AGT CCT CCT GCC AGC CCG ACC CAG AGT CCA GAC 1365
His Leu Glu Pro Ser Pro Pro Ala Ser Pro Thr Gln Ser Pro Asp  455

AAC CTG ACT TGC ACA GAG ACG CCC CTC GTC ATC GCA GGC AAC CCT 1410
Asn Leu Thr Cys Thr Glu Thr Pro Leu Val Ile Ala Gly Asn Pro  470

GCT TAC CGC AGC TTC AGC AAC TCC CTG AGC CAG TCA CCG TGT CCC 1455
Ala Tyr Arg Ser Phe Ser Asn Ser Leu Ser Gln Ser Pro Cys Pro  485

AGA GAG CTG GGT CCA GAC CCA CTG CTG GCC AGA CAC CTG GAG GAA 1500
Arg Glu Leu Gly Pro Asp Pro Leu Leu Ala Arg His Leu Glu Glu  500

GTA GAA CCC GAG ATG CCC TGT GTC CCC CAG CTC TCT GAG CCA ACC 1545
Val Glu Pro Glu Met Pro Cys Val Pro Gln Leu Ser Glu Pro Thr  515
```

FIGURE 1C

```
ACT GTG CCC CAA CCT GAG CCA GAA ACC TGG GAG CAG ATC CTC CGC  1590
Thr Val Pro Gln Pro Glu Pro Glu Thr Trp Glu Gln Ile Leu Arg   530

CGA AAT GTC CTC CAG CAT GGG GCA GCT GCA GCC CCC GTC TCG GCC  1635
Arg Asn Val Leu Gln His Gly Ala Ala Ala Ala Pro Val Ser Ala   545

CCC ACC AGT GGC TAT CAG GAG TTT GTA CAT GCG GTG GAG CAG GGT  1680
Pro Thr Ser Gly Tyr Gln Glu Phe Val His Ala Val Glu Gln Gly   560

GGC ACC CAG GCC AGT GCG GTG GTG GGC TTG GGT CCC CCA GGA GAG  1725
Gly Thr Gln Ala Ser Ala Val Val Gly Leu Gly Pro Pro Gly Glu   575

GCT GGT TAC AAG GCC TTC TCA AGC CTG CTT GCC AGC AGT GCT GTG  1770
Ala Gly Tyr Lys Ala Phe Ser Ser Leu Leu Ala Ser Ser Ala Val   590

TCC CCA GAG AAA TGT GGG TTT GGG GCT AGC AGT GGG GAA GAG GGG  1815
Ser Pro Glu Lys Cys Gly Phe Gly Ala Ser Ser Gly Glu Glu Gly   605

TAT AAG CCT TTC CAA GAC CTC ATT CCT GGC TGC CCT GGG GAC CCT  1860
Tyr Lys Pro Phe Gln Asp Leu Ile Pro Gly Cys Pro Gly Asp Pro   620

GCC CCA GTC CCT GTC CCC TTG TTC ACC TTT GGA CTG GAC AGG GAG  1905
Ala Pro Val Pro Val Pro Leu Phe Thr Phe Gly Leu Asp Arg Glu   635

CCA CCT CGC AGT CCG CAG AGC TCA CAT CTC CCA AGC AGC TCC CCA  1950
Pro Pro Arg Ser Pro Gln Ser Ser His Leu Pro Ser Ser Ser Pro   650

GAG CAC CTG GGT CTG GAG CCG GGG GAA AAG GTA GAG GAC ATG CCA  1995
Glu His Leu Gly Leu Glu Pro Gly Glu Lys Val Glu Asp Met Pro   665

AAG CCC CCA CTT CCC CAG GAG CAG GCC ACA GAC CCC CTT GTG GAC  2040
Lys Pro Pro Leu Pro Gln Glu Gln Ala Thr Asp Pro Leu Val Asp   680

AGC CTG GGC AGT GGC ATT GTC TAC TCA GCC CTT ACC TGC CAC CTG  2085
Ser Leu Gly Ser Gly Ile Val Tyr Ser Ala Leu Thr Cys His Leu   695

TGC GGC CAC CTG AAA CAG TGT CAT GGC CAG GAG GAT GGT GGC CAG  2130
Cys Gly His Leu Lys Gln Cys His Gly Gln Glu Asp Gly Gly Gln   710

ACC CCT GTC ATG GCC AGT CCT TGC TGT GGC TGC TGC TGT GGA GAC  2175
Thr Pro Val Met Ala Ser Pro Cys Cys Gly Cys Cys Cys Gly Asp   725

AGG TCC TCG CCC CCT ACA ACC CCC TGA GGG CCA GAC CCC TCT  2220
Arg Ser Ser Pro Pro Thr Thr Pro Leu Arg Ala Pro Asp Pro Ser   740

CCA GGT GGG GTT CCA CTG GAG GCC AGT CTG TGT CCG GCC TCC CTG  2265
Pro Gly Gly Val Pro Leu Glu Ala Ser Leu Cys Pro Ala Ser Leu   755

GCA CCC TCG GGC ATC TCA GAG AAG AGT AAA TCC TCA TCA TCC TTC  2310
Ala Pro Ser Gly Ile Ser Glu Lys Ser Lys Ser Ser Ser Ser Phe   770

CAT CCT GCC CCT GGC AAT GCT CAG AGC TCA AGC CAG ACC CCC AAA  2355
His Pro Ala Pro Gly Asn Ala Gln Ser Ser Ser Gln Thr Pro Lys   785

ATC GTG AAC TTT GTC TCC GTG GGA CCC ACA TAC ATG AGG GTC TCT  2400
Ile Val Asn Phe Val Ser Val Gly Pro Thr Tyr Met Arg Val Ser   800
```

Figure 2A

```
         FR1
L1   1  GAAATTGTGT TGACGCAGTC TCCAGGCACC CTGTCTTTGT CTCCAGGGGA AAGAGCCACC   60
L2   1  GAAATTGTGT TGACGCAGTC TCCAGGCACC CTGTCTTTGT CTCCAGGGGA AAGAGCCACC   60
L3   1  GAAATTGTGT TGACGCAGTC TCCAGGCACC CTGTCTTTGT CTCCGGGGGA AAGAGCCACC   60
L4   1  GAAATTGTGA TGACGCAGTC TCCAGGCACC CTGTCTTTGT CTCCAGGGGA AAGAGCCACC   60
L5   1  GATATTGTGC TGACCCAGTC TCCAGCCACC CTGTCTTTGT CTCCAGGGGA AAGAGCCACC   60
L6   1  GATATTGTGC TGACGCAGAC TCCAGCCACC CTGTCTTTGT CTCCAGGGGA AAGAGCCACC   60

CDR1
L1  61  CTCTCCTGCA GGGCCAGTCA GAGTGTTAGC AGCAGCTACT TAGCCTGGTA CCAGCAGAAA  120
L2  61  CTCTCCTGCA GGGCCAGTCA GAGTGTTAGC AACAGCTACT TAGCCTGGTA CCAGCAGAAA  120
L3  61  CTCTCCTGCA GGGCCAGTCA GACTGTTAAC AGCGACTACT TAGCCTGGTA CCAGCAGAAA  120
L4  61  CTCTCCTGCA GGGCCAGTCA GAGTGTTAGC AGCGACTACT TAGCCTGGTA CCAGCAGAAA  120
L5  61  CTCTCCTGCA GGGCCAGTCA GAGTGTTAAC AGCAACTACT TAGCCTGGTA CCAGCAGAAA  120
L6  61  CTCTCCTGCA GGGCCAGTCA GAGTGTTGGC AGCAGCTACT TAGCCTGGTA CCAGCAGAGA  120

FR2                              CDR2
L1 121  CCTGGCCAGG CTCCCAGGCT CCTCATCTTT GGTGCATCCA GCAGGGCCAC TGGCATCCCA  180
L2 121  CCTGGCCAGG CTCCCAGGCT CCTCATCTAT GGTGCATCCA GCAGGGCCCC TGGCATCCCA  180
L3 121  CCGGGCCAGG CTCCCAGGCT CCTCATCTAT GGTGCATCCA GCAGGGCCAC TGGCATCCCA  180
L4 121  CCTGGCCAGG CTCCCAGGCT CCTCATCTAT GGTGCATCTA GCAGGGCCTC TGGCATCCCA  180
L5 121  CCTGGCCAGG CTCCCAGGCT CCTCATCTAT GGTACATCCT ACAGGGCCAC TGGCATCCCA  180
L6 121  CCTGGCCAGG CTCCCAGGCT CCTCATCTAT GGTGCATCCA GCAGGGCCAC TGGCATCCCG  180

FR3
L1 181  GACAGGTTCA GTGGCAGTGG GTCTGGGACA GACTTCACTC TCACCATCAG CAGACTGGAG  240
L2 181  GACAGGTTCA GTGGCAGTGG GTCTGGGACA GACTTCACTC TCACCATCAG CAGACTGGAG  240
L3 181  GACAGGTTCA GTGGCAGTGG GTCTGGGACA GACTTCACTC TCACCATCAG CAGACTGGAG  240
L4 181  GACAGGTTCA GTGGCAGTGG GTTTGGGACA GACTTCACTC TCACCATCAG CAGACTGGAG  240
L5 181  GACAGGTTCA GTGGCAGTGG GTCTGGGACA GACTTCACTC TCACCATCAC CAGACTGGAG  240
L6 181  GACAGGTTCA GTGGCAGTGG GTCTGGGACA GACTTCACTC TCACGATCAG CAGACTGGAG  240

CDR3
L1 241  CCTGAAGATT TTGCAGTGTA TTACTGTCAG CAGTATGGTA GCTCACCTCC GTGGACGTTC  300
L2 241  CCTGAAGATT TTGCAGTGTA TTACTGTCAG CAGTATGATC ACTCAGCAGG GTGGACGTTC  300
L3 241  CCTGAAGATT TTGCAGTCTA TTACTGTCAG CAGTATGGTA GGTCACCTCC GTGGACGTTC  300
L4 241  CCTGAAGATT TTGCAATATA TTACTGTCAG CAGTATGGTA GCTCACCTCC GTGGACGTTC  300
L5 241  CCTGAAGATT TTGCAGTGTA TTACTGTCAG CAGTATGGTA GCTCACCACC GTGGACGTTC  300
L6 241  CCTGAAGATT TTGCAGTGTA TTATTGTCAG CAGTATGAA GTTCACCTCC GTGGATGTTC  300

FR4
L1 301  GGCCAAGGGA CCAAGGTGGA AATCAAA   327
L2 301  GGCCAAGGGA CCAAGGTGGA GATCAAA   327
L3 301  GGCCAAGGGA CCAAAGTGGA TATCAAA   327
L4 301  GGCCAAGGGA CCAAGGTGGA AATCAAA   327
L5 301  GGCCAAGGGA CACGACTGGA GATTAAA   327
L6 301  GGCCAAGGGA CCAAGGTGGA GATCAAA   327
```

Figure 2B

```
                          FR1
H1   1  GAGGTTCAGC TGGTGCAGTC TGGGGGAGGC TTGGTACATC CTGGGGGGTC CCTGAGACTC  60
H2   1  GAGGTTCAGC TGGTGCAGTC TGGGGGAGGC TTGGTACATC CTGGGGGGTC CCTGAGACTC  60
H3   1  GAGGTTCAGC TGGTGCAGTC TGGGGGAGGC TTGGTACATC CTGGGGGGTC CCTGAGACTC  60
H4   1  GAGGTTCAGT TGGTGCAGTC TGGGGGAGGC TTGGTACATC CTGGGGGGTC CCTGAGACTC  60
H5   1  GAGGTTCAGC TGGTGCAGTC TGGGGGAGGC TTGGTACATC CTGGGGGGTC CCTGAGACTC  60
H6   1  GAGGTTCAGT TGGTGCAGTC TGGGGGAGGC TTGGTACATC CTGGGGGGTC CCTGAGACTC  60
H7   1  GAGGTTCAGC TGGTGCAGTC TGGGGGAGGC TTGGTACATC CTGGGGGGTC CCTGAGACTC  60
H8   1  GAGGTTCAGT TGGTGCAGTC TGGGGGAGGC TTGGTACATC CTGGGGGGTC CCTGAGACTC  60
H9   1  GAGGTTCAGC TGGTGCAGTC TGGGGGAGGC TTGGTACATC CTGGGGGGTC CCTGAGACTC  60
H10  1  GAGGTTCAGT TGGTGCAGTC TGGGGGAGGC TTGGTACATC CTGGGGGGTC CCTGAGACTC  60
H11  1  GAGGTTCAGC TGGTGCAGTC TGGGGGAGGC TTGGTACATC CTGGGGGGTC CCTGAGACTC  60
H12  1  GAGGTTCAGC TGGTGCAGTC TGGGGGAGGC TTGGTACATC CTGGGGGGTC CCTGAGACTC  60
H13  1  GAGGTTCAGC TGGTGCAGTC TGGGGGAGGC TTGGTACATC CTGGGGGGTC CCTGAGACTC  60
H14  1  GAGGTTCAGT TGGTGGAGTC TGGGGGAGGC TTGGTACAGC CTGGGGGGTC CCTGAGACTC  60
H15  1  GAGGTTCAGT TGGTGGAGTC TGGGGGAGGC TTGGTACAGC CTGGGGGGTC CCTGAGACTC  60
H16  1  GAGGTTCAGT TGGTGGAGTC TGGGGGAGGC TTGGTACAGC CTGGGGGGTC CCTGAGACTC  60
H17  1  GAGGTTCAGT TGGTGGAGTC TGGGGGAGGC TTGGTACAGC CTGGGGGGTC CCTGAGACTC  60
H18  1  GAGGTTCAGT TGGTGGAGTC TGGGGGAGGC TTGGTACAGC CTGGGGGGTC CCTGAGACTC  60
H19  1  GAGGTTCAGT TGGTGGAGTC TGGGGGAGGC TTGGTACAGC CTGGGGGGTC CCTGAGACTC  60
H20  1  GAGGTTCAGT TGGTGGAGTC TGGGGGAGGC TTGGTACAGC CTGGGGGGTC CCTGAGACTC  60
H21  1  GAGGTTCAGT TGGTGGAGTC TGGGGGAGGC TTGGTACAGC CTGGGGGGTC CCTGAGACTC  60
H22  1  GAGGTTCAGT TGGTGGAGTC TGGGGGAGGC TTGGTACAGC CTGGGGGGTC CCTGAGACTC  60
H23  1  GAGGTTCAGT TGGTGGAGTC TGGGGGAGGC TTGGTACAGC CTGGGGGGTC CCTGAGACTC  60
H24  1  GAGGTTCAGT TGGTGGAGTC TGGGGGAGGC TTGGTACAGC CTGGGGGGTC CCTGAGACTC  60

CDR1
H1   61 TCCTGTGCAG GCTCTGGATT CACCTTCAGT AGAAATGCTA TGTTCTGGGT TCGCCAGGCT 120
H2   61 TCCTGTGCAG GCTCTGGATT CACCTTCAGT AGAAATGCTA TGTTCTGGGT TCGCCAGGCT 120
H3   61 TCCTGTGCAG GCTCTGGATT CACCTTCAGT AGAAATGCTA TGTTCTGGGT TCGCCAGGCT 120
H4   61 TCCTGTGCAG GCTCTGGATT CACCTTCAGT AGAAATGCTA TGTTCTGGGT TCGCCAGGCT 120
H5   61 TCCTGTGCAG GCTCTGGATT CACCTTCAGT AGAAATGCTA TGTTCTGGGT TCGCCAGGCT 120
H6   61 TCCTGTGCAG GCTCTGGATT CACCTTCAGT AGAAATGCTA TGTTCTGGGT TCGCCAGGCT 120
H7   61 TCCTGTGCAG GCTCTGGATT CACCTTCAGT AGAAATGCTA TGTTCTGGGT TCGCCAGGCT 120
H8   61 TCCTGTGCAG GCTCTGGATT CACCTTCAGT AGAAATGCTA TGTTCTGGGT TCGCCAGGCT 120
H9   61 TCCTGTGCAG GCTCTGGATT CACCTTCAGT AGAAATGCTA TGTTCTGGGT TCGCCAGGCT 120
H10  61 TCCTGTGCAG GCTCTGGATT CACCTTCAGT AGAAATGCTA TGTTCTGGGT TCGCCAGGCT 120
H11  61 TCCTGTGCAG GCTCTGGATT CACCTTCAGT AGAAATGCTA TGTTCTGGGT TCGCCAGGCT 120
H12  61 TCCTGTGCAG GCTCTGGATT CACCTTCAGT AGAAATGCTA TGTTCTGGGT TCGCCAGGCT 120
H13  61 TCCTGTGCAG GCTCTGGATT CACCTTCAGT AGAAATGCTA TGTTCTGGGT TCGCCAGGCT 120
H14  61 TCCTGTGCAG CCTCTGGATT CACCTTCAGT AGAAATGCTA TGTTCTGGGT TCGCCAGGCT 120
H15  61 TCCTGTGCAG CCTCTGGATT CACCTTCAGT AGAAATGCTA TGTTCTGGGT TCGCCAGGCT 120
H16  61 TCCTGTGCAG CCTCTGGATT CACCTTCAGT AGAAATGCTA TGTTCTGGGT TCGCCAGGCT 120
H17  61 TCCTGTGCAG CCTCTGGATT CACCTTCAGT AGAAATGCTA TGTTCTGGGT TCGCCAGGCT 120
H18  61 TCCTGTGCAG CCTCTGGATT CACCTTCAGT AGAAATGCTA TGTTCTGGGT TCGCCAGGCT 120
H19  61 TCCTGTGCAG CCTCTGGATT CACCTTCAGT AGAAATGCTA TGTTCTGGGT TCGCCAGGCT 120
H20  61 TCCTGTGCAG CCTCTGGATT CACCTTCAGT AGAAATGCTA TGTTCTGGGT TCGCCAGGCT 120
H21  61 TCCTGTGCAG CCTCTGGATT CACCTTCAGT AGAAATGCTA TGTTCTGGGT TCGCCAGGCT 120
H22  61 TCCTGTGCAG CCTCTGGATT CACCTTCAGT AGAAATGCTA TGTTCTGGGT TCGCCAGGCT 120
H23  61 TCCTGTGCAG CCTCTGGATT CACCTTCAGT AGAAATGCTA TGTTCTGGGT TCGCCAGGCT 120
H24  61 TCCTGTGCAG CCTCTGGATT CACCTTCAGT AGAAATGCTA TGTTCTGGGT TCGCCAGGCT 120
```

Figure 2C

```
            FR2                                         CDR2
H1   121 CCAGGAAAAG GTCTGGAGTG GGTATCAGGT ATTGGTACTG GTGGTGCCAC AAACTATGCA 180
H2   121 CCAGGAAAAG GTCTGGAGTG GGTATCAGGT ATTGGTACTG GTGGTGCCAC AAGCTATGCA 180
H3   121 CCAGGAAAAG GTCTGGAGTG GGTATCAGGT ATTGGTACTG GTGGTGCCAC AAGCTATGCA 180
H4   121 CCAGGAAAAG GTCTGGAGTG GGTATCAGGT ATTGGTACTG GTGGTGCCAC AAACTATGCA 180
H5   121 CCAGGAAAAG GTCTGGAGTG GGTATCAGGT ATTGGTACTG GTGGTGCCAC AAACTATGCA 180
H6   121 CCAGGAAAAG GTCTGGAGTG GGTATCAGGT ATTGGTACTG GTGGTGCCAC AAACTATGCA 180
H7   121 CCAGGAAAAG GTCTGGAGTG GGTATCAGGT ATTGGTACTG GTGGTGCCAC AAGCTATGCA 180
H8   121 CCAGGAAAAG GTCTGGAGTG GGTATCAGGT ATTGGTACTG GTGGTGCCAC AAACTATGCA 180
H9   121 CCAGGAAAAG GTCTGGAGTG GGTATCAGGT ATTGGTACTG GTGGTGCCAC AAGCTATGCA 180
H10  121 CCAGGAAAAG GTCTGGAGTG GGTATCAGGT ATTGGTACTG GTGGTGCCAC AAACTATGCA 180
H11  121 CCAGGAAAAG GTCTGGAGTG GGTATCAGGT ATTGGTACTG GTGGTGCCAC AAGCTATGCA 180
H12  121 CCAGGAAAAG GTCTGGAGTG GGTATCAGGT ATTGGTACTG GTGGTGCCAC AAGCTATGCA 180
H13  121 CCAGGAAAAG GTCTGGAGTG GGTATCAGGT ATTGGTACTG GTGGTGCCAC AAGCTATGCA 180
H14  121 CCAGGAAAAG GTCTGGAGTG GGTATCAGGT ATTGGTACTG GTGGTGCCAC AAGCTATGCA 180
H15  121 CCAGGAAAAG GTCTGGAGTG GGTATCAGGT ATTGGTACTG GTGGTGCCAC AAGCTATGCA 180
H16  121 CCAGGAAAAG GTCTGGAGTG GGTATCAGGT ATTGGTACTG GTGGTGCCAC AAGCTATGCA 180
H17  121 CCAGGAAAAG GTCTGGAGTG GGTATCAGGT ATTGGTACTG GTGGTGCCAC AAGCTATGCA 180
H18  121 CCAGGAAAAG GTCTGGAGTG GGTATCAGGT ATTGGTACTG GTGGTGCCAC AAGCTATGCA 180
H19  121 CCAGGAAAAG GTCTGGAGTG GGTATCAGGT ATTGGTACTG GTGGTGCCAC AAGCTATGCA 180
H20  121 CCAGGAAAAG GTCTGGAGTG GGTATCAGGT ATTGGTACTG GTGGTGCCAC AAGCTATGCA 180
H21  121 CCAGGAAAAG GTCTGGAGTG GGTATCAGGT ATTGGTACTG GTGGTGCCAC AAGCTATGCA 180
H22  121 CCAGGAAAAG GTCTGGAGTG GGTATCAGGT ATTGGTACTG GTGGTGCCAC AAGCTATGCA 180
H23  121 CCAGGAAAAG GTCTGGAGTG GGTATCAGGT ATTGGTACTG GTGGTGCCAC AAGCTATGCA 180
H24  121 CCAGGAAAAG GTCTGGAGTG GGTATCAGGT ATTGGTACTG GTGGTGCCAC AAGCTATGCA 180

FR3
H1   181 GACTCCGTGA AGGGCCGATT CACCATCTCC AGAGACAATG CCAAGAACTC CTTGTATCTT 240
H2   181 GACTCCGTGA AGGGCCGATT CACCATCTCC AGAGACAATG CCAAGAACTC CTTGTATCTT 240
H3   181 GACTCCGTGA AGGGCCGATT CACCATCTCC AGAGACAATG CCAAGAACTC CTTGTATCTT 240
H4   181 GACTCCGTGA AGGGCCGATT CACCATCTCC AGAGACAATG CCAAGAACTC CTTGTATCTT 240
H5   181 GACTCCGTGA AGGGCCGATT CACCATCTCC AGAGACAATG CCAAGAACTC CTTGTATCTT 240
H6   181 GACTCCGTGA AGGGCCGATT CACCATCTCC AGAGACAATG CCAAGAACTC CTTGTATCTT 240
H7   181 GACTCCGTGA AGGGCCGATT CACCATCTCC AGAGACAATG CCAAGAACTC CTTGTATCTT 240
H8   181 GACTCCGTGA AGGGCCGATT CACCATCTCC AGAGACAATG CCAAGAACTC CTTGTATCTT 240
H9   181 GACTCCGTGA AGGGCCGATT CACCATCTCC AGAGACAATG CCAAGAACTC CTTGTATCTT 240
H10  181 GACTCCGTGA AGGGCCGATT CACCATCTCC AGAGACAATG CCAAGAACTC CTTGTATCTT 240
H11  181 GACTCCGTGA AGGGCCGATT CACCATCTCC AGAGACAATG CCAAGAACTC CTTGTATCTT 240
H12  181 GACTCCGTGA AGGGCCGATT CACCATCTCC AGAGACAATG CCAAGAACTC CTTGTATCTT 240
H13  181 GACTCCGTGA AGGGCCGATT CACCATCTCC AGAGACAATG CCAAGAACTC CTTGTATCTT 240
H14  181 GACTCCGTGA AGGGCCGATT CACCATCTCC AGAGACAATG CCAAGAACTC CTTGTATCTT 240
H15  181 GACTCCGTGA AGGGCCGATT CACCATCTCC AGAGACAATG CCAAGAACTC CTTGTATCTT 240
H16  181 GACTCCGTGA AGGGCCGATT CACCATCTCC AGAGACAATG CCAAGAACTC CTTGTATCTT 240
H17  181 GACTCCGTGA AGGGCCGATT CACCATCTCC AGAGACAATG CCAAGAACTC CTTGTATCTT 240
H18  181 GACTCCGTGA AGGGCCGATT CACCATCTCC AGAGACAATG CCAAGAACTC CTTGTATCTT 240
H19  181 GACTCCGTGA AGGGCCGATT CACCATCTCC AGAGACAATG CCAAGAACTC CTTGTATCTT 240
H20  181 GACTCCGTGA AGGGCCGATT CACCATCTCC AGAGACAATG CCAAGAACTC CTTGTATCTT 240
H21  181 GACTCCGTGA AGGGCCGATT CACCATCTCC AGAGACAATG CCAAGAACTC CTTGTATCTT 240
H22  181 GACTCCGTGA AGGGCCGATT CACCATCTCC AGAGACAATG CCAAGAACTC CTTGTATCTT 240
H23  181 GACTCCGTGA AGGGCCGATT CACCATCTCC AGAGACAATG CCAAGAACTC CTTGTATCTT 240
H24  181 GACTCCGTGA AGGGCCGATT CACCATCTCC AGAGACAATG CCAAGAACTC CTTGTATCTT 240
```

Figure 2D

```
H1   241 CAAATGAACA GCCTGAGAGC CGAGGACATG GCTGTGTATT ACTGTGCAAG AGGGAGGTAC 300
H2   241 CAAATGAACA GCCTGAGTGC CGAGGACATG GCTGTGTATT ACTGTGCAAG AGGGAGGTAC 300
H3   241 CAAATGAACA GCCTGAGAGC CGAGGACATG GCTGTGTATT ACTGTGCAAG AGGGAGGTAC 300
H4   241 CAAATGAACA GCCTGAGAGC CGAGGACATG GCTGTGTATT ACTGTGCAAG AGGGAGGTAC 300
H5   241 CAAATGAACA GCCTGAGAGC CGAGGACATG GCTGTGTATT ACTGTGCAAG AGGGAGGTAC 300
H6   241 CAAATGAACA GCCTGAGAGC CGAGGACATG GCTGTGTATT ACTGTGCAAG AGGGAGGTAC 300
H7   241 CAAATGAACA GCCTGAGAGC CGAGGACATG GCTGTGTATT ACTGTGCAAG AGGGAGGTAC 300
H8   241 CAAATGAACA GCCTGAGAGC CGAGGACATG GCTGTGTATT ACTGTGCAAG AGGGAGGTAC 300
H9   241 CAAATGAACA GCCTGAGAGC CGAGGACATG GCTGTGTATT ACTGTGCAAG AGGGAGGTAC 300
H10  241 CAAATGAACA GCCTGAGAGC CGAGGACATG GCTGTGTATT ACTGTGCAAG AGGGAGGTAC 300
H11  241 CAAATGAACA GCCTGAGAGC CGAGGACATG GCTGTGTATT ACTGTGCAAG AGGGAGGTAC 300
H12  241 CAAATGAACA GCCTGAGAGC CGAGGACATG GCTGTGTATT ACTGTGCAAG AGGGAGGTAC 300
H13  241 CAAATGAACA GCCTGAGTGC CGAGGACATG GCTGTGTATT ACTGTGCAAG AGGGAGGTAC 300
H14  241 CAAATGAACA GCCTGAGAGC CGAGGACACG GCTGTGTATT ACTGTGCAAG AGGGAGGTAC 300
H15  241 CAAATGAACA GCCTGAGAGC CGAGGACACG GCTGTGTATT ACTGTGCAAG AGGGAGGTAC 300
H16  241 CAAATGAACA GCCTGAGAGC CGAGGACACG GCTGTGTATT ACTGTGCAAG AGGGAGGTAC 300
H17  241 CAAATGAACA GCCTGAGAGC CGAGGACACG GCTGTGTATT ACTGTGCAAG AGGGAGGTAC 300
H18  241 CAAATGAACA GCCTGAGAGC CGAGGACACG GCTGTGTATT ACTGTGCAAG AGGGAGGTAC 300
H19  241 CAAATGAACA GCCTGAGAGC CGAGGACACG GCTGTGTATT ACTGTGCAAG AGGGAGGTAC 300
H20  241 CAAATGAACA GCCTGAGAGC CGAGGACACG GCTGTGTATT ACTGTGCAAG AGGGAGGTAC 300
H21  241 CAAATGAACA GCCTGAGAGC CGAGGACACG GCTGTGTATT ACTGTGCAAG AGGGAGGTAC 300
H22  241 CAAATGAACA GCCTGAGAGC CGAGGACACG GCTGTGTATT ACTGTGCAAG AGGGAGGTAC 300
H23  241 CAAATGAACA GCCTGAGAGC CGAGGACACG GCTGTGTATT ACTGTGCAAG AGGGAGGTAC 300
H24  241 CAAATGAACA GCCTGAGAGC CGAGGACACG GCTGTGTATT ACTGTGCAAG AGGGAGGTAC 300

CDR3                    FR4
H1   301 TACTTTGACT ACTGGGGCCA GGGAACCCTG GTCACCGTCT CCTCA 345
H2   301 TACTTCACCC ACTGGGGCCA GGGAACCCTG GTCACCGTCT CCTCA 345
H3   301 TGGTACAACA ACTGGGGCCA GGGAACCCTG GTCACCGTCT CCTCA 345
H4   301 TACTTCCCGT GGTGGGGCCA GGGAACCCTG GTCACCGTCT CCTCA 345
H5   301 TACTTCACGA GGTGGGGCCA GGGAACCCTG GTCACCGTCT CCTCA 345
H6   301 TGGTACCCGT GGTGGGGCCA GGGAACCCTG GTCACCGTCT CCTCA 345
H7   301 TGGTACCCGT GGTGGGGCCA GGGAACCCTG GTCACCGTCT CCTCA 345
H8   301 TGGTTCCCGT GGTGGGGCCA GGGAACCCTG GTCACCGTCT CCTCA 345
H9   301 TGGTTCCCGT GGTGGGGCCA GGGAACCCTG GTCACCGTCT CCTCA 345
H10  301 TGGTACCCGT GGTGGGGCCA GGGAACCCTG GTCACCGTCT CCTCA 345
H11  301 TGGTACCCGT GGTGGGGCCA GGGAACCCTG GTCACCGTCT CCTCA 345
H12  301 TACTTCCCGT GGTGGGGCCA GGGAACCCTG GTCACCGTCT CCTCA 345
H13  301 TACTTCCCGT GGTGGGGCCA GGGAACCCTG GTCACCGTCT CCTCA 345
H14  301 TACTTCCCGT GGTGGGGCCA GGGAACCCTG GTCACCGTCT CCTCA 345
H15  301 TACTTTGACT ACTGGGGCCA GGGAACCCTG GTCACCGTCT CCTCA 345
H16  301 TACTTCACCC ACTGGGGCCA GGGAACCCTG GTCACCGTCT CCTCA 345
H17  301 TGGTACAACA ACTGGGGCCA GGGAACCCTG GTCACCGTCT CCTCA 345
H18  301 TACTTCACGA GGTGGGGCCA GGGAACCCTG GTCACCGTCT CCTCA 345
H19  301 TGGTACCCGT GGTGGGGCCA GGGAACCCTG GTCACCGTCT CCTCA 345
H20  301 TGGTACCCGT GGTGGGGCCA GGGAACCCTG GTCACCGTCT CCTCA 345
H21  301 TGGTTCCCGT GGTGGGGCCA GGGAACCCTG GTCACCGTCT CCTCA 345
H22  301 TGGTTCCCGT GGTGGGGCCA GGGAACCCTG GTCACCGTCT CCTCA 345
H23  301 TGGTACCCGT GGTGGGGCCA GGGAACCCTG GTCACCGTCT CCTCA 345
H24  301 TGGTACCCGT GGTGGGGCCA GGGAACCCTG GTCACCGTCT CCTCA 345
```

Figure 3

```
          FR1                              CDR1           FR2              CDR2                 FR3                        CDR3         FR4
L1   EIVLTQSPGTLSLSPGERATLSCRASQSVSSSYLAWYQQKPGQAPRLLIFGASSRATGIPDRFSGSGSGTDFTLTISRLEPEDFAVYYCQQYGSSPPWTFGQGTKVEIK
L2   ------------------------------------------N--------------Y--P--------------------------------------DH-AG---------
L3   -----------------------------T-N-D-----------------------Y---------------------------------------------R--------D
L4   --M-----------------------------D------------------------Y----S--------F-----------------I----------------------D
L5   D-----------A-------------------N-N----------------------Y-T-Y---------T----------------------------------RL----
L6   D-----T-A-------------------------G----------------------Y---R----------------------------------------M---------

FR1                          CDR1            FR2              CDR2              FR3                              CDR3       FR4
H1   EVQLVQSGGGLVHPGGSLRLSCAGSGFTFSRNAMFWVRQAPGKGLEWVSGIGTGGATNYADSVKGRFTISRDNAKNSLYLQMNSLRAEDMAVYYCARGRYYFDYWGQGTLVTVSS
H2   --------------------------------------------------------S-----------------------------------------------TH------
H3   --------------------------------------------------------S------------------------------------------WYNN----------
H4   --------------------------------------------------------S------------------------------------------- -PW---------
H5   --------------------------------------------------------S------------------------------------------- -TR---------
H6   --------------------------------------------------------S------------------------------------------- -YPW--------
H7   --------------------------------------------------------S------------------------------------------- -YPW--------
H8   --------------------------------------------------------S------------------------------------------W -PW---------
H9   --------------------------------------------------------S------------------------------------------W -PW---------
H10  --------------------------------------------------------S------------------------------------------WYPW----------
H11  --------------------------------------------------------S------------------------------------------WYPW----------
H12  --------------------------------------------------------S------------------------------------------- -PW---------
H13  --------------------------------------------------------S-------------------------------S----------- -PW---------
H14  -------E-----------------A------------------------------S-------------------------------T----------- -PW---------
H15  -------E-----------------A------------------------------S-------------------------------T----------- -TH---------
H16  -------E-----------------A------------------------------S-------------------------------T----------WYNN----------
H17  -------E-----------------A------------------------------S-------------------------------T----------- -TR---------
H18  -------E-----------------A------------------------------S-------------------------------T----------- -YPW--------
H19  -------E-----------------A------------------------------S-------------------------------T----------- -YPW--------
H20  -------E-----------------A------------------------------S-------------------------------T----------- -YPW--------
H21  -------E-----------------A------------------------------S-------------------------------T----------W -PW---------
H22  -------E-----------------A------------------------------S-------------------------------T----------W -PW---------
H23  -------E-----------------A------------------------------S-------------------------------T----------WYPW----------
H24  -------E-----------------A------------------------------S-------------------------------T----------WYPW----------
```

NUCLEIC ACIDS ENCODING ANTIBODIES THAT BIND INTERLEUKIN-4 RECEPTOR

CROSS-REFERENCE TO RELATED APPLICATION

This application is a divisional of U.S. patent application Ser. No. 10/578,410, filed Mar. 5, 2007, now U.S. Pat. No. 7,638,606, which claims the benefit of International Application Number PCT/US04/37242, filed Nov. 4, 2004, and U.S. provisional application No. 60/518,166, filed Nov. 7, 2003. The above-identified applications are incorporated herein by reference.

BACKGROUND OF THE INVENTION

Interleukin-4 (IL-4), previously known as B cell stimulating factor, or BSF-1, was originally characterized by its ability to stimulate the proliferation of B cells in response to low concentrations of antibodies directed to surface immunoglobulin. IL-4 has been shown to possess a far broader spectrum of biological activities, including growth co-stimulation of T cells, mast cells, granulocytes, megakaryocytes, and erythrocytes. In addition, IL-4 stimulates the proliferation of several IL-2- and IL-3-dependent cell lines, induces the expression of class II major histocompatibility complex molecules on resting B cells, and enhances the secretion of IgE and IgG1 isotypes by stimulated B cells. IL-4 is associated with a TH2-type immune response, being one of the cytokines secreted by TH2 cells.

Murine and human IL-4 have been identified and characterized, including cloning of IL-4 cDNAs and determination of the nucleotide and encoded amino acid sequences. See Yokota et al., 1986, Proc. Natl. Acad. Sci. USA 83:5894; Noma et al., 1986, Nature 319:640; Grabstein et al., 1986, J. Exp. Med. 163:1405; and U.S. Pat. No. 5,017,691.

IL-4 binds to particular cell surface receptors, which results in transduction of a biological signal to cells such as various immune effector cells. IL-4 receptors are described, and DNA and amino acid sequence information presented, in Mosley et al., 1989, Cell 59:335-48, (murine IL-4R); Idzerda et al., 1990, J. Exp. Med. 171:861-73, (human IL-4R); and U.S. Pat. No. 5,599,905. The IL-4 receptor described in these publications is sometimes referred to as IL-4R alpha.

Other proteins have been reported to be associated with IL-4R alpha on some cell types, and to be components of multi-subunit IL-4 receptor complexes. One such subunit is IL-2R gamma, also known as IL-2R gamma c. See the discussion of IL-4R complexes in Sato et al., 1994, Current Opinion in Cell Biology, 6:174-79. IL-4R alpha also has been reported to be a component of certain multi-subunit IL-13 receptor complexes. See Zurawski et al., 1995, J. Biol. Chem. 270:13869; de Vries, 1998, J. Allergy Clin. Immunol. 102:165; and Callard et al., 1996, Immunology Today, 17:108.

IL-4 has been implicated in a number of disorders, examples of which are allergy and asthma.

SUMMARY OF THE INVENTION

The present invention provides methods and compositions relating to novel IL-4R antagonists, in particular antibodies and antibody derivatives, that bind IL-4R alpha.

In one aspect, the present invention provides an antibody, wherein the light chain variable domain comprises a sequence of amino acids that differs from SEQ ID NO:4 only by: at least one amino acid substitution selected from the group consisting of S28T, S30N, 530G, S31N, S32D, S32N, A52T, S54Y, T57P, T57S, G93D, S94H, S94R, P96A, P97G, and T99M, and, optionally, one or more amino acid substitutions selected from the group consisting of E1D, L4M, S7T, G9A, K40R, F50Y, S68F, S77T, V861, K105R, V106L, and E107D, and/or the heavy chain variable domain comprises a sequence of amino acids that differs from SEQ ID NO:16 only by: at least one amino acid substitution selected from the group consisting of N58S, Y101W, F102Y, D103T, D103N, D103P, Y104H, Y104N, Y104W, and Y104R, and, optionally, one or more amino acid substitutions selected from the group consisting of Q6E, H13Q, G24A, R86S, and M90T, wherein said antibody binds to IL-4 receptor alpha. In one embodiment, the light chain CDR1 comprises a sequence selected from the group consisting of residues 24-35 of SEQ ID NO:6, residues 24-35 of SEQ ID NO:8, residues 24-35 of SEQ ID NO:10, residues 24-35 of SEQ ID NO:12; and residues 24-35 of SEQ ID NO:14, the light chain CDR2 comprises a sequence selected from the group consisting of residues 51-57 of SEQ ID NO:4, residues 51-57 of SEQ ID NO:6, residues 51-57 of SEQ ID NO:10, and residues 51-57 of SEQ ID NO:12, the light chain CDR3 comprises a sequence selected from the group consisting of residues 90-99 of SEQ ID NO:4, residues 90-99 of SEQ ID NO:6, residues 90-99 of SEQ ID NO:8, and residues 90-99 of SEQ ID NO:14, the heavy chain CDR1 comprises the sequence residues 31-35 of SEQ ID NO:16, the heavy chain CDR2 comprises a sequence selected from the group consisting of residues 50-65 of SEQ ID NO:16, and residues 50-65 of SEQ ID NO:18, and/or the heavy chain CDR3 comprises a sequence selected from the group consisting of residues 98-104 of SEQ ID NO:16, residues 98-104 of SEQ ID NO:18, residues 98-104 of SEQ ID NO:20, residues 98-104 of SE ID NO:22, residues 98-104 of SEQ ID NO:24, residues 98-104 of SEQ ID NO:26, residues 98-104 of SEQ ID NO:30, and residues 98-104 of SEQ ID NO:34. In another embodiment, the light chain FR1 comprises a sequence selected from the group consisting of residues 1-23 of SEQ ID NO:4, residues 1-23 of SEQ ID NO:10, residues 1-23 of SEQ ID NO:12, and residues 1-23 of SEQ ID NO:14, the light chain FR2 comprises a sequence selected from the group consisting of residues 36-50 of SEQ ID NO:4, and residues 36-50 of SEQ ID NO:14, the light chain FR3 comprises a sequence selected from the group consisting of residues 58-89 of SEQ ID NO:4, residues 58-89 of SEQ ID NO:10, and residues 58-89 of SEQ ID NO:12, the light chain FR4 comprises a sequence selected from the group consisting of residues 100-109 of SEQ ID NO:4, residues 100-109 of SEQ ID NO:8, and residues 100-109 of SEQ ID NO:12, the heavy chain FR1 comprises a sequence selected from the group consisting of residues 1-30 of SEQ ID NO:16, and residues 1-30 of SEQ ID NO:42, the heavy chain FR2 comprises the sequence of residues 1-30 of SEQ ID NO:16, the heavy chain FR3 comprises a sequence selected from the group consisting of residues 66-97 of SEQ ID NO:16, residues 66-97 of SEQ ID NO:18, and residues 66-97 of SEQ ID NO:42, and/or the heavy chain FR4 comprises the sequence of residues 105-115 of SEQ ID NO:16.

In another aspect, the present invention provides an antibody comprising: a light chain variable domain comprising a sequence that is at least 80% identical to a sequence selected from the group consisting of SEQ ID NO:4, 6, 8, 10, 12, and 14, with the proviso that said light chain variable domain does not comprise the sequence of SEQ ID NO:4, and/or a heavy chain variable domain comprising a sequence that is at least 80% identical to a sequence selected from the group consisting of SEQ ID NO:16, 18, 20, 22, 24, 26, 28, 30, 32, 34, 36, 38, 40, 42, 44, 46, 48, 50, 52, 54, 56, 58, 60, and 62, with the proviso that said heavy chain variable domain does not comprise the sequence of SEQ ID NO:16, wherein said antibody binds to IL-4 receptor alpha. In one embodiment, said light chain variable domain comprises a sequence that is at least 85% identical to a sequence selected from the group consisting of SEQ ID NO:4, 6, 8, 10, 12, and 14, and/or said heavy chain variable domain comprises a sequence that is at least 85% identical to a sequence selected from the group consisting of SEQ ID NO:16, 18, 20, 22, 24, 26, 28, 30, 32, 34, 36, 38, 40, 42, 44, 46, 48, 50, 52, 54, 56, 58, 60, and 62. In another embodiment, said light chain variable domain comprises a sequence that is at least 90% identical to a sequence selected from the group consisting of SEQ ID NO:4, 6, 8, 10, 12, and 14, and/or said heavy chain variable domain comprises a sequence that is at least 90% identical to a sequence selected from the group consisting of SEQ ID NO:16, 18, 20, 22, 24, 26, 28, 30, 32, 34, 36, 38, 40, 42, 44, 46, 48, 50, 52, 54, 56, 58, 60, and 62. In another embodiment, said light chain variable domain comprises a sequence that is at least 95% identical to a sequence selected from the group consisting of SEQ ID NO:4, 6, 8, 10, 12, and 14, and/or said heavy chain variable domain comprises a sequence that is at least 95% identical to a sequence selected from the group consisting of SEQ ID NO:16, 18, 20, 22, 24, 26, 28, 30, 32, 34, 36, 38, 40, 42, 44, 46, 48, 50, 52, 54, 56, 58, 60, and 62. In another embodiment, said light chain variable domain comprises a sequence that is selected from the group consisting of SEQ ID NO:6, 8, 10, 12, and 14, and/or said heavy chain variable domain comprises a sequence that is selected from the group consisting of SEQ ID NO:16, 18, 20, 22, 24, 26, 28, 30, 32, 34, 36, 38, 40, 42, 44, 46, 48, 50, 52, 54, 56, 58, 60, and 62.

In another aspect, the present invention provides an antibody wherein the light chain variable domain comprises a sequence of at least 15 contiguous amino acids of a sequence selected from the group consisting of: SEQ ID NO:4, 6, 8, 10, 12, and 14, with the proviso that said light chain variable domain does not comprise the sequence of SEQ ID NO:4, and/or wherein the heavy chain variable domain comprises a sequence of at least 15 contiguous amino acids of a sequence selected from the group consisting of SEQ ID NO:16, 18, 20, 22, 24, 26, 28, 30, 32, 34, 36, 38, 40, 42, 44, 46, 48, 50, 52, 54, 56, 58, 60, and 62, with the proviso that said heavy chain variable domain does not comprise the sequence of SEQ ID NO:16, wherein said antibody binds to IL-4 receptor alpha. In one embodiment, the light chain variable domain comprises a sequence of at least 20 contiguous amino acids of a sequence selected from the group consisting of: SEQ ID NO:4, 6, 8, 10, 12, and 14, and/or the heavy chain variable domain comprises a sequence of at least 20 contiguous amino acids of a sequence selected from the group consisting of SEQ ID NO:16, 18, 20, 22, 24, 26, 28, 30, 32, 34, 36, 38, 40, 42, 44, 46, 48, 50, 52, 54, 56, 58, 60, and 62. In another embodiment, the light chain variable domain comprises a sequence of at least 25 contiguous amino acids of a sequence selected from the group consisting of: SEQ ID NO:4, 6, 8, 10, 12, and 14, and/or the heavy chain variable domain comprises a sequence of at least 25 contiguous amino acids of a sequence selected from the group consisting of: SEQ ID NO:16, 18, 20, 22, 24, 26, 28, 30, 32, 34, 36, 38, 40, 42, 44, 46, 48, 50, 52, 54, 56, 58, 60, and 62. In another embodiment, the light chain variable domain comprises a sequence of at least 35 contiguous amino acids of a sequence selected from the group consisting of: SEQ ID NO:4, 6, 8, 10, 12, and 14, and/or the heavy chain variable domain comprises a sequence of at least 35 contiguous amino acids of a sequence selected from the group consisting of: SEQ ID NO:16, 18, 20, 22, 24, 26, 28, 30, 32, 34, 36, 38, 40, 42, 44, 46, 48, 50, 52, 54, 56, 58, 60, and 62. In another embodiment, the light chain variable domain comprises a sequence of at least 50 contiguous amino acids of a sequence selected from the group consisting of: SEQ ID NO:4, 6, 8, 10, 12, and 14, and/or the heavy chain variable domain comprises a sequence of at least 50 contiguous amino acids of a sequence selected from the group consisting of: SEQ ID NO:16, 18, 20, 22, 24, 26, 28, 30, 32, 34, 36, 38, 40, 42, 44, 46, 48, 50, 52, 54, 56, 58, 60, and 62. In another embodiment, the light chain variable domain comprises a sequence of at least 75 contiguous amino acids of a sequence selected from the group consisting of: SEQ ID NO:4, 6, 8, 10, 12, and 14, and/or the heavy chain variable domain comprises a sequence of at least 75 contiguous amino acids of a sequence selected from the group consisting of: SEQ ID NO:16, 18, 20, 22, 24, 26, 28, 30, 32, 34, 36, 38, 40, 42, 44, 46, 48, 50, 52, 54, 56, 58, 60, and 62. In another embodiment, the light chain variable domain comprises a sequence of at least 100 contiguous amino acids of a sequence selected from the group consisting of: SEQ ID NO:4, 6, 8, 10, 12, and 14, and/or the heavy chain variable domain comprises a sequence of at least 100 contiguous amino acids of a sequence selected from the group consisting of: SEQ ID NO:16, 18, 20, 22, 24, 26, 28, 30, 32, 34, 36, 38, 40, 42, 44, 46, 48, 50, 52, 54, 56, 58, 60, and 62.

In another aspect, the present invention provides an antibody comprising: a light chain variable domain comprising an amino acid sequence that is encoded by a nucleotide sequence that is at least 80% identical to a nucleotide sequence selected from the group consisting of SEQ ID NO:3, 5, 7, 9, 11, and 13, and/or a heavy chain variable domain comprising an amino acid sequence that is encoded by a nucleotide sequence that is at least 80% identical to a nucleotide sequence selected from the group consisting of SEQ ID NO:15, 17, 19, 21, 23, 25, 27, 29, 31, 33, 35, 37, 39, 41, 43, 45, 47, 49, 51, 53, 55, 57, 59, and 61, with the proviso that said antibody does not comprise both the light chain variable domain sequence of SEQ ID NO:4 and the heavy chain variable domain sequence of SEQ ID NO:16, and wherein said antibody binds to IL-4 receptor alpha. In another embodiment, said light chain variable domain comprises an amino acid sequence that is encoded by a nucleotide sequence that is at least 85% identical to a nucleotide sequence selected from the group consisting of SEQ ID NO:3, 5, 7, 9, 11, and 13, and/or said heavy chain variable domain comprises an amino acid sequence that is encoded by a nucleotide sequence that is at least 85% identical to a nucleotide sequence selected from the group consisting of SEQ ID NO:15, 17, 19, 21, 23, 25, 27, 29, 31, 33, 35, 37, 39, 41, 43, 45, 47, 49, 51, 53, 55, 57, 59, and 61. In another embodiment, said light chain variable domain comprises an amino acid sequence that is encoded by a nucleotide sequence that is at least 90% identical to a nucleotide sequence selected from the group consisting of SEQ ID NO:3, 5, 7, 9, 11, and 13, and/or said heavy chain variable domain comprises an amino acid sequence that is encoded by a nucleotide sequence that is at least 90% identical to a nucleotide sequence selected from the group consisting of SEQ ID NO:15, 17, 19, 21, 23, 25, 27, 29, 31, 33, 35, 37, 39, 41, 43, 45, 47, 49, 51, 53, 55, 57, 59, and 61. In another embodiment, said light chain variable domain comprises an amino acid sequence that is encoded by a nucleotide sequence that is at least 95% identical to a nucleotide sequence selected from the group consisting of SEQ ID NO:3, 5, 7, 9, 11, and 13, and/or said heavy chain variable domain comprises an amino acid sequence that is encoded by a nucleotide sequence that is at least 95% identical to a nucleotide sequence selected from the group consisting of SEQ ID NO:15, 17, 19, 21, 23, 25, 27, 29, 31, 33, 35, 37, 39, 41, 43, 45, 47, 49, 51, 53, 55, 57, 59, and 61. In another embodiment, said light chain variable domain comprises an amino acid sequence that is encoded by a nucleotide sequence that is at least 98% identical to a nucleotide sequence selected from the group consisting of SEQ ID NO:3, 5, 7, 9, 11, and 13, and/or said heavy chain variable domain comprises an amino acid sequence that is encoded by a nucleotide sequence that is at least 98% identical to a nucleotide sequence selected from the group consisting of SEQ ID NO:15, 17, 19, 21, 23, 25, 27, 29, 31, 33, 35, 37, 39, 41, 43, 45, 47, 49, 51, 53, 55, 57, 59, and 61. In another embodiment, said light chain variable domain comprises an amino acid sequence that is encoded by a nucleotide sequence selected from the group consisting of SEQ ID NO:5, 7, 9, 11, and 13, and/or said heavy chain variable domain comprises an amino acid sequence that is encoded by a nucleotide sequence selected from the group consisting of SEQ ID NO:16, 18, 20, 22, 24, 26, 28, 30, 32, 34, 36, 38, 40, 42, 44, 46, 48, 50, 52, 54, 56, 58, 60, and 62.

In another aspect, the present invention provides an antibody comprising: a light chain variable domain comprising an amino acid sequence that is encoded by a nucleotide sequence that hybridizes under moderately stringent conditions to the complement of a nucleotide sequence selected from the group consisting of SEQ ID NO:3, 5, 7, 9, 11, and 13, and/or a heavy chain variable domain comprising an amino acid sequence that is encoded by a nucleotide sequence that hybridizes under moderately stringent conditions to the complement of a nucleotide sequence selected from the group consisting of SEQ ID NO:15, 17, 19, 21, 23, 25, 27, 29, 31, 33, 35, 37, 39, 41, 43, 45, 47, 49, 51, 53, 55, 57, 59, and 61, with the proviso that said antibody does not comprise both the light chain variable domain sequence of SEQ ID NO:4 and the heavy chain variable domain sequence of SEQ ID NO:16, and wherein said antibody binds to IL-4 receptor alpha. In one embodiment, said light chain variable domain comprises an amino acid sequence that is encoded by a nucleotide sequence that hybridizes under stringent conditions to the complement of a nucleotide sequence selected from the group consisting of SEQ ID NO:3, 5, 7, 9, 11, and 13, and/or said heavy chain variable domain comprises an amino acid sequence that is encoded by a nucleotide sequence that hybridizes under stringent conditions to the complement of a nucleotide sequence selected from the group consisting of SEQ ID NO:15, 17, 19, 21, 23, 25, 27, 29, 31, 33, 35, 37, 39, 41, 43, 45, 47, 49, 51, 53, 55, 57, 59, and 61.

In another aspect, the present invention provides an isolated antibody, wherein the light chain variable region of said antibody comprises an amino acid sequence selected from the group consisting of SEQ ID NO:6, 8, 10, 12, and 14, and said antibody binds to IL-4 receptor alpha.

In another aspect, the present invention provides an isolated antibody, wherein the heavy chain variable region of said antibody comprises an amino acid sequence selected from the group consisting of SEQ ID NO:16, 18, 20, 22, 24, 26, 28, 30, 32, 34, 36, 38, 40, 42, 44, 46, 48, 50, 52, 54, 56, 58, 60, and 62, and said antibody binds to IL-4 receptor alpha.

In another aspect, the present invention provides an antibody selected from the group consisting of L2H1, L3H1, L4H1, L5H1, L1H2, L1H3, L1H4, L1H5, L1H6, L1H7, L1H8, L1H9, L1H10, L1H11, L2H4, L2H12, L2H13, L2H14, L6H1, L2H2, L2H3, L2H6, L2H7, L2H8, L2H9, L2H10, and L2H11.

In another aspect, the present invention provides a human, humanized, or chimeric antibody.

In another aspect, the present invention provides a monoclonal antibody.

In another aspect, the present invention provides an antibody selected from the group consisting of an IgD, IgE, IgM, IgG1, IgG2, IgG3, IgG4, and IgG4 having at least one mutation in a hinge region that alleviates a tendency to form intra-H chain disulfide bond antibody.

In another aspect, the present invention provides an isolated polypeptide comprising an IL-4 receptor binding portion of an antibody of the invention. In one embodiment, said polypeptide comprises a Fab, F(ab')$_2$, scFv, diabody, triabody, or tetrabody.

In another aspect, the present invention provides an isolated nucleic acid comprising a nucleotide sequence encoding the light chain of an antibody of the invention, the heavy chain of an antibody of the invention, or a polypeptide of the invention.

In another aspect, the present invention provides a vector comprising an isolated nucleic acid of the invention. In another embodiment, said vector is an expression vector.

In another aspect, the present invention provides an isolated cell comprising a nucleic acid of the invention. In one embodiment, said cell is a hybridoma. In another embodiment, said cell is a transgenic cell.

In another aspect, the present invention provides a cell comprising an antibody of the invention. In one embodiment, said cell is a hybridoma. In another embodiment, said cell is a transgenic cell.

In another aspect, the present invention provides a cell comprising a polypeptide of the invention. In one embodiment, said cell is a transgenic cell.

In another aspect, the present invention provides a method of making an antibody of the invention comprising incubating a cell comprising a nucleic acid encoding the light chain of said antibody and a nucleic acid encoding the heavy chain of said antibody under conditions that allow said cell to express said light chain and said heavy chain and that allow said light chain and said heavy chain to assemble into said antibody, and isolating said antibody from said cell. In one embodiment, said cell is a hybridoma. In another embodiment, said cell is a transgenic cell.

In another aspect, the present invention provides a method of inhibiting an IL-4 receptor comprising contacting a cell expressing IL-4 receptor alpha with an antibody of the invention or a polypeptide of the invention under conditions that allow said antibody or said polypeptide to bind to said IL-4 receptor alpha. In one embodiment, said cell is a human cell. In another embodiment, said human cell is in a human.

In another aspect, the present invention provides a method of treating a condition in a subject comprising administering to said subject an amount of an antibody of the invention or of a polypeptide of the invention effective for treating said condition. In one embodiment, said condition is an inflammatory or cancerous condition. In another embodiment, said inflammatory or cancerous condition is an immunological condition. In another embodiment, said condition is asthma, septic arthritis, dermatitis herpetiformis, chronic idiopathic urticaria, ulcerative colitis, scleroderma, hypertrophic scarring, Whipple's Disease, benign prostate hyperplasia, a lung disorder in which IL-4 receptor plays a role, condition in which IL-4 receptor-mediated epithelial barrier disruption plays a role, a disorder of the digestive system in which IL-4 receptor plays a role, an allergic reaction to a medication, Kawasaki disease, sickle cell disease, Churg-Strauss syndrome, Grave's disease, pre-eclampsia, Sjogren's syndrome, autoimmune lymphoproliferative syndrome, autoimmune hemolytic anemia, Barrett's esophagus, autoimmune uveitis, tuberculosis, cyctic fibrosis, allergic bronchopulmonary mycosis, chronic obstructive pulmonary disease, bleomycin-induced pneumopathy and fibrosis, radiation-induced pulmonary fibrosis, pulmonary alveolar proteinosis, adult respiratory distress syndrome, sarcoidosis, hyper IgE syndrome, idiopathic hypereosinophil syndrome, an autoimmune blistering disease, pemphigus vulgaris, bullous pemphigoid, myasthenia gravis, chronic fatigue syndrome, or nephrosis.

In another aspect, the present invention provides a pharmaceutical composition comprising an antibody of the invention or a polypeptide of the invention and an excipient, diluent, or buffer.

BRIEF DESCRIPTION OF THE DRAWINGS

FIGS. 1A-C present the nucleotide sequence of the coding region of a human IL-4 receptor alpha cDNA. The amino acid sequence encoded by the cDNA is presented as well. The cDNA clone was isolated from a cDNA library derived from a human T cell line T22. The encoded protein comprises (from N- to C-terminus) an N-terminal signal peptide, followed by an extracellular domain, a transmembrane region (underlined), and a cytoplasmic domain, as discussed further in PCT publication WO 01/92340 A3. The nucleotide sequence and amino acid sequences of FIGS. 1A to 1C also are presented in SEQ ID NO:1 and 2, respectively.

FIGS. 2A-2D present polynucleotide sequences encoding the light chain variable regions of L1 (SEQ ID NO:3), L2 (SEQ ID NO:5), L3, (SEQ ID NO:7), L4 (SEQ ID NO:9), L5 (SEQ ID NO:11), and L6 (SEQ ID NO:13), and polynucleotide sequences encoding the heavy chain variable regions of H1 (SEQ ID NO:15), H2 (SEQ ID NO:17), H3 (SEQ ID NO:19), H4 (SEQ ID NO:21), H5 (SEQ ID NO:23), H6 (SEQ ID NO:25), H7 (SEQ ID NO:27), H8 (SEQ ID NO:29), H9 (SEQ ID NO:31), H10 (SEQ ID NO:33), H11 (SEQ ID NO:35), H12 (SEQ ID NO:37), H13 (SEQ ID NO:39), H14 (SEQ ID NO:41), H15 (SEQ ID NO:43), H16 (SEQ ID NO:45), H17 (SEQ ID NO:47), H18 (SEQ ID NO:49), H19 (SEQ ID NO:51), H20 (SEQ ID NO:53), H21 (SEQ ID NO:55), H22 (SEQ ID NO:57), H23 (SEQ ID NO:59), and H24 (SEQ ID NO:61). The sequences are shown using one-letter nucleotide abbreviations. Sequences corresponding to CDR1, CDR2, and CDR3 regions are shown in bold type for each sequence and underlined in L1 and H1. Sequences corresponding to FR1, FR2, FR3, and FR4 are shown in plain type.

FIG. 3 presents the amino acid sequences of the light chain variable regions of L1 (SEQ ID NO:4), L2 (SEQ ID NO:6), L3, (SEQ ID NO:8), L4 (SEQ ID NO:10), L5 (SEQ ID NO:12), and L6 (SEQ ID NO:14), and amino acid sequences of the heavy chain variable regions of H1 (SEQ ID NO:16), H2 (SEQ ID NO:18), H3 (SEQ ID NO:20), H4 (SEQ ID NO:22), H5 (SEQ ID NO:24), H6 (SEQ ID NO:26), H7 (SEQ ID NO:28), H8 (SEQ ID NO:30), H9 (SEQ ID NO:32), H10 (SEQ ID NO:34), H11 (SEQ ID NO:36), H12 (SEQ ID NO:38), H13 (SEQ ID NO:40), H14 (SEQ ID NO:42), H15 (SEQ ID NO:44), H16 (SEQ ID NO:46), H17 (SEQ ID NO:48), H18 (SEQ ID NO:50), H19 (SEQ ID NO:52), H20 (SEQ ID NO:54), H21 (SEQ ID NO:56), H22 (SEQ ID NO:58), H23 (SEQ ID NO:60), and H24 (SEQ ID NO:62). The sequences of the L1 and H1 variable regions are shown using one-letter amino acid abbreviations. Other light chain and heavy chain variable sequences are indicated by dashes at residues where they are identical to L1 or H1 and with the appropriate one-letter amino acid abbreviation where they differ from L1 or H1. Sequences corresponding to CDR1, CDR2, and CDR3 regions are shown in bold type for each sequence and underlined in L1 and H1. Sequences corresponding to FR1, FR2, FR3, and FR4 are shown in plain type.

DETAILED DESCRIPTION OF THE INVENTION

The present invention provides compositions and methods relating to anti-IL-4 receptor (IL-4R) antibodies, including methods for treating certain conditions mediated by IL-4R, and for inhibiting biological activities of interleukin-4 (IL-4) and interleukin-13 (IL-13) in vivo. Compositions of the invention include, for example, anti-IL-4R antibodies, polypeptides, polynucleotides, cells comprising or expressing antibodies, polypeptides or polynucleotides of the invention, and pharmaceutical compositions, examples of which are provided below.

Polynucleotide and polypeptide sequences are indicated using standard one- or three-letter abbreviations. Unless otherwise indicated, polypeptide sequences have their amino termini at the left and their carboxy termini at the right and single-stranded nucleic acid sequences, and the top strand of double-stranded nucleic acid sequences, have their 5' termini at the left and their 3' termini at the right. A particular polypeptide or polynucleotide sequence also can be described by explaining how it differs from a reference sequence. For example, the phrase "a polypeptide sequence that differs from SEQ ID NO:4 at S28T" describes a polypeptide sequence that is identical to SEQ ID NO:4 except that the serine residue at position 28 of SEQ ID NO:4 is replaced by a threonine residue.

Polynucleotide and polypeptide sequences of particular light and heavy chain variable regions are shown in FIGS. 2 and 3, respectively, where they are labeled, for example, L1 ("light chain variable region 1"), H1 ("heavy chain variable region 1"), etc. Antibodies comprising a light chain and heavy chain from FIG. 3 are indicated by combining the name of the light chain and the name of the heavy chain variable regions. For example, "L4H7," indicates an antibody comprising the light chain variable sequence of L4 and the heavy chain variable sequence of H7.

"Light chain variable domain (or region)," "heavy chain variable domain (or region)," "CDR1, 2, and 3" and "FR1, 2, 3, and 4" are defined according to the scheme of Kabat et al. in *Sequences of Proteins of Immunological Interest*, 5th Ed., US Dept. of Health and Human Services, PHS, NIH, NIH Publication no. 91-3242, 1991.

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

A biological molecule (e.g., a polypeptide, antibody, or nucleic acid) is "isolated" or "substantially purified" if it is sufficiently free of other biological molecules, cell debris, and other substances to be used in standard laboratory protocols (e.g., a binding or hybridization assay). Methods of substantially purifying polypeptides, antibodies, and nucleic acids are well-known in the art.

The terms "peptide," "polypeptide" and "protein" are used interchangeably throughout and refer to a molecule comprising two or more amino acid residues joined to each other by peptide bonds.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof, of the invention.

Two single-stranded nucleic acid molecules are "the complement" of each other if their sequences can be aligned in an anti-parallel orientation such that every nucleotide in one sequence is opposite its complementary nucleotide in the other sequence, without the introduction of gaps, and without unpaired nucleotides at the 5' or the 3' end of either sequence. A nucleic acid molecule that is "complementary" to a given nucleotide sequence is one that is sufficiently complementary to the given nucleotide sequence that it can hybridize under moderately stringent conditions to the given nucleotide sequence. Thus, a nucleic acid can be complementary to another nucleic acid without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid. The regulatory sequence can, for example, exert its effects directly on the regulated nucleic acid, or through the action of one or more polypeptides (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06.

A "host cell" is a cell that can be used to express a nucleic acid, e.g., a nucleic acid of the invention. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, Cell 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31) or CHO strain DX-B11, which is deficient in DHFR (see Urlaub et al., 1980, Proc. Natl. Acad. Sci. USA 77:4216-20), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric antibody" is an antibody in which a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies, that exhibit the desired biological activity (i.e., the ability to specifically bind IL-4 receptor). See, U.S. Pat. No. 4,816,567 and Morrison, 1985, Science 229:1202-07.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

A "variant" of a polypeptide (e.g., an antibody) comprises an amino acid sequence wherein one or more amino acid residues are inserted into, deleted from and/or substituted into the amino acid sequence relative to another polypeptide sequence. Variants of the invention include fusion proteins.

A "derivative" of a polypeptide is a polypeptide (e.g., an antibody) that has been chemically modified in some manner distinct from insertion, deletion, or substitution variants, e.g., via conjugation to another chemical moiety. Unless otherwise indicated, the term "antibody" includes, in addition to antibodies comprising two full-length heavy chains and two full-length light chains, derivatives, variants, fragments, and muteins thereof, examples of which are described below.

A molecule (e.g., an antibody) "specifically binds IL-4 receptor" if it bind to IL-4 receptor, or a fragment thereof, with at least 10 times higher affinity than the molecule binds to a polypeptide unrelated to IL-4 receptor.

An "antigen binding domain" or "antigen binding region" is the portion of an antibody molecule which contains the amino acid residues (or other moieties) that interact with an antigen and confer on the antibody its specificity and affinity for the antigen.

An "epitope" is the portion of a molecule that is bound by an antibody. An epitope can comprise non-contiguous portions of the molecule (e.g., in a polypeptide, amino acid residues that are not contiguous to one another in the polypeptide's sequence but that, together in the context of the molecule, are bound by an antibody).

Indications

In one aspect, the present invention provides methods of treating, preventing, curing, relieving, or ameliorating a disease, disorder, condition, or illness. Among the conditions to be treated in accordance with the present invention are asthma, septic/reactive arthritis, dermatitis herpetiformis, chronic idiopathic urticaria, scleroderma, hypertrophic scarring, Whipple's Disease, benign prostate hyperplasia, lung disorders in which IL-4 plays a role, conditions in which IL-4-induced epithelial barrier disruption plays a role, disorders of the digestive system in which IL-4 plays a role, including inflammatory bowel disease and other inflammatory conditions in the gastrointestinal tract, allergic reactions to medication, Kawasaki disease, sickle cell disease (including sickle cell crisis), Churg-Strauss syndrome, Grave's disease, pre-eclampsia, Sjogren's syndrome, autoimmune lymphoproliferative syndrome, autoimmune hemolytic anemia, Barrett's esophagus, autoimmune uveitis, tuberculosis, and nephrosis, as described in more detail below. IL-4R antagonists also find use as adjuvants to allergy immunotherapy and as vaccine adjuvants.

Examples of antibodies suitable for treating these conditions are described below, and include, e.g., antibodies that bind IL-4R and inhibit the binding of IL-4 thereto. Particularly useful antibodies also inhibit the binding of IL-13 to IL-13 receptor (IL-13R). Particular embodiments of the invention include novel antibodies and antibody derivatives, fragments, muteins and variants, polypeptides, nucleic acid molecules, cells, methods of making the preceding, methods of inhibiting IL-4Rα, and methods of treating a subject, examples of which are described below.

In one aspect, the present invention provides methods comprising administering an anti-IL-4Rα antibody to a subject. In one embodiment, the subject is afflicted with, or at risk for developing, a condition (including, e.g., an illness, infection, injury, disease, or disorder) that is caused, induced, mediated, potentiated, exacerbated, or otherwise affected, directly or indirectly, by the activity of IL-4Rα. Such conditions include, for example, conditions caused, induced, mediated, potentiated, exacerbated, or otherwise affected, directly or indirectly, by IL-4 and/or IL-13. Other factors or cytokines also may play a role in such conditions.

The biological activities of IL-4 are mediated through binding to specific cell surface receptors, referred to as interleukin-4 receptors (IL-4R). IL-4-induced conditions include those arising from biological responses that result from the binding of IL-4 to a native IL-4 receptor on a cell, or which may be inhibited or suppressed by preventing IL-4 from binding to an IL-4 receptor. Conditions that may be treated include, but are not limited to, medical disorders characterized by abnormal expression of IL-4 or of one or more components of an IL-4R or IL-13R (including, for example, overexpression, misexpression in a particular tissue or cell type, or misexpression at a particular developmental stage), or by an abnormal host response to IL-4 production. Further examples are conditions in which IL-4-induced antibody production, or proliferation or influx of a particular cell type, plays a role. IL-4-induced disorders include those in which IL-4 induces upregulation of IL-4 receptors or enhanced production of another protein that plays a role in a disease (e.g., another cytokine).

A method for treating a mammal, including a human subject, who has such a medical disorder comprises administering an anti-IL-4R antibody, or derivative thereof, to the mammal or otherwise contacting an IL-4R of the mammal with the antibody or derivative, e.g., in an ex vivo procedure. Conditions that may be treated in accordance with the present invention are described, for example, in U.S. Ser. No. 09/847,816, filed May 1, 2001, the relevant disclosure of which is incorporated by reference herein. Such conditions include, but are not limited to, asthma, septic/reactive arthritis, dermatitis herpetiformis, urticaria (especially chronic idiopathic urticaria), ulcers, gastric inflammation, mucosal inflammation, ulcerative colitis, Crohn's Disease, inflammatory bowel disease, other disorders of the digestive system in which IL-4 plays a role (e.g., IL-4-induced inflammation of part of the gastrointestinal tract), conditions in which IL-4-induced barrier disruption plays a role (e.g., conditions characterized by decreased epithelial barrier function in the lung or gastrointestinal tract), scleroderma, hypertrophic scarring, Whipple's Disease, benign prostate hyperplasia, IL-4-induced pulmonary conditions (including those listed below), allergic reactions to medication, Kawasaki disease, sickle cell disease or crisis, Churg-Strauss syndrome, Grave's disease, pre-eclampsia, Sjogren's syndrome, autoimmune lymphoproliferative syndrome, autoimmune hemolytic anemia, Barrett's esophagus, autoimmune uveitis, tuberculosis, nephrosis, pemphigus vulgaris or bullous pemphigoid (autoimmune blistering diseases), and myasthenia gravis (an autoimmune muscular disease).

Anti-IL-4R antibodies, and derivatives thereof, also find use as adjuvants to allergy immunotherapy and as vaccine adjuvants. Accordingly, an anti-IL-4R antibody may be employed as an adjuvant to allergy immunotherapy treatment. Anti-IL-4R antibody find further use as vaccine adjuvants, such as adjuvants for cancer vaccines and infectious disease vaccines. The use of IL-4 adjuvants, especially when directing the immune response toward a TH1 response would be beneficial in treating or preventing the disease in question.

Septic/Reactive Arthritis

An anti-IL-4R antibody may be employed in treating septic arthritis, which also is known as reactive arthritis or bacterial arthritis. Septic arthritis can be triggered by (result from, or develop subsequent to) infection with such microbes as *Staphylococcus aureus, Chlamydia trachomatis, Yersinia* e.g., *Y. enterocolitica, Salmonella*, e.g., *S. enteritidis, Shigella* and *Campylobacter. S. aureus* has been reported to be the major human pathogen in septic arthritis, responsible for the majority of cases.

IL-4 and IL-4-dependent Th2 responses play roles in promoting septic arthritis. Anti-IL-4R antibody can be employed in accordance with the invention to inhibit IL-4 and also to suppress the Th2 response in patients having septic arthritis or at risk for developing septic arthritis.

IL-4 increases bacterial burden and bacterial persistence in joints, by inhibiting clearance of the bacteria. Anti-IL-4R antibody may be employed to assist in the clearance of bacteria associated with reactive arthritis, thereby reducing clinical manifestations such as swelling in joints. Anti-IL-4R antibody may be administered to a human subject afflicted with septic arthritis, to reduce IL-4-mediated joint inflammation. In one approach, an antagonist is injected into a joint, e.g., into synovial fluid in the knee.

The use of an anti-IL-4R antibody may benefit subjects having (or at risk for) septic arthritis by suppressing a TH2 response and promoting a TH1 response against the infection. TH2 cytokines may contribute to bacterial persistence in the joint, whereas a TH1 response plays a role in eliminating the bacteria.

The antibody may be administered to subjects infected with bacteria or other microbes such as those listed above, to prevent development of septic arthritis. An Antibody may be administered, for example, after diagnosis with such an infection, but before development of clinical symptoms of septic arthritis.

Whipple's Disease

*Tropheryma whippelii* is the causative bacterium for Whipple's Disease, also known as intestinal lipodystrophy and lipophagia granulomatosis. The disease is characterized by steatorrhea, frequently generalized lymphadenopathy, arthritis, fever, and cough. Also reported in Whipple's Disease patients are an abundance of "foamy" macrophages in the jejunal lamina propria, and lymph nodes containing periodic acid-schiff positive particles appearing bacilliform by electron microscopy (*Steadman's Medical Dictionary*, 26$^{th}$ Edition, Williams & Wilkins, Baltimore, Md., 1995).

The use of anti-IL-4R antibody may benefit subjects having (or at risk for developing) Whipple's Disease, by restoring a normal balance between the TH1 and TH2 components of the patient's immune response. Increased production of IL-4 (a TH2-type cytokine) and decreased levels of certain TH1-type cytokines have been associated with Whipple's Disease. TH2 cytokines may contribute to bacterial persistence, whereas a TH1 response plays a role in clearing the causative bacteria. IL-4R antagonists may be administered to subjects infected with *T. whippelii*, whether or not the subject exhibits clinical symptoms of Whipple's Disease.

Dermatitis Herpetiformis

Dermatitis herpetiformis, also known as Duhring's disease, is a chronic skin condition characterized by blistering skin lesions, cutaneous IgA deposits, and itching. Patients have an immunobullous skin disorder with an associated gluten sensitive enteropathy, which is mediated by a Th2 immune response. Anti-IL-4R antibody is administered in accordance with the present invention, to inhibit IL-4 and the Th2 response, thus promoting healing of current lesions and reducing or preventing the formation of blisters on the extensor body surfaces.

Hypertrophic Scarring

In accordance with the present invention, anti-IL-4R antibody is administered to subjects who have, or are susceptible to developing, hypertrophic scarring. In one method provided herein, an anti-IL-4R antibody is administered to a subject with a burn injury. An immune response to burns and other injury is believed to play a role in the pathogenesis of hypertrophic scarring. Increased production of TH2-type cytokines, including IL-4, and reduced levels of certain TH1-type cytokines have been reported in burn patients who have hypertropic scarring. The use of anti-IL-4R antibodies may benefit subjects having (or at risk for developing) hypertrophic scarring, by suppressing a TH2-type immune response.

Urticaria

Urticaria, especially chronic forms thereof such as chronic idiopathic urticaria (CIU), may be treated with an anti-IL-4R antibody in accordance with the present invention. CIU patients have higher serum levels of IL-4 than controls, and may have a predominantly TH2-type cytokine profile. Mast cells and Th2-type T cells are implicated as primary effector cells in chronic urticaria. IL-4 stimulates mast cell proliferation. Mast cell degranulation leads to histamine release, subsequent erythema, eosinophilia, redness of skin, and itching. Anti-IL-4R antibodies are administered to inhibit IL-4 and reduce the TH2-type response, thereby helping to control a subject's urticaria.

Ulcerative Colitis; Other Disorders of the Gastrointestinal Tract

IL-4 is implicated in the pathogenesis of ulcerative colitis. Th2-type cytokines including IL-4 may predominate in the colonic mucosa of patients with this disorder. The use of anti-IL-4R antibodies to suppress the TH2 response may alleviate this condition.

In addition to ulcerative colitis, other disorders of the gastrointestinal tract or digestive system may be treated with anti-IL-4R antibodies. Examples of such disorders include, but are not limited to, inflammatory bowel disease (IBD), with ulcerative colitis and Crohn's Disease being forms of IBD, gastritis, ulcers, and mucosal inflammation.

Any gastrointestinal condition in which IL-4 plays a role may be treated with an anti-IL-4R antibody in accordance with the present invention. For example, conditions involving IL-4-induced inflammation of part of the gastrointestinal tract may be treated with an anti-IL-4R antibody. Particular embodiments are directed to treatment of chronic inflammatory conditions in the gastrointestinal tract.

Other embodiments are directed to conditions in which IL-4-induced barrier disruption plays a role, e.g., conditions characterized by decreased epithelial barrier function in at least a portion of the gastrointestinal tract. Such conditions may, for example, involve damage to the epithelium that is induced by IL-4, directly or indirectly.

The intestinal epithelium forms a relatively impermeable barrier between the lumen and the submucosa. Disruption of the epithelial barrier has been associated with conditions such as inflammatory bowel disease. See the discussion in Youakim, A. and M. Ahdieh (*Am. J. Physiol.* 276 (*Gastrointest. Liver Physiol.* 39):G1279-G1288, 1999), hereby incorporated by reference in its entirety. A damaged or "leaky" barrier can allow antigens to cross the barrier, which in turn elicits an immune response that may cause further damage to gastrointestinal tissue. Such an immune response may include recruitment of neutrophils or T cells, for example. An anti-IL-4R antibody may be administered to inhibit undesirable stimulation of an immune response.

Lung Disorders

Methods for treating IL-4-induced pulmonary disorders are provided herein. Such disorders include, but are not limited to, lung fibrosis, including chronic fibrotic lung disease, other conditions characterized by IL-4-induced fibroblast proliferation or collagen accumulation in the lungs, pulmonary conditions in which a TH2-type immune response plays a role, conditions characterized by decreased barrier function in the lung (e.g., resulting from IL-4-induced damage to the epithelium), or conditions in which IL-4 plays a role in an inflammatory response (e.g., asthma).

Cystic fibrosis is characterized by the overproduction of mucus and development of chronic infections. Inhibiting IL-4 and the Th2 response will reduce mucus production and help control infections such as allergic bronchopulmonary aspergillosis (ABPA).

Allergic bronchopulmonary mycosis occurs primarily in patients with cystic fibrosis or asthma, where a Th2 immune response is dominant. Inhibiting IL-4 and the Th2 response will help clear and control these infections.

Chronic obstructive pulmonary disease is associated with mucus hypersecretion and fibrosis. Inhibiting IL-4 and the Th2 response will reduce the production of mucus and the development of fibrous thereby improving respiratory function and delaying disease progression.

Bleomycin-induced pneumopathy and fibrosis, and radiation-induced pulmonary fibrosis are disorders characterized by fibrosis of the lung which is manifested by the influx of Th2, CD4+ cells and macrophages, which produce IL-4 which in turn mediates the development of fibrosis. Inhibiting IL-4 and the Th2 response will reduce or prevent the development of these disorders.

Pulmonary alveolar proteinosis is characterized by the disruption of surfactant clearance. IL-4 increases surfactant product. Use of anti-IL-4R antibody will decrease surfactant production and decrease the need for whole lung lavage.

Adult respiratory distress syndrome (ARDS) may be attributable to a number of factors, one of which is exposure to toxic chemicals. One patient population susceptible to ARDS is critically ill patients who go on ventilators. ARDS is a frequent complication in such patients. Anti-IL-4R antibody treatment may alleviate ARDS by reducing inflammation and adhesion molecules, although methods for treating such subjects in accordance with the present invention are not limited by a particular mechanism of action. Anti-IL-4R antibody may be used to prevent or treat ARDS.

Sarcoidosis is characterized by granulomatus lesions. Use of anti-IL-4R antibody to treat sarcoidosis, particularly pulmonary sarcoidosis, is contemplated herein.

Conditions in which IL-4-induced barrier disruption plays a role (e.g., conditions characterized by decreased epithelial barrier function in the lung) may be treated with anti-IL-4R antibody. Damage to the epithelial barrier in the lungs may be induced by IL-4 directly or indirectly. The epithelium in the lung functions as a selective barrier that prevents contents of the lung lumen from entering the submucosa. A damaged or "leaky" barrier allows antigens to cross the barrier, which in turn elicits an immune response that may cause further damage to lung tissue. Such an immune response may include recruitment of eosinophils or mast cells, for example. An anti-IL-4R antibody may be administered to inhibit such undesirable stimulation of an immune response.

Anti-IL-4R antibodies may be employed to promote healing of lung epithelium, thus restoring barrier function. Anti-IL-4R antibody may be employed to promote healing of lung epithelium in asthmatics, for example. Alternatively, the antagonist is administered for prophylactic purposes, to prevent IL-4-induced damage to lung epithelium.

Tuberculosis

A TH2-type immune response is implicated in playing a role in causing tissue damage (e.g., necrosis of lung tissue) in tuberculosis (TB) patients. Elevated levels of IL-4 are associated with TB. IL-4 production may be particularly elevated in cavitary tuberculosis (i.e., in TB patients who have developed pulmonary cavities, which can be detected/visualized by such techniques as radiographs of the chest).

Anti-IL-4R antibodies may benefit TB patients (especially those with cavitary TB) by suppressing a TH2-type immune response. Methods for treating such subjects in accordance with the present invention are not limited by a particular mechanism of action, however. Anti-IL-4R antibody advantageously are administered in an amount that restores the desired balance between the TH1 and TH2 components of the immune response, and reduces IL-4-induced tissue damage in a patient.

Chum-Strauss Syndrome

Churg-Strauss syndrome, a disease also known as allergic granulomatous angiitis, is characterized by inflammation of the blood vessels in persons with a history of asthma or allergy, and by eosinophilia. Anti-IL-4R antibodies may be administered to alleviate inflammation in subjects with this syndrome. The use of anti-IL-4R antibodies to suppress a TH2-type immune response, and to combat eosinophilia, would benefit the subjects.

Pre-Eclampsia

Pre-eclampsia is a toxemia of late pregnancy. The condition is characterized by a sharp rise in blood pressure, generally accompanied by edema and albuminuria, during the third term of pregnancy.

Elevated TH1-type and TH2-type immune responses may play a role in the condition. One method provided herein comprises administering an anti-IL-4R antibody to a pregnant woman who has developed pre-eclampsia. The anti-IL-4R antibody is administered in an amount, and for a period of time, sufficient to reduce the level of IL-4 (or of TH2-type cytokines collectively) to a level that is considered normal during pregnancy. In general, the anti-IL-4R antibody is administered repeatedly throughout the duration of the pregnancy.

Scleroderma

Anti-IL-4R antibodies are administered to subjects with scleroderma in accordance with the invention. The antibodies reduce IL-4-induced collagen synthesis by fibroblasts in the patients. The antibodies may be employed in preventing or reducing fibrosis in skin and lung tissues, as well as other tissues in which fibrosis occurs in scleroderma patients, suppressing collagen synthesis in such tissues, and in treating scleroderma-related pulmonary disease.

Benign Prostate Hyperplasia

Benign prostate hyperplasia (BPH), also known as benign prostate hypertrophy, may be treated with anti-IL-4R antibodies. While not wishing to be bound by a particular mechanism of action, administration of an anti-IL-4R antibody may benefit a subject with BPH by suppressing IL-4-induced inflammation, or by suppressing a TH2-type immune response.

Grave's Disease

Antibodies directed against thyrotropin receptor play an important role in Grave's Disease, a disorder characterized by hyperthyroidism. Studies of cytokine production in Grave's Disease patients show a shift toward a TH2-type cytokine response. Use of an anti-IL-4R antibody to suppress the TH2-type immune response, and suppress antibody production, would benefit Grave's Disease patients.

Sickle Cell Disease

Sickle cell disease patients typically experience intermittent periods of acute exacerbation called crises, with the crises being categorized as anemic or vaso-occlusive. Anti-IL-4R antibodies find use in treating or preventing sickle cell crisis, especially in subjects with elevated IL-4 levels or in whom the immune response has shifted toward a TH2-type response. Sickle cell disease (especially sickle cell crisis) has been associated with increased susceptibility to infectious diseases, including bacterial infections. Administering anti-IL-4R antibodies to sickle cell disease patients may help the patient mount an immune response against infectious diseases.

Sjogren's Syndrome

The autoimmune disease known as Sjogren's syndrome or sicca syndrome typically combines dry eyes and dry mouth with a disorder of the connective tissues, such as rheumatoid arthritis, lupus, scleroderma, or polymyositis. The vast majority of patients are middle age (or older) females. Sjogren's syndrome is an inflammatory disease of glands (e.g., lacrimal and salivary glands) and other tissues of the body. The syndrome typically is associated with autoantibody production.

Anti-IL-4R antibodies may be administered to reduce the inflammatory response (such as inflammation of glands, including lacrimal glands) in such subjects. Anti-IL-4R antibodies may benefit Sjogren's syndrome patients by suppressing a TH2-type immune response. Methods for treating subjects in accordance with the present invention are not limited by a particular mechanism of action, however.

Autoimmune Lymphoproliferative Syndrome

Manifestations of autoimmune lymphoproliferative syndrome include lymphoproliferation and autoantibody production. Patients with the syndrome reportedly have an inherited deficiency in apoptosis. Anti-IL-4R antibodies may benefit subjects with this syndrome by suppressing a TH2-type immune response. Methods for treating such subjects in accordance with the present invention are not limited by a particular mechanism of action, however.

Autoimmune Hemolytic Anemia

Excessive IL-4 secretion, and a deficiency in TH1-type cytokines, are implicated in contributing to the pathogenesis of autoimmune hemolytic anemia. Anti-IL-4R antibodies are administered in accordance with the present invention, to benefit the patients by reducing autoantibody production, and by restoring a more normal balance between the TH1 and TH2 components of the immune response.

Autoimmune Uveitis

Uveitis involves inflammation of the uvea (generally considered to include the iris, ciliary body, and choroid, considered together). Excess IL-4 secretion is implicated as playing a role in pathogenesis of this sight-threatening inflammatory eye disease. In accordance with the present invention, anti-IL-4R antibodies are administered to a subject with, or at risk for developing, uveitis. In one embodiment, anti-IL-4R antibodies are administered to an individual who has autoimmune uveoretinitis.

Kawasaki Disease

Also known as the mucocutaneous lymph node syndrome, Kawasaki disease (KD) mainly afflicts young children. The disease is characterized by particular changes in the mucus membranes lining the lips and mouth, and by enlarged, tender lymph glands. Symptoms typically include fever, conjunctivitis, inflammation of the lips and mucous membranes of the mouth, swollen glands in the neck, and a rash covering the hands and feet, leading to hardened, swollen and peeling skin on hands and feet. In children with Kawasaki Disease (KD), inflammation of arteries (vasculitis) may develop. Due to the effect of the disease on the vascular system, KD reportedly is the main cause of acquired heart disease in children.

Anti-IL-4R antibodies may be administered to subjects with Kawasaki Disease. Excessive IL-4 secretion and a deficiency in TH1-type cytokines contribute to the pathogenesis of the disease.

Barrett's Esophagus

Barrett's esophagus is a condition characterized by alteration (subsequent to irritation) of the cells in the epithelial tissue that lines the lower portion of the esophagus. Frequent reflux of the stomach contents into the esophagus, over time, can lead to Barrett esophagus. Patients with Barrett esophagus are at risk for developing esophageal cancer (e.g., adenocarcinoma). While not wishing to be bound by a particular mechanism of action, administration of an anti-IL-4R antibody may benefit a subject with Barrett's esophagus by suppressing a TH2-type immune response. In one embodiment, an anti-IL-4R antibody is administered to a subject with esophagitis, to inhibit progression to Barrett's esophagus.

Nephrosis

Nephrosis, also known as nephrotic syndrome, is a kidney disease that is non-inflammatory and non-malignant. In the condition known as minimal change nephrosis, glomerular damage (believed to arise from structural changes in glomerular visceral epithelial cells) results in abnormalities that include proteinuria. A TH2-type immune response (especially secretion of the TH2-type cytokines IL-4 and IL-13) are implicated as playing a role in pathogenesis of minimal change nephrosis.

Other Indications

Additional examples of conditions that may be treated in accordance with the present invention include but are not limited to the following. Anti-IL-4R antibodies may be employed in treating or preventing hyper IgE syndrome, idiopathic hypereosinophil syndrome, allergic reactions to medication, autoimmune blistering diseases (e.g., pemphigus vulgaris or bullous pemphigoid), myasthenia gravis (an autoimmune muscular disease), and chronic fatigue syndrome. Anti-IL-4R antibodies may be employed in treating GVHD; particular methods for treating GVHD in combination with other therapeutic agents are described below. Anti-IL-4R antibodies also find use in treating or preventing hepatotoxicity induced by drugs such as diclofenac (a non-steroidal anti-inflammatory drug).

An anti-IL-4R antibody may be employed as an adjuvant to allergy immunotherapy treatment. Anti-IL-4R antibodies find further use as vaccine adjuvants, such as adjuvants for cancer vaccines and infectious disease vaccines. The use of anti-IL-4R antibodies is especially advantageous when favoring a TH1-type immune response would be beneficial in preventing or treating the condition for which the vaccine is being administered. Anti-IL-4R antibodies may be employed when reducing an antibody-mediated immune response and/or promoting a T-cell-mediated immune response is desired.

Anti-IL-4R Antibodies

In one aspect, the present invention provides antibodies, and fragments, derivatives, muteins, and variants thereof, which bind to IL-4 receptor alpha, e.g., human IL-4 receptor alpha.

Anti-IL-4R antibodies that may be employed in accordance with the present invention include antibodies that inhibit a biological activity of IL-4. Examples of such biological activities include associating with another receptor component (e.g., IL-2R gamma or IL-13R alpha), binding (either alone or as part of a multimeric receptor complex) a signaling molecule (e.g., IL-4 or IL-13), and transducing a signal in response to binding a signaling molecule.

Different anti-IL-4R antibodies may bind to different domains or epitopes of IL-4R or act by different mechanisms of action. Examples include but are not limited to antibodies that interfere with binding of IL-4 to IL-4R or that inhibit signal transduction. The site of action may be, for example, intracellular (e.g., by interfering with an intracellular signaling cascade) or extracellular. An antibody need not completely inhibit an IL-4 induced activity to find use in the present invention; rather, antibodies that reduce a particular activity of IL-4 are contemplated for use as well.

The above-presented discussions of particular mechanisms of action for anti-IL-4R antibodies in treating particular diseases are illustrative only, and the methods presented herein are not bound thereby. The mechanisms of action by which anti-IL-4R antibodies ameliorate diseases are not limited to those discussed above.

An anti-IL-4R antibody may inhibit an IL-4-mediated influx of cells involved in an immune or inflammatory response. An antibody may act by, for example, reducing proliferation, activation, migration, influx, or accumulation of a particular cell type, or by inhibiting a biological response directly or indirectly attributable to a particular cell type. Examples of particular cell types are fibroblasts, mast cells, and eosinophils.

As discussed above, some conditions may be treated by suppressing a TH2-type immune response. IL-4R is associated with a TH2 response, and is one of the cytokines secreted by T-helper cells of type 2 (TH2 cells). An anti-IL-4R antibody may be administered to reduce a TH2-type immune response. The IL-4R antibody may be said to reduce proliferation of TH2 cells, to suppress a TH2 response, to shift the immune response toward a TH1 response, or to favor a TH1-type response. Antagonists of other TH2-type cytokine(s), such as IL-5, IL-10, or IL-13, may be additionally administered to subjects who have a disorder involving elevated levels of such cytokines. Techniques for measuring the amount of such cytokines in a subject, e.g., in the subject's serum, are well known.

One embodiment of the invention is directed to a method for inhibiting IL-4-induced damage to epithelium, comprising administering an anti-IL-4R antibody to a subject who has, or is at risk of developing, a condition in which IL-4-mediated epithelial barrier disruption plays a role.

Particular embodiments of methods provided herein comprise administering an anti-IL-4R antibody to inhibit IL-4-induced damage to epithelium in the gastrointestinal tract or lung. Such methods may be employed to prevent epithelial damage, or to restore epithelial barrier function (i.e., promote repair or healing of the epithelium). The ability of an anti-IL-4R antibody to inhibit IL-4-induced damage to epithelium may be confirmed in any of a number of suitable assays, such as those described herein.

Any inflammation associated with (or subsequent to) an infection also may be treated with an anti-IL-4R antibody. The antibody may be administered to inhibit any IL-4-induced component of an inflammatory response resulting from microbial infection in the gastrointestinal tract, for example.

Combinations of two or more antibodies or antibody derivatives, or of an antibody or antibody derivative and one or more other IL-4, IL-13, IL-4R and/or IL-13R antagonists (as described, for example, in U.S. Pat. Nos. 5,599,905, 5,840,869, 5,856,296, 5,767,065, 5,717,072, 6,391,581, 5,710,023, Idzerda et al., 1990, J. Exp. Med. 171:861-73, and Mosley et al., 1989, Cell 59:335-48, incorporated herein by reference in their entireties) may be employed in methods and compositions of the present invention.

Oligonucleotide-directed site-specific mutagenesis procedures can be employed to provide an altered gene having particular codons altered according to the substitution, deletion, or insertion required. Examples of techniques for making such alterations are described in Walder et al., 1986, Gene 42:133; Bauer et a/0.1985, Gene 37:73; Craik, BioTechniques, January 1985, 12-19; Smith et al., 1981, *Genetic Engineering: Principles and Methods*, Plenum Press; and U.S. Pat. Nos. 4,518,584 and 4,737,462. These and other methods can be used to make, for example, derivatives of anti-IL-4R antibodies that have, for example, increased affinity, avidity, or specificity for IL-4R as compared to the underivatized antibody.

Other derivatives of anti-IL-4R antibodies within the scope of this invention include covalent or aggregative conjugates of anti-IL-4R antibodies, or fragments thereof, with other proteins or polypeptides, such as by expression of recombinant fusion proteins comprising heterologous polypeptides fused to the N-terminus or C-terminus of an anti-IL-4R antibody polypeptide. For example, the conjugated peptide may be a heterologous signal (or leader) polypeptide, e.g., the yeast alpha-factor leader, or a peptide such as an epitope tag. Anti-IL-4R antibody-containing fusion proteins can comprise peptides added to facilitate purification or identification of the anti-IL-4R antibody (e.g., poly-His). An anti-IL-4R antibody polypeptide also can be linked to the FLAG peptide Asp-Tyr-Lys-Asp-Asp-Asp-Asp-Lys (DYKDDDDK) (SEQ ID NO:69) as described in Hopp et al., *Bio/Technology* 6:1204, 1988, and U.S. Pat. No. 5,011,912. The FLAG peptide is highly antigenic and provides an epitope reversibly bound by a specific monoclonal antibody (mAb), enabling rapid assay and facile purification of expressed recombinant protein. Reagents useful for preparing fusion proteins in which the FLAG peptide is fused to a given polypeptide are commercially available (Sigma, St. Louis, Mo.).

Oligomers that contain one or more anti-IL-4R antibody polypeptides may be employed as IL-4R antagonists. Oligomers may be in the form of covalently-linked or non-covalently-linked dimers, trimers, or higher oligomers. Oligomers comprising two or more anti-IL-4R antibody polypeptides are contemplated for use, with one example being a homodimer. Other oligomers include heterodimers, heterotrimers, etc.

One embodiment is directed to oligomers comprising multiple anti-IL-4R antibody polypeptides joined via covalent or non-covalent interactions between peptide moieties fused to the anti-IL-4R antibody polypeptides. Such peptides may be peptide linkers (spacers), or peptides that have the property of promoting oligomerization. Leucine zippers and certain polypeptides derived from antibodies are among the peptides that can promote oligomerization of IL-4R polypeptides attached thereto, as described in more detail below.

In particular embodiments, the oligomers comprise from two to four anti-IL-4R antibody polypeptides. The anti-IL-4R antibody moieties of the oligomer may be in any of the forms described above, e.g., variants or fragments. Preferably, the oligomers comprise anti-IL-4R antibody polypeptides that have IL-4R binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 "Construction of Immunoglobulin Fusion Proteins", in *Current Protocols in Immunology*, Suppl. 4, pages 10.19.1-10.19.11.

One embodiment of the present invention is directed to a dimer comprising two fusion proteins created by fusing an IL-4R binding fragment of an anti-IL-4R antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization are also included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of an anti-IL-4R antibody may be substituted for the variable portion of an antibody heavy and/or light chain.

Alternatively, the oligomer is a fusion protein comprising multiple anti-IL-4R antibody polypeptides, with or without peptide linkers (spacer peptides). Among the suitable peptide linkers are those described in U.S. Pat. Nos. 4,751,180 and 4,935,233.

Another method for preparing oligomeric anti-IL-4R antibody derivatives involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191, hereby incorporated by reference. The use of a modified leucine zipper that allows for stable trimerization of a heterologous protein fused thereto is described in Fanslow et al., 1994, Semin. Immunol. 6:267-78. In one approach, recombinant fusion proteins comprising an anti-IL-4R antibody fragment or derivative fused to a leucine zipper peptide are expressed in suitable host cells, and the soluble oligomeric anti-IL-4R antibody fragments or derivatives that form are recovered from the culture supernatant.

Anti-IL-4R antibody polypeptides and fusion proteins described herein may be prepared by any of a number of conventional techniques. For example, anti-IL-4R antibody polypeptides may be purified from cells that naturally express them, or they may be produced in recombinant expression systems, using any technique known in the art.

Any expression system known in the art can be used to make the recombinant polypeptides of the invention. In general, host cells are transformed with a recombinant expression vector that comprises DNA encoding a desired anti-IL-4R antibody polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CVI/EBNA cell line derived from the African green monkey kidney cell line CVI (ATCC CCL 70) as described by McMahan et al., 1991, EMBO J. 10: 2821. Appropriate cloning and expression vectors for use with bacterial, fungal, yeast, and mammalian cellular hosts are described by Pouwels et al. (*Cloning Vectors: A Laboratory Manual*, Elsevier, N.Y., 1985).

The transformed cells are cultured under conditions that promote expression of the anti-IL-4R antibody polypeptide, and the polypeptide is recovered by conventional protein purification procedures. One such purification procedure includes the use of affinity chromatography, e.g., over a matrix having all or a portion (e.g., the extracellular domain) of IL-4R bound thereto. Polypeptides contemplated for use herein include substantially homogeneous recombinant mammalian anti-IL-4R antibody polypeptides substantially free of contaminating endogenous materials.

In one aspect, the present invention provides antibodies that interfere with the binding of IL-4 to an IL-4 receptor. Such antibodies, referred to herein as blocking antibodies, may be raised against IL-4R, or a fragment, variant or derivative thereof, and screened in conventional assays for the ability to interfere with binding of IL-4 to IL-4 receptors. Examples of suitable assays are assays that test the antibodies for the ability to inhibit binding of IL-4 to cells expressing IL-4R, or that test antibodies for the ability to reduce a biological or cellular response that results from the binding of IL-4 to cell surface IL-4 receptors.

It has been reported that IL-4R alpha is a component of certain multi-subunit IL-13 receptor complexes (Zurawski et al., 1995, J. Biol. Chem. 270: 13869; de Vries, 1998, J. Allergy Clin. Immunol. 102:165; and Callard et al., 1996, Immunology Today, 17:108, each incorporated by reference herein). Accordingly, in one embodiment, an antibody is provided that blocks binding of IL-4 and also of IL-13 to cells. The antibodies inhibit IL-4-induced biological activity and also inhibit IL-13-induced activity, and thus may be employed in treating conditions induced by either or both cytokines. Examples of such conditions include but are not limited to IgE-mediated conditions, asthma, allergic conditions, allergic rhinitis, and dermatitis including atopic dermatitis.

Antibodies that bind to IL-4R alpha may be screened in various conventional assays to determine whether they interfere with the binding of IL-13 to IL-4R alpha-containing IL-13 receptor complexes. Antibodies may be screened, for example, in binding assays or tested for the ability to inhibit an IL-IL-13-induced biological activity. An example of a suitable assay is illustrated in Example 2 below.

Antibodies specific for IL-4R alpha may be prepared using any technique known in the art. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988).

Antigen-binding fragments of antibodies of the invention may be produced by conventional techniques. Examples of such fragments include, but are not limited to, Fab and F(ab')$_2$ fragments. Antibody fragments and derivatives produced by genetic engineering techniques are also contemplated. Unless otherwise specified, the terms "antibody" and "monoclonal antibody" as used herein encompass both whole antibodies and antigen-binding fragments and/or derivatives thereof.

Additional embodiments include chimeric antibodies, e.g., humanized versions of murine monoclonal antibodies. Such humanized antibodies may be prepared by known techniques, and offer the advantage of reduced immunogenicity when the antibodies are administered to humans. In one embodiment, a humanized monoclonal antibody comprises the variable domain of a murine antibody (or all or part of the antigen binding site thereof) and a constant domain derived from a human antibody. Alternatively, a humanized antibody fragment may comprise the antigen binding site of a murine monoclonal antibody and a variable domain fragment (lacking the antigen-binding site) derived from a human antibody. Procedures for the production of chimeric and further engineered monoclonal antibodies include those described in Riechmann et al., 1988, Nature 332:323, Liu et al., 1987, Proc. Nat. Acad. Sci. USA 84:3439, Larrick et al., 1989, Bio/Technology 7:934, and Winter et al., 1993, TIPS 14:139. In one embodiment, the chimeric antibody is a CDR grafted antibody.

Procedures have been developed for generating human or partially human antibodies in non-human animals. For example, mice in which one or more endogenous immunoglobulin genes have been inactivated by various means have been prepared. Human immunoglobulin genes have been introduced into the mice to replace the inactivated mouse genes. Antibodies produced in the animal incorporate human immunoglobulin polypeptide chains encoded by the human genetic material introduced into the animal. In one embodiment, a non-human animal, such as a transgenic mouse, is immunized with an IL-4R polypeptide, such that antibodies directed against the IL-4R polypeptide are generated in said animal. One example of a suitable immunogen is a soluble human IL-4R, such as a polypeptide comprising the extracellular domain of the protein of SEQ ID NO:2, or other immunogenic fragment of the protein of SEQ ID NO:2.

Examples of techniques for production and use of transgenic animals for the production of human or partially human antibodies are described in U.S. Pat. Nos. 5,814,318, 5,569, 825, and 5,545,806, which are incorporated by reference herein.

In another aspect, the present invention provides monoclonal antibodies that bind to IL-4 receptor. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In one embodiment, a hybridoma cell line is produced by immunizing an animal (e.g., a transgenic animal having human immunoglobulin sequences) with an IL-4R immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds an IL-4R polypeptide. Such hybridoma cell lines, and anti-IL-4R monoclonal antibodies produced therefrom, are encompassed by the present invention.

Monoclonal antibodies secreted by a hybridoma cell line can be purified using any technique known in the art. Hybridomas or mAbs may be further screened to identify mAbs with particular properties, such as the ability to block an IL-4- and/or an IL-13-induced activity. Example of such screens are provided in Examples 2, 3, and 4.

Further examples of procedures for preparing antibodies directed against human IL-4 (including monoclonal antibodies), assays by which blocking antibodies are identified, and techniques for generating humanized or genetically engineered derivatives of anti-IL-4 antibodies, are described in U.S. Pat. Nos. 5,041,381, 5,863,537, 5,928,904, and 5,676, 940, which are hereby incorporated by reference. Further examples of antibodies that may be employed as IL-4 antagonists are described in WO 91/09059, also incorporated by reference herein.

In another aspect, the present invention provides human antibodies that bind IL-4R. In one embodiment of the invention, human antibodies raised against IL-4R alpha and produced by techniques involving use of transgenic mice, block binding of IL-4 and also IL-13 to cells. Such antibodies are IL-4 antagonists and additionally function as IL-13 antagonists.

Antibodies of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutein of a naturally occurring constant region.

Antibodies directed against an IL-4R can be used, for example, in assays to detect the presence of IL-4R polypeptides, either in vitro or in vivo. The antibodies also may be employed in purifying IL-4R proteins by immunoaffinity chromatography. Those antibodies that additionally can block binding of IL-4 to IL-4R may be used to inhibit a biological activity that results from such binding. Blocking antibodies find use in the methods of the present invention. Such antibodies which function as IL-4 antagonists may be employed in treating any IL-4-induced condition, including but not limited to asthma and allergies, e.g., allergic rhinitis, contact dermatitis, and atopic dermatitis. In one embodiment, a human anti-IL-4R monoclonal antibody generated by procedures involving immunization of transgenic mice is employed in treating such conditions.

Antibodies may be employed in an in vitro procedure, or administered in vivo to inhibit an IL-4-induced biological activity. Disorders caused or exacerbated (directly or indirectly) by the interaction of IL-4 with cell surface IL-4 receptors, examples of which are provided above, thus may be treated. In one embodiment, the present invention provides a therapeutic method comprising in vivo administration of an IL-4 and/or IL-13 blocking antibody to a mammal in need thereof in an amount effective for reducing an IL-4- and/or IL-13-induced biological activity.

Antibodies of the invention include, but are not limited to, partially human and fully human monoclonal antibodies that inhibit a biological activity of IL-4 and also inhibit a biological activity of IL-13. One embodiment is directed to a human monoclonal antibody that at least partially blocks binding of IL-4 to a cell, and at least partially blocks binding of IL-13 to a cell. In one embodiment, the antibodies are generated by immunizing a transgenic mouse with an IL-4 receptor immunogen. In another embodiment, the immunogen is a human IL-4 receptor polypeptide. Hybridoma cell lines derived from the thus-immunized mice, wherein the hybridoma secretes a monoclonal antibody that binds IL-4R, also are provided herein.

Although human, partially human, or humanized antibodies will be suitable for many applications, particularly those involving administration of the antibody to a human subject, other types of antibodies will be suitable for other applications. The non-human antibodies of the invention can be, for example, derived from any antibody-producing animal, such as mouse, rat, rabbit, goat, donkey, or non-human primate (such as monkey (e.g., cynomologous or rhesus monkey) or ape (e.g., chimpanzee)). Non-human antibodies of the invention can be used, for example, in in vitro and cell-culture based applications, or any other application where an immune response to the antibody of the invention does not occur or is insignificant, can be prevented, is not a concern, or is desired. In one embodiment, a non-human antibody of the invention is administered to a non-human subject. In another embodiment, the non-human antibody does not elicit an immune response in the non-human subject. In another embodiment, the non-human antibody is from the same species as the non-human subject, e.g., a mouse antibody of the invention is administered to a mouse. An antibody from a particular species can be made by, for example, immunizing an animal of that species with the desired immunogen (e.g., a soluble IL-4 receptor polypeptide) or using an artificial system for generating antibodies of that species (e.g., a bacterial or phage display-based system for generating antibodies of a particular species), or by converting an antibody from one species into an antibody from another species by replacing, e.g., the constant region of the antibody with a constant region from the other species, or by replacing one or more amino acid residues of the antibody so that it more closely resembles the sequence of an antibody from the other species. In one embodiment, the antibody is a chimeric antibody comprising amino acid sequences derived from antibodies from two or more different species.

In another aspect, the present invention provides antibodies that comprise a light chain variable region selected from the group consisting of L1-L6 and/or a heavy chain variable region selected from the group consisting of H1-H24, and fragments, derivatives, muteins, and variants thereof (see FIGS. 2 and 3). Such an antibody can be denoted using the nomenclature "LxHy", wherein x corresponds to the number of the light chain variable region and y corresponds to the number of the heavy chain variable region as they are labeled in FIG. 3. For example, L4H17 refers to an antibody with a light chain variable region comprising the amino acid sequence of L4 and a heavy chain variable region comprising the amino acid sequence of H17, as shown in FIG. 3. FIGS. 2 and 3 also indicate the location of the CDR and framework regions of each of these variable domain sequences. Antibodies of the invention include, for example, L2H1, L3H1, L4H1, L5H1, L1H2, L1H3, L1H4, L1H5, L1H6, L1H7, L1H8, L1H9, L1H10, L1H11, L2H4, L2H12, L2H13, L2H14, L6H1, L2H2, L2H3, L2H6, L2H7, L2H8, L2H9, L2H10, and L2H11. Additional antibody variable sequences, e.g., human antibody variable sequences, also can be used. See, e.g., Sblattero et al., 1998, Immunotechnology 3:271-78, de Haard et al., 1999, J. Biol. Chem. 274:18218-30.

In one embodiment, the present invention provides an antibody comprising a light chain-variable domain comprising a sequence of amino acids that differs from the sequence of L1 only at one or more residues where any one of the sequences of L2-L6 differs from the sequence of L1 (e.g., said sequence of said antibody differs from the sequence of L1 at residue(s) 1, 4, 7 etc.). In another embodiment, said sequence of said light chain-variable domain comprises at least one amino acid residue of any of the sequence of any one of L2-L6 at a position where it differs from the sequence of L1 (e.g., said sequence comprises the residue(s) E1D, L4M, S7T, etc.). In another embodiment, said sequence differs from the sequence of L1 in at least one CDR (e.g., CDR1, CDR2, or CDR3). In another embodiment, said sequence differs from the sequence of L1 in at least one FR (e.g., FR1, FR2, FR3, or FR4). In another embodiment, the present invention provides an antibody comprising a heavy chain-variable domain comprising a sequence of amino acids that differs from the sequence of H1 only at one or more residues where any one of the sequences of H2-H24 differs from the sequence of H1 (e.g., said sequence of said antibody differs from the sequence of H1 at residue(s) 6, 13, 24 etc.). In another embodiment, said sequence of said heavy chain-variable domain comprises at least one amino acid residue of any of the sequence of any one of H2-H24 at a position where it differs from the sequence of H1 (e.g., said sequence comprises the residue(s) Q6E, H13Q, G24A, etc.). In another embodiment, said sequence differs from the sequence of H1 in at least one CDR (e.g., CDR2 or CDR3). In another embodiment, said sequence differs from the sequence of H1 in at least one FR (e.g., FR1 or FR3).

In another embodiment, the present invention provides an antibody comprising an amino acid sequence selected from the group consisting of: a light chain complementarity determining region (CDR) 1 that differs by the insertion, deletion, or substitution of no more than 3, 2, 1, or 0 amino acid residues from a sequence selected from the group consisting of: residues 24-35 of SEQ ID NO:6, wherein the N at residue 8 is not substituted by an S; residues 24-35 of SEQ ID NO:8, wherein the T at residue 5 is not substituted by an S and/or the N at residue 7 is not substituted by an S and/or the D at residue 9 is not substituted by an S; residues 24-35 of SEQ ID NO:10, wherein the D at residue 9 is not substituted by an S; residues 24-35 of SEQ ID NO:12, wherein the N at residue 7 is not substituted by S and/or the N at residue 9 is not substituted by an S; and residues 24-35 of SEQ ID NO:14, wherein the G at residue 7 is not substituted by an S; a light chain CDR2 that differs by the insertion, deletion, or substitution of no more than 3, 2, 1, or 0 amino acid residues from a sequence selected from the group consisting of: residues 51-57 of SEQ ID NO:6, wherein the P at residue 7 is not substituted by a T; residues 51-57 of SEQ ID NO:10, wherein the S at residue 7 is not substituted by a T; and residues 51-57 of SEQ ID NO:12, wherein the T at residue 2 is not substituted by an A and/or the Y at residue 4 is not substituted by an S; a light chain CDR3 that differs by the insertion, deletion, or substitution of no more than 3, 2, 1, or 0 amino acid residues from a sequence selected from the group consisting of: residues 90-99 of SEQ ID NO:6, wherein the D at residue 4 is not substituted by a G, the H at residue 5 is not substituted by an S, the A at residue 7 is not substituted by a P, and/or the G at residue 8 is not substituted by a P; residues 90-99 of SEQ ID NO:8, wherein the R at residue 5 is not substituted by an S; and residues 90-99 of SEQ ID NO:14, wherein the M a residue 10 is not substituted by a T; a heavy chain CDR2 that differs by the insertion, deletion, or substitution of no more than 3 amino acid residues from the sequence of residues 50-65 of SEQ ID NO:18, wherein the S at residue 9 is not substituted by an N; and a heavy chain CDR3 that differs by the insertion, deletion, or substitution of no more than 3, 2, 1, or 0 amino acid residues from a sequence selected from the group consisting of: residues 98-104 of SEQ ID NO:18, wherein the T at residue 6 is not substituted by a D and/or the H at residue 7 is not substituted by a Y; residues 98-104 of SEQ ID NO:20, wherein the W at residue 4 is not substituted by a Y, the Y at residue 5 is not substituted by an F, the N at residue 6 is not substituted by a D, and/or the N at residue 7 is not substituted by a Y; residues 98-104 of SEQ ID NO:22, wherein the P at residue 6 is not substituted by a D and/or the W at residue 7 is not substituted by a Y; residues 98-104 of SEQ ID NO:24, wherein the T at residue 6 is not substituted by a D and/or the R at position 7 is not substituted by a Y; residues 98-104 of SEQ ID NO:26, wherein the Y at residue 5 is not substituted by an F; residues 98-104 of SEQ ID NO:30, wherein the W at residue 4 is not substituted by a Y; and residues 98-104 of SEQ ID NO:34, wherein the W at residue 4 is not substituted by a Y and/or the Y at residue 5 is not substituted by an F; wherein said antibody binds to IL-4 receptor alpha.

In another embodiment, the antibody inhibits the binding of IL-4 to an IL-4 receptor. In another embodiment, the antibody inhibits the binding of IL-13 to an IL-13 receptor. In another embodiment, the antibody inhibits the binding of IL-4 to an IL-4 receptor and of IL-13 to an IL-13 receptor. In another embodiment, the antibody specifically binds IL-4 receptor alpha.

In another embodiment, the antibody comprises two or three such light chain complementarity determining regions (CDR).

In another embodiment, the antibody comprises two or three such heavy chain complementarity determining regions.

In another embodiment, the antibody further comprises a framework segment (FR) comprising a sequence selected from the group consisting of: a light chain framework segment (FR) 1 that differs by the insertion, deletion, or substitution of no more than 3, 2, 1, or 0 amino acid residues from a sequence selected from the group consisting of: residues 1-23 of SEQ ID NO:4; residues 1-23 of SEQ ID NO:10; residues 1-23 of SEQ ID NO:12; and residues 1-23 of SEQ ID NO:14; a light chain FR2 that differs by the insertion, deletion, or substitution of no more than 3, 2, 1, or 0 amino acid residues from a sequence selected from the group consisting of: residues 36-50 of SEQ ID NO:4; residues 36-50 of SEQ ID NO:6; and residues 36-50 of SEQ ID NO:14; a light chain FR3 that differs by the insertion, deletion, or substitution of no more than 3, 2, 1, or 0 amino acid residues from a sequence selected from the group consisting of: residues 58-89 of SEQ ID NO:4; residues 58-89 of SEQ ID NO:10; and residues 58-89 of SEQ ID NO:12; a light chain FR4 that differs by the insertion, deletion, or substitution of no more than 3, 2, 1, 0 amino acid residues from a sequence selected from the group consisting of: residues 100-109 of SEQ ID NO:4; residues 100-109 of SEQ ID NO:8; and residues 100-109 of SEQ ID NO:12; a heavy chain FR1 that differs by the insertion, deletion, or substitution of no more than 3, 2, 1, or 0 amino acid residues from a sequence selected from the group consisting of: residues 1-30 of SEQ ID NO:16; and residues 1-30 of SEQ ID NO:42; heavy chain FR2 that differs by the insertion, deletion, or substitution of no more than 3, 2, 1, or 0 amino acid residues from the sequence residues 36-49 of SEQ ID NO:16, a heavy chain FR3 that differs by the insertion, deletion, or substitution of no more than 3, 2, 1, or 0 amino acid residues from a sequence selected from the group consisting of: residues 66-97 of SEQ ID NO:16; residues 66-97 of SEQ ID NO:18; and residues 66-97 of SEQ ID: NO:42; and a heavy chain FR4 that differs by the insertion, deletion, or substitution of no more than 3 amino acid residues from the sequence residues 105-115 of SEQ ID NO:16.

In another embodiment, the antibody comprises a light chain variable domain that is at least 80, 85, 90, 95, or 100% identical to a sequence selected from the group consisting of: SEQ ID NO:6, 8, 10, 12, and 14, with the proviso that the said light chain variable domain does not comprise the sequence of SEQ ID NO:4.

In another embodiment, the antibody comprises a heavy chain variable domain that is at least 80, 85, 90, 95, or 100% identical to a sequence selected from the group consisting of: SEQ ID NO:18, 20, 22, 24, 26, 28, 30, 32, 34, 36, 38, 40, 42, 46, 48, 50, 52, 54, 56, 58, 60, and 62 with the proviso that said heavy chain variable domain does not comprise the sequence of SEQ ID NO:16.

In another embodiment, the present invention provides a fragment of such an antibody, wherein said fragment binds to IL-4 receptor alpha.

In one embodiment, particular antibodies of the invention are selected from the group consisting of L2H1; an antibody that is cross-reactive L2H1, an antibody that binds to the same epitope as L2H1; an antibody that competes with L2H1 for binding to a cell that expresses human IL-4R; an antibody that possesses a biological activity of L2H1 and an antigen-binding fragment (including one derived by recombinant means) of L2H1. In one embodiment, the antibody has a binding affinity for human IL-4R that is substantially equivalent to the binding affinity of L2H1 for human IL-4R. Hybridoma cell lines that produce any such antibodies also are provided by the present invention.

One example of a biological activity of L2H1 is the ability to function as both an IL-4 antagonist and an IL-13 antagonist. In one embodiment, an antibody of the invention possesses IL-4-blocking activity substantially equivalent to that of L2H1; and possesses IL-13-blocking activity substantially equivalent to that of L2H1. Such activity may be measured in any suitable conventional assay (e.g., as measured in the CD23 expression assay described in Example 2).

Complementarity determining regions (CDRs) of a given antibody may be identified using the system described by Kabat et al. in *Sequences of Proteins of Immunological Interest*, $5^{th}$ Ed., US Dept. of Health and Human Services, PHS, NIH, NIH Publication no. 91-3242, 1991. Particular embodiments of antibodies of the present invention comprise, within the variable domain of their light chain, at least one of the complementarity determining regions (CDRs), or hypervariable regions, found in the light chain of L2H1. CDRs of L2H1 are discussed in Example 5. Thus, among the antibodies provided herein are those comprising from one to all three of the following sequences in the light chain variable domain of L2H1: amino acid residues 24-35; residues 51-57; and residues 90-99 of SEQ ID NO:6. Particular antibodies provided herein comprise, within the variable domain of their heavy chain, at least one of the CDRs found in the heavy chain of L2H1. Thus, among the antibodies provided herein are those comprising from one to all three of the following sequences in the heavy chain variable domain: residues 31-35; residues 50-65; and residues 98-104 of SEQ ID NO:16.

The DNA sequence of the variable domain of the light chain of L2H1 is presented in SEQ ID NO:5, and the encoded amino acid sequence is presented in SEQ ID NO:6. The DNA sequence for the variable domain of the heavy chain of L2H1 is presented as SEQ ID NO:15, and the encoded amino acid sequence is presented in SEQ ID NO:16. Antibodies of the present invention include, but are not limited to, antibodies that comprise, in their light chain, SEQ ID NO:6; and antibodies that additionally or alternatively comprise, in their heavy chain, SEQ ID NO:16.

In another embodiment, particular antibodies of the invention are selected from the group consisting of L3H1; an antibody that is cross-reactive with L3H1; an antibody that binds to the same epitope as L3H1; an antibody that competes with L3H1 for binding to a cell that expresses human IL-4R; an antibody that possesses a biological activity of L3H1; and an antigen-binding fragment of any of the foregoing antibodies. In one embodiment, the antibody has a binding affinity for human IL-4R that is substantially equivalent to the binding affinity of L3H1 for human IL-4R. Hybridoma cell lines that produce any such antibodies also are provided by the present invention.

One example of a biological activity of L3H1 is the ability to function as both an IL-4 antagonist and an IL-13 antagonist. In one embodiment, an antibody of the invention possesses IL-4-blocking activity substantially equivalent to that of L3H1, and possesses IL-13-blocking activity substantially equivalent to that of L3H1. Such activity may be measured in any suitable conventional assay (e.g., as measured in the CD23 expression assay described in Example 2).

IgG4 antibodies derived from L3H1 are provided herein. Another embodiment is directed to IgM antibodies derived from L3H1. Procedures for switching (altering) the subclass or isotype of an antibody are known in the pertinent field. Such procedures may involve, for example, recombinant DNA technology, whereby DNA encoding antibody polypeptide chains that confer the desired subclass is substituted for DNA encoding the corresponding polypeptide chain of the parent antibody.

The DNA sequence of the variable domain of the light chain of L3H1 is presented in SEQ ID NO:7, and the encoded amino acid sequence is presented in SEQ ID NO:8. The DNA sequence for the variable domain of the heavy chain of L3H1 is presented as SEQ ID NO:15, and the encoded amino acid sequence is presented in SEQ ID NO:16. Antibodies of the present invention include, but are not limited to, antibodies that comprise, in their light chain, residues 1 to 109 of SEQ ID NO:8; and antibodies that additionally or alternatively comprise, in their heavy chain, residues 1 to 115 of SEQ ID NO:16.

Particular embodiments of antibodies of the present invention comprise, within the variable domain of their light chain, at least one of the complementarity determining regions (CDRs), or hypervariable regions, found in the light chain of L3H1. CDRs of L3H1 are discussed in example 5. Thus, among the antibodies provided herein are those comprising from one to all three of the following sequences in the light chain variable domain: amino acid residues 24-35; residues 51-57; and residues 90-99 of SEQ ID NO:8. Particular antibodies provided herein comprise, within the variable domain of their heavy chain, at least one of the CDRs found in the heavy chain of L3H1. Thus, among the antibodies provided herein are those comprising from one to all three of the following sequences in the heavy chain variable domain: residues 31-35; residues 50-65; and residues 98-104 of SEQ ID NO:16.

In another embodiment, particular antibodies of the invention are selected from the group consisting of L4H1; an antibody that is cross-reactive with L4H1; an antibody that binds to the same epitope as L4H1; an antibody that competes with L4H1 for binding to a cell that expresses human IL-4R; an antibody that possesses a biological activity of L4H1; and an antigen-binding fragment of any of the foregoing antibodies. In one embodiment, the antibody has a binding affinity for human IL-4R that is substantially equivalent to the binding affinity of L4H1 for human IL-4R. Hybridoma cell lines that produce any such antibodies also are provided by the present invention.

One example of a biological activity of L4H1 is the ability to function as both an IL-4 antagonist and an IL-13 antagonist. In one embodiment, an antibody of the invention possesses IL-4-blocking activity substantially equivalent to that of L4H1; and possesses IL-13-blocking activity substantially equivalent to that of L4H1. Such activity may be measured in any suitable conventional assay (e.g., as measured in the CD23 expression assay described in Example 2).

The DNA sequence of the variable domain of the light chain of L4H1 is presented in SEQ ID NO:9, and the encoded amino acid sequence is presented in SEQ ID NO:10. The DNA sequence for the variable domain of the heavy chain of L4H1 is presented as SEQ ID NO:15, and the encoded amino acid sequence is presented in SEQ ID NO:16. Antibodies of the present invention include, but are not limited to, antibodies that comprise, in their light chain, residues 1 to 109 of SEQ ID NO:10; and antibodies that additionally or alternatively comprise, in their heavy chain, residues 1 to 115 of SEQ ID NO:16.

Particular embodiments of antibodies of the present invention comprise, within the variable domain of their light chain, at least one of the complementarity determining regions (CDRs), or hypervariable regions, found in the light chain of L4H1. CDRs of L4H1 are discussed in example 5. Thus, among the antibodies provided herein are those comprising from one to all three of the following sequences in the light chain variable domain: amino acid residues 24-35; residues 51-57; and residues 90-99 of SEQ ID NO:10. Particular antibodies provided herein comprise, within the variable domain of their heavy chain, at least one of the CDRs found in the heavy chain of L4H1. Thus, among the antibodies provided herein are those comprising from one to all three of the following sequences in the heavy chain variable domain: residues 31-35; residues 50-65; and residues 99-104 of SEQ ID NO:16.

In another embodiment, particular antibodies of the invention are selected from the group consisting of L5H1; an antibody that is cross-reactive with L5H1; an antibody that binds to the same epitope as L5H1; an antibody that competes with L5H1 for binding to a cell that expresses human IL-4R; an antibody that possesses a biological activity of L5H1; and an antigen-binding fragment of any of the foregoing antibodies. In one embodiment, the antibody has a binding affinity for human IL-4R that is substantially equivalent to the binding affinity of L5H1 for human IL-4R. Hybridoma cell lines that produce any such antibodies also are provided by the present invention.

One example of a biological activity of L5H1 is the ability to function as both an IL-4 antagonist and an IL-13 antagonist. In one embodiment, an antibody of the invention possesses IL-4-blocking activity substantially equivalent to that of L5H1; and possesses IL-13-blocking activity substantially equivalent to that of L5H1. Such activity may be measured in any suitable conventional assay (e.g., as measured in the CD23 expression assay described in Example 2).

The DNA sequence of the variable domain of the light chain of L5H1 is presented in SEQ ID NO:11, and the encoded amino acid sequence is presented in SEQ ID NO:12. The DNA sequence for the variable domain of the heavy chain of L5H1 is presented as SEQ ID NO:15, and the encoded amino acid sequence is presented in SEQ ID NO:16. Antibodies of the present invention include, but are not limited to, antibodies that comprise, in their light chain, residues 1 to 109 of SEQ ID NO:12; and antibodies that additionally or alternatively comprise, in their heavy chain, residues 1 to 115 of SEQ ID NO:16.

Particular embodiments of antibodies of the present invention comprise, within the variable domain of their light chain, at least one of the complementarity determining regions (CDRs), or hypervariable regions, found in the light chain of L5H1. CDRs of L5H1 are discussed in example 5. Thus, among the antibodies provided herein are those comprising from one to all three of the following sequences in the light chain variable domain: amino acid residues 24-35; residues 51-57; and residues 90-99 of SEQ ID NO:12. Particular antibodies provided herein comprise, within the variable domain of their heavy chain, at least one of the CDRs found in the heavy chain of L5H1. Thus, among the antibodies provided herein are those comprising from one to all three of the following sequences in the heavy chain variable domain: residues 31-35; residues 50-65; and residues 98-104 of SEQ ID NO:16.

In another embodiment, particular antibodies of the invention are selected from the group consisting of L1H2; an antibody that is cross-reactive with L1H2; an antibody that binds to the same epitope as L1H2; an antibody that competes with L1H2 for binding to a cell that expresses human IL-4R; an antibody that possesses a biological activity of L1H2; and an antigen-binding fragment of any of the foregoing antibodies. In one embodiment, the antibody has a binding affinity for human IL-4R that is substantially equivalent to the binding affinity of L1H2 for human IL-4R. Hybridoma cell lines that produce any such antibodies also are provided by the present invention.

One example of a biological activity of L1H2 is the ability to function as both an IL-4 antagonist and an IL-13 antagonist. In one embodiment, an antibody of the invention possesses IL-4-blocking activity substantially equivalent to that of L1H2; and possesses IL-13-blocking activity substantially equivalent to that of L1H2. Such activity may be measured in any suitable conventional assay (e.g., as measured in the CD23 expression assay described in Example 2).

The DNA sequence of the variable domain of the light chain of L1H2 is presented in SEQ ID NO:3, and the encoded amino acid sequence is presented in SEQ ID NO:4. The DNA sequence for the variable domain of the heavy chain of L1H2 is presented as SEQ ID NO:17, and the encoded amino acid sequence is presented in SEQ ID NO:18. Antibodies of the present invention include, but are not limited to, antibodies that comprise, in their light chain, residues 1 to 109 of SEQ ID NO:4; and antibodies that additionally or alternatively comprise, in their heavy chain, residues 1 to 115 of SEQ ID NO:18.

Particular embodiments of antibodies of the present invention comprise, within the variable domain of their light chain, at least one of the complementarity determining regions (CDRs), or hypervariable regions, found in the light chain of L1H2. CDRs of L1H2 are discussed in example 5. Thus, among the antibodies provided herein are those comprising from one to all three of the following sequences in the light chain variable domain: amino acid residues 24-35; residues 51-57; and residues 90-99 of SEQ ID NO:4. Particular antibodies provided herein comprise, within the variable domain of their heavy chain, at least one of the CDRs found in the heavy chain of L1H2. Thus, among the antibodies provided herein are those comprising from one to all three of the following sequences in the heavy chain variable domain: residues 31-35; residues 50-65; and residues 98-104 of SEQ ID NO:18.

In another embodiment, particular antibodies of the invention are selected from the group consisting of L1H3; an antibody that is cross-reactive with L1H3; an antibody that binds to the same epitope as L1H3; an antibody that competes with L1H3 for binding to a cell that expresses human IL-4R; an antibody that possesses a biological activity of L1H3; and an antigen-binding fragment of any of the foregoing antibodies. In one embodiment, the antibody has a binding affinity for human IL-4R that is substantially equivalent to the binding affinity of L1H3 for human IL-4R. Hybridoma cell lines that produce any such antibodies also are provided by the present invention.

One example of a biological activity of L1H3 is the ability to function as both an IL-4 antagonist and an IL-13 antagonist. In one embodiment, an antibody of the invention possesses IL-4-blocking activity substantially equivalent to that of L1H3; and possesses IL-13-blocking activity substantially equivalent to that of L1H3. Such activity may be measured in any suitable conventional assay (e.g., as measured in the CD23 expression assay described in Example 2).

The DNA sequence of the variable domain of the light chain of L1H3 is presented in SEQ ID NO:3, and the encoded amino acid sequence is presented in SEQ ID NO:4. The DNA sequence for the variable domain of the heavy chain of L1H3 is presented as SEQ ID NO:19, and the encoded amino acid sequence is presented in SEQ ID NO:20. Antibodies of the present invention include, but are not limited to, antibodies that comprise, in their light chain, residues 1 to 109 of SEQ ID NO:4; and antibodies that additionally or alternatively comprise, in their heavy chain, residues 1 to 115 of SEQ ID NO:20.

Particular embodiments of antibodies of the present invention comprise, within the variable domain of their light chain, at least one of the complementarity determining regions (CDRs), or hypervariable regions, found in the light chain of L1H3. CDRs of L1H3 are discussed in example 5. Thus, among the antibodies provided herein are those comprising from one to all three of the following sequences in the light chain variable domain: amino acid residues 24-35; residues 51-57; and residues 90-99 of SEQ ID NO:4. Particular antibodies provided herein comprise, within the variable domain of their heavy chain, at least one of the CDRs found in the heavy chain of L1H3. Thus, among the antibodies provided herein are those comprising from one to all three of the following sequences in the heavy chain variable domain: residues 31-35; residues 50-65; and residues 98-104 of SEQ ID NO:20.

In another embodiment, particular antibodies of the invention are selected from the group consisting of L1H4; an antibody that is cross-reactive with L1H4; an antibody that binds to the same epitope as L1H4; an antibody that competes with L1H4 for binding to a cell that expresses human IL-4R; an antibody that possesses a biological activity of L1H4; and an antigen-binding fragment of any of the foregoing antibodies. In one embodiment, the antibody has a binding affinity for human IL-4R that is substantially equivalent to the binding affinity of L1H4 for human IL-4R. Hybridoma cell lines that produce any such antibodies also are provided by the present invention.

One example of a biological activity of L1H4 is the ability to function as both an IL-4 antagonist and an IL-13 antagonist. In one embodiment, an antibody of the invention possesses IL-4-blocking activity substantially equivalent to that of L1H4; and possesses IL-13-blocking activity substantially equivalent to that of L1H4. Such activity may be measured in any suitable conventional assay (e.g., as measured in the CD23 expression assay described in Example 2).

The DNA sequence of the variable domain of the light chain of L1H4 is presented in SEQ ID NO:3, and the encoded amino acid sequence is presented in SEQ ID NO:4. The DNA sequence for the variable domain of the heavy chain of L1H4 is presented as SEQ ID NO:21, and the encoded amino acid sequence is presented in SEQ ID NO:22. Antibodies of the present invention include, but are not limited to, antibodies that comprise, in their light chain, residues 1 to 109 of SEQ ID NO:4; and antibodies that additionally or alternatively comprise, in their heavy chain, residues 1 to 115 of SEQ ID NO:22.

Particular embodiments of antibodies of the present invention comprise, within the variable domain of their light chain, at least one of the complementarity determining regions (CDRs), or hypervariable regions, found in the light chain of L1H4. CDRs of L1H4 are discussed in example 5. Thus, among the antibodies provided herein are those comprising from one to all three of the following sequences in the light chain variable domain: amino acid residues 24-35; residues 51-57; and residues 90-99 of SEQ ID NO:4. Particular antibodies provided herein comprise, within the variable domain of their heavy chain, at least one of the CDRs found in the heavy chain of L1H4. Thus, among the antibodies provided herein are those comprising from one to all three of the following sequences in the heavy chain variable domain: residues 31-35; residues 50-65; and residues 98-104 of SEQ ID NO:22.

In another embodiment, particular antibodies of the invention are selected from the group consisting of L1H5; an antibody that is cross-reactive with L1H5; an antibody that binds to the same epitope as L1H5; an antibody that competes with L1H5 for binding to a cell that expresses human IL-4R; an antibody that possesses a biological activity of L1H5; and an antigen-binding fragment of any of the foregoing antibodies. In one embodiment, the antibody has a binding affinity for human IL-4R that is substantially equivalent to the binding affinity of L1H5 for human IL-4R. Hybridoma cell lines that produce any such antibodies also are provided by the present invention.

One example of a biological activity of L1H5 is the ability to function as both an IL-4 antagonist and an IL-13 antagonist. In one embodiment, an antibody of the invention possesses IL-4-blocking activity substantially equivalent to that of L1H5; and possesses IL-13-blocking activity substantially equivalent to that of L1H5. Such activity may be measured in any suitable conventional assay (e.g., as measured in the CD23 expression assay described in Example 2).

The DNA sequence of the variable domain of the light chain of L1H5 is presented in SEQ ID NO:3, and the encoded amino acid sequence is presented in SEQ ID NO:4. The DNA sequence for the variable domain of the heavy chain of L1H5 is presented as SEQ ID NO:23, and the encoded amino acid sequence is presented in SEQ ID NO:24. Antibodies of the present invention include, but are not limited to, antibodies that comprise, in their light chain, residues 1 to 109 of SEQ ID NO:4; and antibodies that additionally or alternatively comprise, in their heavy chain, residues 1 to 115 of SEQ ID NO:24.

Particular embodiments of antibodies of the present invention comprise, within the variable domain of their light chain, at least one of the complementarity determining regions (CDRs), or hypervariable regions, found in the light chain of L1H5. CDRs of L1H5 are discussed in example 5. Thus, among the antibodies provided herein are those comprising from one to all three of the following sequences in the light chain variable domain: amino acid residues 24-35; residues 51-57; and residues 90-99 of SEQ ID NO:4. Particular antibodies provided herein comprise, within the variable domain of their heavy chain, at least one of the CDRs found in the heavy chain of L1H5. Thus, among the antibodies provided herein are those comprising from one to all three of the following sequences in the heavy chain variable domain: residues 31-35; residues 50-65; and residues 98-104 of SEQ ID NO:24.

In another embodiment, particular antibodies of the invention are selected from the group consisting of L1H6; an antibody that is cross-reactive with L1H6; an antibody that binds to the same epitope as L1H6; an antibody that competes with L1H6 for binding to a cell that expresses human IL-4R; an antibody that possesses a biological activity of L1H6; and an antigen-binding fragment of any of the foregoing antibodies. In one embodiment, the antibody has a binding affinity for human IL-4R that is substantially equivalent to the binding affinity of L1H6 for human IL-4R. Hybridoma cell lines that produce any such antibodies also are provided by the present invention.

One example of a biological activity of L1H6 is the ability to function as both an IL-4 antagonist and an IL-13 antagonist. In one embodiment, an antibody of the invention possesses IL-4-blocking activity substantially equivalent to that of L1H6; and possesses IL-13-blocking activity substantially equivalent to that of L1H6. Such activity may be measured in any suitable conventional assay (e.g., as measured in the CD23 expression assay described in Example 2).

The DNA sequence of the variable domain of the light chain of L1H6 is presented in SEQ ID NO:3, and the encoded amino acid sequence is presented in SEQ ID NO:4. The DNA sequence for the variable domain of the heavy chain of L1H6 is presented as SEQ ID NO:25, and the encoded amino acid sequence is presented in SEQ ID NO:26. Antibodies of the present invention include, but are not limited to, antibodies that comprise, in their light chain, residues 1 to 109 of SEQ ID NO:4; and antibodies that additionally or alternatively comprise, in their heavy chain, residues 1 to 115 of SEQ ID NO:26.

Particular embodiments of antibodies of the present invention comprise, within the variable domain of their light chain, at least one of the complementarity determining regions (CDRs), or hypervariable regions, found in the light chain of L1H6. CDRs of L1H6 are discussed in example 5. Thus, among the antibodies provided herein are those comprising from one to all three of the following sequences in the light chain variable domain: amino acid residues 24-35; residues 51-57; and residues 90-99 of SEQ ID NO:4. Particular antibodies provided herein comprise, within the variable domain of their heavy chain, at least one of the CDRs found in the heavy chain of L1H6. Thus, among the antibodies provided herein are those comprising from one to all three of the following sequences in the heavy chain variable domain: residues 31-35; residues 50-65; and residues 98-104 of SEQ ID NO:26.

In another embodiment, particular antibodies of the invention are selected from the group consisting of L1H7; an antibody that is cross-reactive with L1H7; an antibody that binds to the same epitope as L1H7; an antibody that competes with L1H7 for binding to a cell that expresses human IL-4R; an antibody that possesses a biological activity of L1H7; and an antigen-binding fragment of any of the foregoing antibodies. In one embodiment, the antibody has a binding affinity for human IL-4R that is substantially equivalent to the binding affinity of L1H7 for human IL-4R. Hybridoma cell lines that produce any such antibodies also are provided by the present invention.

One example of a biological activity of L1H7 is the ability to function as both an IL-4 antagonist and an IL-13 antagonist. In one embodiment, an antibody of the invention possesses IL-4-blocking activity substantially equivalent to that of L1H7; and possesses IL-13-blocking activity substantially equivalent to that of L1H7. Such activity may be measured in any suitable conventional assay (e.g., as measured in the CD23 expression assay described in Example 2).

The DNA sequence of the variable domain of the light chain of L1H7 is presented in SEQ ID NO:3, and the encoded amino acid sequence is presented in SEQ ID NO:4. The DNA sequence for the variable domain of the heavy chain of L1H7 is presented as SEQ ID NO:27, and the encoded amino acid sequence is presented in SEQ ID NO:28. Antibodies of the present invention include, but are not limited to, antibodies that comprise, in their light chain, residues 1 to 109 of SEQ ID NO:4; and antibodies that additionally or alternatively comprise, in their heavy chain, residues 1 to 115 of SEQ ID NO:28.

Particular embodiments of antibodies of the present invention comprise, within the variable domain of their light chain, at least one of the complementarity determining regions (CDRs), or hypervariable regions, found in the light chain of L1H7. CDRs of L1H7 are discussed in example 5. Thus, among the antibodies provided herein are those comprising from one to all three of the following sequences in the light chain variable domain: amino acid residues 24-35; residues 51-57; and residues 90-99 of SEQ ID NO:4. Particular antibodies provided herein comprise, within the variable domain of their heavy chain, at least one of the CDRs found in the heavy chain of L1H7. Thus, among the antibodies provided herein are those comprising from one to all three of the following sequences in the heavy chain variable domain: residues 31-35; residues 50-65; and residues 98-104 of SEQ ID NO:28.

In another embodiment, particular antibodies of the invention are selected from the group consisting of L1H8; an antibody that is cross-reactive with L1H8; an antibody that binds to the same epitope as L1H8; an antibody that competes with L1H8 for binding to a cell that expresses human IL-4R; an antibody that possesses a biological activity of L1H8; and an antigen-binding fragment of any of the foregoing antibodies. In one embodiment, the antibody has a binding affinity for human IL-4R that is substantially equivalent to the binding affinity of L1H8 for human IL-4R. Hybridoma cell lines that produce any such antibodies also are provided by the present invention.

One example of a biological activity of L1H8 is the ability to function as both an IL-4 antagonist and an IL-13 antagonist. In one embodiment, an antibody of the invention possesses IL-4-blocking activity substantially equivalent to that of L1H8; and possesses IL-13-blocking activity substantially equivalent to that of L1H8. Such activity may be measured in any suitable conventional assay (e.g., as measured in the CD23 expression assay described in Example 2).

The DNA sequence of the variable domain of the light chain of L1H8 is presented in SEQ ID NO:3, and the encoded amino acid sequence is presented in SEQ ID NO:4. The DNA sequence for the variable domain of the heavy chain of L1H8 is presented as SEQ ID NO:29, and the encoded amino acid sequence is presented in SEQ ID NO:30. Antibodies of the present invention include, but are not limited to, antibodies that comprise, in their light chain, residues 1 to 109 of SEQ ID NO:4; and antibodies that additionally or alternatively comprise, in their heavy chain, residues 1 to 115 of SEQ ID NO:30.

Particular embodiments of antibodies of the present invention comprise, within the variable domain of their light chain, at least one of the complementarity determining regions (CDRs), or hypervariable regions, found in the light chain of L1H8. CDRs of L1H8 are discussed in example 5. Thus, among the antibodies provided herein are those comprising from one to all three of the following sequences in the light chain variable domain: amino acid residues 24-35; residues 51-57; and residues 90-99 of SEQ ID NO:4. Particular antibodies provided herein comprise, within the variable domain of their heavy chain, at least one of the CDRs found in the heavy chain of L1H8. Thus, among the antibodies provided herein are those comprising from one to all three of the following sequences in the heavy chain variable domain: residues 31-35; residues 50-65; and residues 98-104 of SEQ ID NO:30.

In another embodiment, particular antibodies of the invention are selected from the group consisting of L1H9; an antibody that is cross-reactive with L1H9; an antibody that binds to the same epitope as L1H9; an antibody that competes with L1H9 for binding to a cell that expresses human IL-4R; an antibody that possesses a biological activity of L1H9; and an antigen-binding fragment of any of the foregoing antibodies. In one embodiment, the antibody has a binding affinity for human IL-4R that is substantially equivalent to the binding affinity of L1H9 for human IL-4R. Hybridoma cell lines that produce any such antibodies also are provided by the present invention.

One example of a biological activity of L1H9 is the ability to function as both an IL-4 antagonist and an IL-13 antagonist. In one embodiment, an antibody of the invention possesses IL-4-blocking activity substantially equivalent to that of L1H9; and possesses IL-13-blocking activity substantially equivalent to that of L1H9. Such activity may be measured in any suitable conventional assay (e.g., as measured in the CD23 expression assay described in Example 2).

The DNA sequence of the variable domain of the light chain of L1H9 is presented in SEQ ID NO:3, and the encoded amino acid sequence is presented in SEQ ID NO:4. The DNA sequence for the variable domain of the heavy chain of L1H9 is presented as SEQ ID NO:31, and the encoded amino acid sequence is presented in SEQ ID NO:32. Antibodies of the present invention include, but are not limited to, antibodies that comprise, in their light chain, residues 1 to 109 of SEQ ID NO:4; and antibodies that additionally or alternatively comprise, in their heavy chain, residues 1 to 115 of SEQ ID NO:32.

Particular embodiments of antibodies of the present invention comprise, within the variable domain of their light chain, at least one of the complementarity determining regions (CDRs), or hypervariable regions, found in the light chain of L1H9. CDRs of L1H9 are discussed in example 5. Thus, among the antibodies provided herein are those comprising from one to all three of the following sequences in the light chain variable domain: amino acid residues 24-35; residues 51-57; and residues 90-99 of SEQ ID NO:4. Particular antibodies provided herein comprise, within the variable domain of their heavy chain, at least one of the CDRs found in the heavy chain of L1H9. Thus, among the antibodies provided herein are those comprising from one to all three of the following sequences in the heavy chain variable domain: residues 31-35; residues 50-65; and residues 98-104 of SEQ ID NO:32.

In another embodiment, particular antibodies of the invention are selected from the group consisting of L1H10; an antibody that is cross-reactive with L1H10; an antibody that binds to the same epitope as L1H10; an antibody that competes with L1H10 for binding to a cell that expresses human IL-4R; an antibody that possesses a biological activity of L1H10; and an antigen-binding fragment of any of the foregoing antibodies. In one embodiment, the antibody has a binding affinity for human IL-4R that is substantially equivalent to the binding affinity of L1H10 for human IL-4R. Hybridoma cell lines that produce any such antibodies also are provided by the present invention.

One example of a biological activity of L1H10 is the ability to function as both an IL-4 antagonist and an IL-13 antagonist. In one embodiment, an antibody of the invention possesses IL-4-blocking activity substantially equivalent to that of L1H10; and possesses IL-13-blocking activity substantially equivalent to that of L1H10. Such activity may be measured in any suitable conventional assay (e.g., as measured in the CD23 expression assay described in Example 2).

The DNA sequence of the variable domain of the light chain of L1H10 is presented in SEQ ID NO:3, and the encoded amino acid sequence is presented in SEQ ID NO:4. The DNA sequence for the variable domain of the heavy chain of L1H10 is presented as SEQ ID NO:33, and the encoded amino acid sequence is presented in SEQ ID NO:34. Antibodies of the present invention include, but are not limited to, antibodies that comprise, in their light chain, residues 1 to 109 of SEQ ID NO:4; and antibodies that additionally or alternatively comprise, in their heavy chain, residues 1 to 115 of SEQ ID NO:34.

Particular embodiments of antibodies of the present invention comprise, within the variable domain of their light chain, at least one of the complementarity determining regions (CDRs), or hypervariable regions, found in the light chain of L1H10. CDRs of L1H10 are discussed in example 5. Thus, among the antibodies provided herein are those comprising from one to all three of the following sequences in the light chain variable domain: amino acid residues 24-35; residues 51-57; and residues 90-99 of SEQ ID NO:4. Particular antibodies provided herein comprise, within the variable domain of their heavy chain, at least one of the CDRs found in the heavy chain of L1H10. Thus, among the antibodies provided herein are those comprising from one to all three of the following sequences in the heavy chain variable domain: residues 31-35; residues 50-65; and residues 98-104 of SEQ ID NO:34.

In another embodiment, particular antibodies of the invention are selected from the group consisting of L1H11; an antibody that is cross-reactive with L1H11; an antibody that binds to the same epitope as L1H11; an antibody that competes with L1H11 for binding to a cell that expresses human IL-4R; an antibody that possesses a biological activity of L1H11; and an antigen-binding fragment of any of the foregoing antibodies. In one embodiment, the antibody has a binding affinity for human IL-4R that is substantially equivalent to the binding affinity of L1H11 for human IL-4R. Hybridoma cell lines that produce any such antibodies also are provided by the present invention.

One example of a biological activity of L1H11 is the ability to function as both an IL-4 antagonist and an IL-13 antagonist. In one embodiment, an antibody of the invention possesses IL-4-blocking activity substantially equivalent to that of L1H11; and possesses IL-13-blocking activity substantially equivalent to that of L1H11. Such activity may be measured in any suitable conventional assay (e.g., as measured in the CD23 expression assay described in Example 2).

The DNA sequence of the variable domain of the light chain of L1H11 is presented in SEQ ID NO:3, and the encoded amino acid sequence is presented in SEQ ID NO:4. The DNA sequence for the variable domain of the heavy chain of L1H11 is presented as SEQ ID NO:35, and the encoded amino acid sequence is presented in SEQ ID NO:36. Antibodies of the present invention include, but are not limited to, antibodies that comprise, in their light chain, residues 1 to 109 of SEQ ID NO:4; and antibodies that additionally or alternatively comprise, in their heavy chain, residues 1 to 115 of SEQ ID NO:36.

Particular embodiments of antibodies of the present invention comprise, within the variable domain of their light chain, at least one of the complementarity determining regions (CDRs), or hypervariable regions, found in the light chain of L1H11. CDRs of L1H11 are discussed in example 5. Thus, among the antibodies provided herein are those comprising from one to all three of the following sequences in the light chain variable domain: amino acid residues 24-35; residues 51-57; and residues 90-99 of SEQ ID NO:4. Particular antibodies provided herein comprise, within the variable domain of their heavy chain, at least one of the CDRs found in the heavy chain of L1H11. Thus, among the antibodies provided herein are those comprising from one to all three of the following sequences in the heavy chain variable domain: residues 31-35; residues 50-65; and residues 98-104 of SEQ ID NO:36.

In another embodiment, particular antibodies of the invention are selected from the group consisting of L2H4; an antibody that is cross-reactive with L2H4; an antibody that binds to the same epitope as L2H4; an antibody that competes with L2H4 for binding to a cell that expresses human IL-4R; an antibody that possesses a biological activity of L2H4; and an antigen-binding fragment of any of the foregoing antibodies. In one embodiment, the antibody has a binding affinity for human IL-4R that is substantially equivalent to the binding affinity of L2H4 for human IL-4R. Hybridoma cell lines that produce any such antibodies also are provided by the present invention.

One example of a biological activity of L2H4 is the ability to function as both an IL-4 antagonist and an IL-13 antagonist. In one embodiment, an antibody of the invention possesses IL-4-blocking activity substantially equivalent to that of L2H4; and possesses IL-13-blocking activity substantially equivalent to that of L2H4. Such activity may be measured in any suitable conventional assay (e.g., as measured in the CD23 expression assay described in Example 2).

The DNA sequence of the variable domain of the light chain of L2H4 is presented in SEQ ID NO:5, and the encoded amino acid sequence is presented in SEQ ID NO:6. The DNA sequence for the variable domain of the heavy chain of L2H4 is presented as SEQ ID NO:21, and the encoded amino acid sequence is presented in SEQ ID NO:22. Antibodies of the present invention include, but are not limited to, antibodies that comprise, in their light chain, residues 1 to 109 of SEQ ID NO:6; and antibodies that additionally or alternatively comprise, in their heavy chain, residues 1 to 115 of SEQ ID NO:22.

Particular embodiments of antibodies of the present invention comprise, within the variable domain of their light chain, at least one of the complementarity determining regions (CDRs), or hypervariable regions, found in the light chain of L2H4. CDRs of L2H4 are discussed in example 5. Thus, among the antibodies provided herein are those comprising from one to all three of the following sequences in the light chain variable domain: amino acid residues 24-35; residues 51-57; and residues 90-99 of SEQ ID NO:6. Particular antibodies provided herein comprise, within the variable domain of their heavy chain, at least one of the CDRs found in the heavy chain of L2H4. Thus, among the antibodies provided herein are those comprising from one to all three of the following sequences in the heavy chain variable domain: residues 31-35; residues 50-65; and residues 98-104 of SEQ ID NO:22.

In another embodiment, particular antibodies of the invention are selected from the group consisting of L2H12; an antibody that is cross-reactive with L2H12; an antibody that binds to the same epitope as L2H12; an antibody that competes with L2H12 for binding to a cell that expresses human IL-4R; an antibody that possesses a biological activity of L2H12; and an antigen-binding fragment of any of the foregoing antibodies. In one embodiment, the antibody has a binding affinity for human IL-4R that is substantially equivalent to the binding affinity of L2H12 for human IL-4R. Hybridoma cell lines that produce any such antibodies also are provided by the present invention.

One example of a biological activity of L2H12 is the ability to function as both an IL-4 antagonist and an IL-13 antagonist. In one embodiment, an antibody of the invention possesses IL-4-blocking activity substantially equivalent to that of L2H12; and possesses IL-13-blocking activity substantially equivalent to that of L2H12. Such activity may be measured in any suitable conventional assay (e.g., as measured in the CD23 expression assay described in Example 2).

The DNA sequence of the variable domain of the light chain of L2H12 is presented in SEQ ID NO:5, and the encoded amino acid sequence is presented in SEQ ID NO:6. The DNA sequence for the variable domain of the heavy chain of L2H12 is presented as SEQ ID NO:37, and the encoded amino acid sequence is presented in SEQ ID NO:38. Antibodies of the present invention include, but are not limited to, antibodies that comprise, in their light chain, residues 1 to 109 of SEQ ID NO:6; and antibodies that additionally or alternatively comprise, in their heavy chain, residues 1 to 115 of SEQ ID NO:38.

Particular embodiments of antibodies of the present invention comprise, within the variable domain of their light chain, at least one of the complementarity determining regions (CDRs), or hypervariable regions, found in the light chain of L2H12. CDRs of L2H12 are discussed in example 5. Thus, among the antibodies provided herein are those comprising from one to all three of the following sequences in the light chain variable domain: amino acid residues 24-35; residues 51-57; and residues 90-99 of SEQ ID NO:6. Particular antibodies provided herein comprise, within the variable domain of their heavy chain, at least one of the CDRs found in the heavy chain of L2H12. Thus, among the antibodies provided herein are those comprising from one to all three of the following sequences in the heavy chain variable domain: residues 31-35; residues 50-65; and residues 98-104 of SEQ ID NO:38.

In another embodiment, particular antibodies of the invention are selected from the group consisting of L2H13; an antibody that is cross-reactive with L2H13; an antibody that binds to the same epitope as L2H13; an antibody that competes with L2H13 for binding to a cell that expresses human IL-4R; an antibody that possesses a biological activity of L2H13; and an antigen-binding fragment of any of the foregoing antibodies. In one embodiment, the antibody has a binding affinity for human IL-4R that is substantially equivalent to the binding affinity of L2H13 for human IL-4R. Hybridoma cell lines that produce any such antibodies also are provided by the present invention.

One example of a biological activity of L2H13 is the ability to function as both an IL-4 antagonist and an IL-13 antagonist. In one embodiment, an antibody of the invention possesses IL-4-blocking activity substantially equivalent to that of L2H13; and possesses IL-13-blocking activity substantially equivalent to that of L2H13. Such activity may be measured in any suitable conventional assay (e.g., as measured in the CD23 expression assay described in Example 2).

The DNA sequence of the variable domain of the light chain of L2H13 is presented in SEQ ID NO:5, and the encoded amino acid sequence is presented in SEQ ID NO:6. The DNA sequence for the variable domain of the heavy chain of L2H13 is presented as SEQ ID NO:39, and the encoded amino acid sequence is presented in SEQ ID NO:40. Antibodies of the present invention include, but are not limited to, antibodies that comprise, in their light chain, residues 1 to 109 of SEQ ID NO:6; and antibodies that additionally or alternatively comprise, in their heavy chain, residues 1 to 115 of SEQ ID NO:40.

Particular embodiments of antibodies of the present invention comprise, within the variable domain of their light chain, at least one of the complementarity determining regions (CDRs), or hypervariable regions, found in the light chain of L2H13. CDRs of L2H13 are discussed in example 5. Thus, among the antibodies provided herein are those comprising from one to all three of the following sequences in the light chain variable domain: amino acid residues 24-35; residues 51-57; and residues 90-99 of SEQ ID NO:6. Particular antibodies provided herein comprise, within the variable domain of their heavy chain, at least one of the CDRs found in the heavy chain of L2H13. Thus, among the antibodies provided herein are those comprising from one to all three of the following sequences in the heavy chain variable domain: residues 31-35; residues 50-65; and residues 98-104 of SEQ ID NO:40.

In another embodiment, particular antibodies of the invention are selected from the group consisting of L2H14; an antibody that is cross-reactive with L2H14; an antibody that binds to the same epitope as L2H14; an antibody that competes with L2H14 for binding to a cell that expresses human IL-4R; an antibody that possesses a biological activity of L2H14; and an antigen-binding fragment of any of the foregoing antibodies. In one embodiment, the antibody has a binding affinity for human IL-4R that is substantially equivalent to the binding affinity of L2H14 for human IL-4R. Hybridoma cell lines that produce any such antibodies also are provided by the present invention.

One example of a biological activity of L2H14 is the ability to function as both an IL-4 antagonist and an IL-13 antagonist. In one embodiment, an antibody of the invention possesses IL-4-blocking activity substantially equivalent to that of L2H14; and possesses IL-13-blocking activity substantially equivalent to that of L2H14. Such activity may be measured in any suitable conventional assay (e.g., as measured in the CD23 expression assay described in Example 2).

The DNA sequence of the variable domain of the light chain of L2H14 is presented in SEQ ID NO:5, and the encoded amino acid sequence is presented in SEQ ID NO:6. The DNA sequence for the variable domain of the heavy chain of L2H14 is presented as SEQ ID NO:41, and the encoded amino acid sequence is presented in SEQ ID NO:42. Antibodies of the present invention include, but are not limited to, antibodies that comprise, in their light chain, residues 1 to 109 of SEQ ID NO:6; and antibodies that additionally or alternatively comprise, in their heavy chain, residues 1 to 115 of SEQ ID NO:42.

Particular embodiments of antibodies of the present invention comprise, within the variable domain of their light chain, at least one of the complementarity determining regions (CDRs), or hypervariable regions, found in the light chain of L2H14. CDRs of L2H14 are discussed in example 5. Thus, among the antibodies provided herein are those comprising from one to all three of the following sequences in the light chain variable domain: amino acid residues 24-35; residues 51-57; and residues 90-99 of SEQ ID NO:6. Particular antibodies provided herein comprise, within the variable domain of their heavy chain, at least one of the CDRs found in the heavy chain of L2H14. Thus, among the antibodies provided herein are those comprising from one to all three of the following sequences in the heavy chain variable domain: residues 31-35; residues 50-65; and residues 98-104 of SEQ ID NO:42.

In another embodiment, particular antibodies of the invention are selected from the group consisting of L6H1; an antibody that is cross-reactive with L6H1; an antibody that binds to the same epitope as L6H1; an antibody that competes with L6H1 for binding to a cell that expresses human IL-4R; an antibody that possesses a biological activity of L6H1; and an antigen-binding fragment of any of the foregoing antibodies. In one embodiment, the antibody has a binding affinity for human IL-4R that is substantially equivalent to the binding affinity of L6H1 for human IL-4R. Hybridoma cell lines that produce any such antibodies also are provided by the present invention.

One example of a biological activity of L6H1 is the ability to function as both an IL-4 antagonist and an IL-13 antagonist. In one embodiment, an antibody of the invention possesses IL-4-blocking activity substantially equivalent to that of L6H1; and possesses IL-13-blocking activity substantially equivalent to that of L6H1. Such activity may be measured in any suitable conventional assay (e.g., as measured in the CD23 expression assay described in Example 2).

The DNA sequence of the variable domain of the light chain of L6H1 is presented in SEQ ID NO:13, and the encoded amino acid sequence is presented in SEQ ID NO:14. The DNA sequence for the variable domain of the heavy chain of L6H1 is presented as SEQ ID NO:15, and the encoded amino acid sequence is presented in SEQ ID NO:16. Antibodies of the present invention include, but are not limited to, antibodies that comprise, in their light chain, residues 1 to 109 of SEQ ID NO:14; and antibodies that additionally or alternatively comprise, in their heavy chain, residues 1 to 115 of SEQ ID NO:16.

Particular embodiments of antibodies of the present invention comprise, within the variable domain of their light chain, at least one of the complementarity determining regions (CDRs), or hypervariable regions, found in the light chain of L6H1. CDRs of L6H1 are discussed in example 5. Thus, among the antibodies provided herein are those comprising from one to all three of the following sequences in the light chain variable domain: amino acid residues 24-35; residues 51-57; and residues 90-99 of SEQ ID NO:14. Particular antibodies provided herein comprise, within the variable domain of their heavy chain, at least one of the CDRs found in the heavy chain of L6H1. Thus, among the antibodies provided herein are those comprising from one to all three of the following sequences in the heavy chain variable domain: residues 31-35; residues 50-65; and residues 98-104 of SEQ ID NO:16.

In another embodiment, particular antibodies of the invention are selected from the group consisting of L2H2; an antibody that is cross-reactive with L2H2; an antibody that binds to the same epitope as L2H2; an antibody that competes with L2H2 for binding to a cell that expresses human IL-4R; an antibody that possesses a biological activity of L2H2; and an antigen-binding fragment of any of the foregoing antibodies. In one embodiment, the antibody has a binding affinity for human IL-4R that is substantially equivalent to the binding affinity of L2H2 for human IL-4R. Hybridoma cell lines that produce any such antibodies also are provided by the present invention.

One example of a biological activity of L2H2 is the ability to function as both an IL-4 antagonist and an IL-13 antagonist. In one embodiment, an antibody of the invention possesses IL-4-blocking activity substantially equivalent to that of L2H2; and possesses IL-13-blocking activity substantially equivalent to that of L2H2. Such activity may be measured in any suitable conventional assay (e.g., as measured in the CD23 expression assay described in Example 2).

The DNA sequence of the variable domain of the light chain of L2H2 is presented in SEQ ID NO:5, and the encoded amino acid sequence is presented in SEQ ID NO:6. The DNA sequence for the variable domain of the heavy chain of L2H2 is presented as SEQ ID NO:17, and the encoded amino acid sequence is presented in SEQ ID NO:18. Antibodies of the present invention include, but are not limited to, antibodies that comprise, in their light chain, residues 1 to 109 of SEQ ID NO:6; and antibodies that additionally or alternatively comprise, in their heavy chain, residues 1 to 115 of SEQ ID NO:18.

Particular embodiments of antibodies of the present invention comprise, within the variable domain of their light chain, at least one of the complementarity determining regions (CDRs), or hypervariable regions, found in the light chain of L2H2. CDRs of L2H2 are discussed in example 5. Thus, among the antibodies provided herein are those comprising from one to all three of the following sequences in the light chain variable domain: amino acid residues 24-35; residues 51-57; and residues 90-99 of SEQ ID NO:6. Particular antibodies provided herein comprise, within the variable domain of their heavy chain, at least one of the CDRs found in the heavy chain of L2H2. Thus, among the antibodies provided herein are those comprising from one to all three of the following sequences in the heavy chain variable domain: residues 31-35; residues 50-65; and residues 98-104 of SEQ ID NO:18.

In another embodiment, particular antibodies of the invention are selected from the group consisting of L2H3; an antibody that is cross-reactive with L2H3; an antibody that binds to the same epitope as L2H3; an antibody that competes with L2H3 for binding to a cell that expresses human IL-4R; an antibody that possesses a biological activity of L2H3; and an antigen-binding fragment of any of the foregoing antibodies. In one embodiment, the antibody has a binding affinity for human IL-4R that is substantially equivalent to the binding affinity of L2H3 for human IL-4R. Hybridoma cell lines that produce any such antibodies also are provided by the present invention.

One example of a biological activity of L2H3 is the ability to function as both an IL-4 antagonist and an IL-13 antagonist. In one embodiment, an antibody of the invention possesses IL-4-blocking activity substantially equivalent to that of L2H3; and possesses IL-13-blocking activity substantially equivalent to that of L2H3. Such activity may be measured in any suitable conventional assay (e.g., as measured in the CD23 expression assay described in Example 2).

The DNA sequence of the variable domain of the light chain of L2H3 is presented in SEQ ID NO:5, and the encoded amino acid sequence is presented in SEQ ID NO:6. The DNA sequence for the variable domain of the heavy chain of L2H3 is presented as SEQ ID NO:19, and the encoded amino acid sequence is presented in SEQ ID NO:20. Antibodies of the present invention include, but are not limited to, antibodies that comprise, in their light chain, residues 1 to 109 of SEQ ID NO:6; and antibodies that additionally or alternatively comprise, in their heavy chain, residues 1 to 115 of SEQ ID NO:20.

Particular embodiments of antibodies of the present invention comprise, within the variable domain of their light chain, at least one of the complementarity determining regions (CDRs), or hypervariable regions, found in the light chain of L2H3. CDRs of L2H3 are discussed in example 5. Thus, among the antibodies provided herein are those comprising from one to all three of the following sequences in the light chain variable domain: amino acid residues 24-35; residues 51-57; and residues 90-99 of SEQ ID NO:6. Particular antibodies provided herein comprise, within the variable domain of their heavy chain, at least one of the CDRs found in the heavy chain of L2H3. Thus, among the antibodies provided herein are those comprising from one to all three of the following sequences in the heavy chain variable domain: residues 31-35; residues 50-65; and residues 98-104 of SEQ ID NO:20.

In another embodiment, particular antibodies of the invention are selected from the group consisting of L2H6; an antibody that is cross-reactive with L2H6; an antibody that binds to the same epitope as L2H6; an antibody that competes with L2H6 for binding to a cell that expresses human IL-4R; an antibody that possesses a biological activity of L2H6; and an antigen-binding fragment of any of the foregoing antibodies. In one embodiment, the antibody has a binding affinity for human IL-4R that is substantially equivalent to the binding affinity of L2H6 for human IL-4R. Hybridoma cell lines that produce any such antibodies also are provided by the present invention.

One example of a biological activity of L2H6 is the ability to function as both an IL-4 antagonist and an IL-13 antagonist. In one embodiment, an antibody of the invention possesses IL-4-blocking activity substantially equivalent to that of L2H6; and possesses IL-13-blocking activity substantially equivalent to that of L2H6. Such activity may be measured in any suitable conventional assay (e.g., as measured in the CD23 expression assay described in Example 2).

The DNA sequence of the variable domain of the light chain of L2H6 is presented in SEQ ID NO:5, and the encoded amino acid sequence is presented in SEQ ID NO:6. The DNA sequence for the variable domain of the heavy chain of L2H6 is presented as SEQ ID NO:25, and the encoded amino acid sequence is presented in SEQ ID NO:26. Antibodies of the present invention include, but are not limited to, antibodies that comprise, in their light chain, residues 1 to 109 of SEQ ID NO:6; and antibodies that additionally or alternatively comprise, in their heavy chain, residues 1 to 115 of SEQ ID NO:26.

Particular embodiments of antibodies of the present invention comprise, within the variable domain of their light chain, at least one of the complementarity determining regions (CDRs), or hypervariable regions, found in the light chain of L2H6. CDRs of L2H6 are discussed in example 5. Thus, among the antibodies provided herein are those comprising from one to all three of the following sequences in the light chain variable domain: amino acid residues 24-35; residues 51-57; and residues 90-99 of SEQ ID NO:6. Particular antibodies provided herein comprise, within the variable domain of their heavy chain, at least one of the CDRs found in the heavy chain of L2H6. Thus, among the antibodies provided herein are those comprising from one to all three of the following sequences in the heavy chain variable domain: residues 31-35; residues 50-65; and residues 98-104 of SEQ ID NO:26.

In another embodiment, particular antibodies of the invention are selected from the group consisting of L2H7; an antibody that is cross-reactive with L2H7; an antibody that binds to the same epitope as L2H7; an antibody that competes with L2H7 for binding to a cell that expresses human IL-4R; an antibody that possesses a biological activity of L2H7; and an antigen-binding fragment of any of the foregoing antibodies. In one embodiment, the antibody has a binding affinity for human IL-4R that is substantially equivalent to the binding affinity of L2H7 for human IL-4R. Hybridoma cell lines that produce any such antibodies also are provided by the present invention.

One example of a biological activity of L2H7 is the ability to function as both an IL-4 antagonist and an IL-13 antagonist. In one embodiment, an antibody of the invention possesses IL-4-blocking activity substantially equivalent to that of L2H7; and possesses IL-13-blocking activity substantially equivalent to that of L2H7. Such activity may be measured in any suitable conventional assay (e.g., as measured in the CD23 expression assay described in Example 2).

The DNA sequence of the variable domain of the light chain of L2H7 is presented in SEQ ID NO:5, and the encoded amino acid sequence is presented in SEQ ID NO:6. The DNA sequence for the variable domain of the heavy chain of L2H7 is presented as SEQ ID NO:27, and the encoded amino acid sequence is presented in SEQ ID NO:28. Antibodies of the present invention include, but are not limited to, antibodies that comprise, in their light chain, residues 1 to 109 of SEQ ID NO:6; and antibodies that additionally or alternatively comprise, in their heavy chain, residues 1 to 115 of SEQ ID NO:28.

Particular embodiments of antibodies of the present invention comprise, within the variable domain of their light chain, at least one of the complementarity determining regions (CDRs), or hypervariable regions, found in the light chain of L2H7. CDRs of L2H7 are discussed in example 5. Thus, among the antibodies provided herein are those comprising from one to all three of the following sequences in the light chain variable domain: amino acid residues 24-35; residues 51-57; and residues 90-99 of SEQ ID NO:6. Particular antibodies provided herein comprise, within the variable domain of their heavy chain, at least one of the CDRs found in the heavy chain of L2H7. Thus, among the antibodies provided herein are those comprising from one to all three of the following sequences in the heavy chain variable domain: residues 31-35; residues 50-65; and residues 98-104 of SEQ ID NO:28.

In another embodiment, particular antibodies of the invention are selected from the group consisting of L2H8; an antibody that is cross-reactive with L2H8; an antibody that binds to the same epitope as L2H8; an antibody that competes with L2H8 for binding to a cell that expresses human IL-4R; an antibody that possesses a biological activity of L2H8; and an antigen-binding fragment of any of the foregoing antibodies. In one embodiment, the antibody has a binding affinity for human IL-4R that is substantially equivalent to the binding affinity of L2H8 for human IL-4R. Hybridoma cell lines that produce any such antibodies also are provided by the present invention.

One example of a biological activity of L2H8 is the ability to function as both an IL-4 antagonist and an IL-13 antagonist. In one embodiment, an antibody of the invention possesses IL-4-blocking activity substantially equivalent to that of L2H8; and possesses IL-13-blocking activity substantially equivalent to that of L2H8. Such activity may be measured in any suitable conventional assay (e.g., as measured in the CD23 expression assay described in Example 2).

The DNA sequence of the variable domain of the light chain of L2H8 is presented in SEQ ID NO:5, and the encoded amino acid sequence is presented in SEQ ID NO:6. The DNA sequence for the variable domain of the heavy chain of L2H8 is presented as SEQ ID NO:29, and the encoded amino acid sequence is presented in SEQ ID NO:30. Antibodies of the present invention include, but are not limited to, antibodies that comprise, in their light chain, residues 1 to 109 of SEQ ID NO:6; and antibodies that additionally or alternatively comprise, in their heavy chain, residues 1 to 115 of SEQ ID NO:30.

Particular embodiments of antibodies of the present invention comprise, within the variable domain of their light chain, at least one of the complementarity determining regions (CDRs), or hypervariable regions, found in the light chain of L2H8. CDRs of L2H8 are discussed in example 5. Thus, among the antibodies provided herein are those comprising from one to all three of the following sequences in the light chain variable domain: amino acid residues 24-35; residues 51-57; and residues 90-99 of SEQ ID NO:6. Particular antibodies provided herein comprise, within the variable domain of their heavy chain, at least one of the CDRs found in the heavy chain of L2H8. Thus, among the antibodies provided herein are those comprising from one to all three of the following sequences in the heavy chain variable domain: residues 31-35; residues 50-65; and residues 98-104 of SEQ ID NO:30.

In another embodiment, particular antibodies of the invention are selected from the group consisting of L2H9; an antibody that is cross-reactive with L2H9; an antibody that binds to the same epitope as L2H9; an antibody that competes with L2H9 for binding to a cell that expresses human IL-4R; an antibody that possesses a biological activity of L2H9; and an antigen-binding fragment of any of the foregoing antibodies. In one embodiment, the antibody has a binding affinity for human IL-4R that is substantially equivalent to the binding affinity of L2H9 for human IL-4R. Hybridoma cell lines that produce any such antibodies also are provided by the present invention.

One example of a biological activity of L2H9 is the ability to function as both an IL-4 antagonist and an IL-13 antagonist. In one embodiment, an antibody of the invention possesses IL-4-blocking activity substantially equivalent to that of L2H9; and possesses IL-13-blocking activity substantially equivalent to that of L2H9. Such activity may be measured in any suitable conventional assay (e.g., as measured in the CD23 expression assay described in Example 2).

The DNA sequence of the variable domain of the light chain of L2H9 is presented in SEQ ID NO:5, and the encoded amino acid sequence is presented in SEQ ID NO:6. The DNA sequence for the variable domain of the heavy chain of L2H9 is presented as SEQ ID NO:31, and the encoded amino acid sequence is presented in SEQ ID NO:32. Antibodies of the present invention include, but are not limited to, antibodies that comprise, in their light chain, residues 1 to 109 of SEQ ID NO:6; and antibodies that additionally or alternatively comprise, in their heavy chain, residues 1 to 115 of SEQ ID NO:32.

Particular embodiments of antibodies of the present invention comprise, within the variable domain of their light chain, at least one of the complementarity determining regions (CDRs), or hypervariable regions, found in the light chain of L2H9. CDRs of L2H9 are discussed in example 5. Thus, among the antibodies provided herein are those comprising from one to all three of the following sequences in the light chain variable domain: amino acid residues 24-35; residues 51-57; and residues 90-99 of SEQ ID NO:6. Particular antibodies provided herein comprise, within the variable domain of their heavy chain, at least one of the CDRs found in the heavy chain of L2H9. Thus, among the antibodies provided herein are those comprising from one to all three of the following sequences in the heavy chain variable domain: residues 31-35; residues 50-65; and residues 98-104 of SEQ ID NO:32.

In another embodiment, particular antibodies of the invention are selected from the group consisting of L2H10; an antibody that is cross-reactive with L2H10; an antibody that binds to the same epitope as L2H10; an antibody that competes with L2H10 for binding to a cell that expresses human IL-4R; an antibody that possesses a biological activity of L2H10; and an antigen-binding fragment of any of the foregoing antibodies. In one embodiment, the antibody has a binding affinity for human IL-4R that is substantially equivalent to the binding affinity of L2H10 for human IL-4R. Hybridoma cell lines that produce any such antibodies also are provided by the present invention.

One example of a biological activity of L2H10 is the ability to function as both an IL-4 antagonist and an IL-13 antagonist. In one embodiment, an antibody of the invention possesses IL-4-blocking activity substantially equivalent to that of L2H10; and possesses IL-13-blocking activity substantially equivalent to that of L2H10. Such activity may be measured in any suitable conventional assay (e.g., as measured in the CD23 expression assay described in Example 2).

The DNA sequence of the variable domain of the light chain of L2H10 is presented in SEQ ID NO:5, and the encoded amino acid sequence is presented in SEQ ID NO:6. The DNA sequence for the variable domain of the heavy chain of L2H10 is presented as SEQ ID NO:33, and the encoded amino acid sequence is presented in SEQ ID NO:34. Antibodies of the present invention include, but are not limited to, antibodies that comprise, in their light chain, residues 1 to 109 of SEQ ID NO:6; and antibodies that additionally or alternatively comprise, in their heavy chain, SEQ ID NO:34.

Particular embodiments of antibodies of the present invention comprise, within the variable domain of their light chain, at least one of the complementarity determining regions (CDRs), or hypervariable regions, found in the light chain of L2H10. CDRs of L2H10 are discussed in example 5. Thus, among the antibodies provided herein are those comprising from one to all three of the following sequences in the light chain variable domain: amino acid residues 24-35; residues 51-57; and residues 90-99 of SEQ ID NO:6. Particular antibodies provided herein comprise, within the variable domain of their heavy chain, at least one of the CDRs found in the heavy chain of L2H10. Thus, among the antibodies provided herein are those comprising from one to all three of the following sequences in the heavy chain variable domain: residues 31-35; residues 50-65; and residues 98-104 of SEQ ID NO:34.

In another embodiment, particular antibodies of the invention are selected from the group consisting of L2H11; an antibody that is cross-reactive with L2H11; an antibody that binds to the same epitope as L2H11; an antibody that competes with L2H11 for binding to a cell that expresses human IL-4R; an antibody that possesses a biological activity of L2H11; and an antigen-binding fragment of any of the foregoing antibodies. In one embodiment, the antibody has a binding affinity for human IL-4R that is substantially equivalent to the binding affinity of L2H11 for human IL-4R. Hybridoma cell lines that produce any such antibodies also are provided by the present invention.

One example of a biological activity of L2H11 is the ability to function as both an IL-4 antagonist and an IL-13 antagonist. In one embodiment, an antibody of the invention possesses IL-4-blocking activity substantially equivalent to that of L2H11; and possesses IL-13-blocking activity substantially equivalent to that of L2H11. Such activity may be measured in any suitable conventional assay (e.g., as measured in the CD23 expression assay described in Example 2).

The DNA sequence of the variable domain of the light chain of L2H11 is presented in SEQ ID NO:5, and the encoded amino acid sequence is presented in SEQ ID NO:6. The DNA sequence for the variable domain of the heavy chain of L2H11 is presented as SEQ ID NO:35, and the encoded amino acid sequence is presented in SEQ ID NO:36. Antibodies of the present invention include, but are not limited to, antibodies that comprise, in their light chain, residues 1 to 109 of SEQ ID NO:6; and antibodies that additionally or alternatively comprise, in their heavy chain, residues 1 to 115 of SEQ ID NO:36.

Particular embodiments of antibodies of the present invention comprise, within the variable domain of their light chain, at least one of the complementarity determining regions (CDRs), or hypervariable regions, found in the light chain of L2H11. CDRs of L2H11 are discussed in example 5. Thus, among the antibodies provided herein are those comprising from one to all three of the following sequences in the light chain variable domain: amino acid residues 24-35; residues 51-57; and residues 90-99 of SEQ ID NO:6. Particular antibodies provided herein comprise, within the variable domain of their heavy chain, at least one of the CDRs found in the heavy chain of L2H11. Thus, among the antibodies provided herein are those comprising from one to all three of the following sequences in the heavy chain variable domain: residues 31-35; residues 50-65; and residues 98-104 of SEQ ID NO:36.

Nucleic Acids

In one aspect, the present invention provides isolated nucleic acid molecules. The nucleic acids comprise, for example, polynucleotides that encode an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

DNA encoding antibody polypeptides (e.g., heavy or light chain, variable domain only or full length) may be isolated from B-cells of mice that have been immunized with IL-4R. The DNA may be isolated by conventional procedures such as polymerase chain reaction (PCR). Phage display is another example of a known technique whereby derivatives of antibodies may be prepared. In one approach, polypeptides that are components of an antibody of interest are expressed in any suitable recombinant expression system, and the expressed polypeptides are allowed to assemble to form antibody molecules.

FIG. 2 provides nucleic acid sequences encoding the variable regions of the heavy and light chain variable regions shown in FIG. 3. Due to the degeneracy of the genetic code, each of the polypeptide sequences in FIG. 3 also is encoded by a large number of other nucleic acid sequences. The present invention provides each degenerate nucleotide sequence encoding each antibody of the invention.

The invention further provides nucleic acids that hybridize to other nucleic acids (.e.g., nucleic acids comprising a nucleotide sequence of FIG. 2) under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. The basic parameters affecting the choice of hybridization conditions and guidance for devising suitable conditions are set forth by Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA.

Changes can be introduced by mutation into a nucleic acid, thereby leading to changes in the amino acid sequence of a polypeptide (e.g., an antibody) that it encodes. Mutations can be introduced by standard techniques, such as site-directed mutagenesis and PCR-mediated mutagenesis. Preferably, conservative amino acid substitutions are made at one or more predicted non-essential amino acid residues. Alternatively, mutations can be introduced randomly along all or part of the coding sequence, such as by saturation mutagenesis, and the resultant mutants can be screened for biological activity to identify mutants that retain activity (e.g., binding to IL-4 receptor). Following mutagenesis, the encoded protein can be expressed recombinantly and the activity of the protein can be determined. The mutations can be introduced into a nucleic acid without significantly altering the biological activity of a peptide that it encodes. For example, one can make nucleotide substitutions leading to amino acid substitutions at non-essential amino acid residues. In one embodiment, a nucleotide sequence provided in FIG. 2, or a desired fragment, variant, or derivative thereof, is mutated such that it encodes an amino acid sequence comprising one or more deletions or substitutions of amino acid residues that are shown in FIG. 3 to be residues where two or more sequences differ. In another embodiment, the mutagenesis inserts an amino acid adjacent to one or more amino acid residues shown in FIG. 3 to be residues where two or more sequences differ. Alternatively, mutations can be introduced into a nucleic acid that selectively change the biological activity (e.g., binding of IL-4 receptor, inhibiting IL-4 and/or IL-13, etc.) of a polypeptide that it encodes. For example, the mutation can quantitatively or qualitatively change the biological activity. Examples of quantitative changes include increasing, reducing or eliminating the activity. Examples of qualitative changes include changing the antigen specificity of an antibody.

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full length polypeptide of the invention, for example, a fragment that can be used as a probe or primer or a fragment encoding an active portion (e.g., an IL-4 receptor binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used identify a cell that expresses the polypeptide.

In another aspect, the present invention provides vectors comprising a nucleic acid encoding a polypeptide of the invention or a portion thereof. Examples of vectors include, but are not limited to, plasmids, viral vectors, non-episomal mammalian vectors and expression vectors, for example, recombinant expression vectors.

The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, Trends Biochem. Sci. 11:287, Maniatis et al., 1987, Science 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell (for example, *E. coli*) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

Derivatives, Fragments, and Muteins of Antibodies

Derivatives of antibodies directed against IL-4R may be prepared, and screened for desired properties, by any of a number of known techniques. Certain of the techniques involve isolating DNA encoding a polypeptide chain (or portion thereof) of an antibody of interest, and manipulating the DNA through recombinant DNA technology. The DNA may be fused to another DNA of interest, or altered (e.g., by mutagenesis or other conventional techniques) to add, delete, or substitute one or more amino acid residues, for example.

In one aspect, the present invention provides antigen-binding fragments of the antibodies of the invention. Such fragments can consist entirely of antibody-derived sequences or can comprise additional sequences. Examples of antigen-binding fragments include Fab and F(ab')$_2$. Other examples are provided in Lunde et al., 2002, Biochem. Soc. Trans. 30:500-06.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol Biol. 178:379-87. Single chain antibodies derived from antibodies provided herein (including but not limited to scFvs comprising the variable domain combinations L2H1, L3H1, L4H1, L5H1, L1H2, L1H3, L1H4, L1H5, L1H6, L1H7, L1H8, L1H9, L1H10, L1H11, L2H4, L2H12, L2H13, L2H14, L6H1, L2H2, L2H3, L2H6, L2H7, L2H8, L2H9, L2H10, and L2H111) are encompassed by the present invention.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lantto et al., 2002, Methods Mol. Biol. 178:303-16.

Accordingly, the antibodies of the present invention include those comprising, for example, the variable domain combinations L2H1, L3H1, L4H1, L5H1, L1H2, L1H3, L1H4, L1H5, L1H6, L1H7, L1H8, L1H9, L1H10, L1H11, L2H4, L2H12, L2H13, L2H14, L6H1, L2H2, L2H3, L2H6, L2H7, L2H8, L2H9, L2H10, and L2H11, having a desired isotype (for example, IgA, IgG1, IgG2, IgG3, IgG4, IgM, IgE, and IgD) as well as Fab or F(ab')$_2$ fragments thereof. Moreover, if an IgG4 is desired, it may also be desired to introduce a point mutation (CPSCP->CPPCP) in the hinge region as described in Bloom et al., 1997, Protein Science 6:407, incorporated by reference herein) to alleviate a tendency to form intra-H chain disulfide bonds that can lead to heterogeneity in the IgG4 antibodies.

Moreover, techniques for deriving antibodies having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., 1992, BioTechnology, 10:779.

Molecular evolution of the complementarity determining regions (CDRs) in the center of the antibody binding site has also been used to isolate antibodies with increased affinity, for example, antibodies having increased affinity for c-erbB-2, as described by Schier et al., 1996, J. Mol. Biol. 263:551. Accordingly, such techniques are useful in preparing antibodies to IL-4R.

In particular embodiments, antibodies of the present invention have a binding affinity (Ka) for IL-4R of at least $1\times10^8$. In other embodiments, the antibodies exhibit a Ka of at least $1\times10^9$, at least $1\times10^{10}$ or at least $1\times10^{11}$.

The present invention further includes multi-specific antibodies, for example, bispecific antibodies, e.g., two different epitopes of IL-4R, or an epitope of IL-4R and an epitope of IL-13R, via two different antigen binding sites or regions. Moreover, bispecific antibodies as disclosed herein can comprise an antigen binding site from one of the herein described antibodies and a second antigen binding region from another of the herein described antibodies. Alternatively, a bispecific antibody may comprise an antigen binding site from one of the herein described antibodies and a second antigen binding site from another IL-4R antibody that is known in the art (or one that can be prepared by known methods).

Numerous methods of preparing bispecific antibodies are known in the art, and discussed in U.S. patent application Ser. No. 09/839,632, filed Apr. 20, 2001 (incorporated by reference herein). Such methods include the use of hybrid-hybridomas as described by Milstein et al., 1983, Nature 305:537, and others (U.S. Pat. No. 4,474,893, U.S. Pat. No. 6,106,833), and chemical coupling of antibody fragments (Brennan et al., 1985, Science 229:81; Glennie et al., 1987, J. Immunol. 139:2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, J. Immunol. 148:1547) or other lock and key interactive domain structures as described in U.S. Pat. No. 5,582,996. Additional useful techniques include those described in Kortt et al., 1997, supra; U.S. Pat. No. 5,959,083; and U.S. Pat. No. 5,807,706.

In another aspect, the present invention provides a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or gold bead), or a molecule that binds to another molecule (e.g., biotin)), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody are albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols. US Pat. App. No. 20030195154.

Therapeutic Methods and Administration of Antibodies

Methods provided herein comprise administering an anti-IL-4R antibody to a subject, thereby reducing an IL-4-induced biological response that plays a role in a particular condition. In particular embodiments, methods of the invention involve contacting endogenous IL-4R with an anti-IL-4R antibody, e.g., in an ex vivo procedure.

Treatment encompasses alleviation or prevention of at least one symptom of a disorder, or reduction of disease severity, and the like. An antibody need not effect a complete "cure", or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. One embodiment of the invention is directed to a method comprising administering to a patient an IL-4R antagonist in an amount and for a time sufficient to induce a sustained improvement over baseline of an indicator that reflects the severity of the particular disorder.

Antibodies that inhibit the binding of both IL-4 and IL-13 to cells are discussed herein. A method for suppressing IL-4-induced and IL-13-induced activities in humans comprises administering an effective amount of such an antibody. Conditions induced by IL-4 or by IL-13, or by both cytokines, thus may be treated.

As is understood in the pertinent field, antibodies are administered to a subject in a manner appropriate to the indication. Antibodies may be administered by any suitable technique, including but not limited to parenterally, topically, or by inhalation. If injected, the antibody can be administered, for example, via intra-articular, intravenous, intramuscular, intralesional, intraperitoneal or subcutaneous routes, by bolus injection, or continuous infusion. Localized administration, e.g. at a site of disease or injury is contemplated, as are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including pills, syrups, lozenges or chewing gum; and topical preparations such as lotions, gels, sprays, and ointments.

Use of anti-IL-4R antibodies in ex vivo procedures also is contemplated. For example, a patient's blood or other bodily fluid may be contacted with an antibody that binds IL-4R ex vivo. The antibody may be bound to a suitable insoluble matrix or solid support material.

Advantageously, antibodies are administered in the form of a composition comprising at least one anti-IL-4R antibody and one or more additional components such as a physiologically acceptable carrier, excipient or diluent. The present invention provides such compositions comprising an effective amount of an anti-IL-4R antibody, for use in the methods provided herein.

The compositions contain anti-IL-4R antibody(-ies) in, for example, any of the forms described herein. The antibody may be a whole antibody or an antigen-binding fragment or engineered derivative thereof, for example.

Compositions may, for example, comprise an antibody together with a buffer, antioxidant such as ascorbic acid, low molecular weight polypeptide (such as those having fewer than 10 amino acids), protein, amino acid, carbohydrate such as glucose, sucrose or dextrins, chelating agents such as EDTA, glutathione, and other stabilizers and excipients. Neutral buffered saline or saline mixed with conspecific serum albumin are examples of appropriate diluents. In accordance with appropriate industry standards, preservatives such as benzyl alcohol may also be added. The composition may be formulated as a lyophilizate using appropriate excipient solutions (e.g., sucrose) as diluents. Suitable components are nontoxic to recipients at the dosages and concentrations employed. Further examples of components that may be employed in pharmaceutical formulations are presented in *Remington's Pharmaceutical Sciences*, 16$^{th}$ Ed., Mack Publishing Company, Easton, Pa., 1980.

Kits for use by medical practitioners include an anti-IL-4R antibody and a label or other instructions for use in treating any of the conditions discussed herein. The kit preferably includes a sterile preparation of one or more anti-IL-4R antibodies, which may be in the form of a composition as disclosed above, and may be in one or more vials.

Dosages and the frequency of administration may vary according to such factors as the route of administration, the particular antibody employed, the nature and severity of the disease to be treated, whether the condition is acute or chronic, and the size and general condition of the subject. Appropriate dosages can be determined by procedures known in the pertinent art, e.g. in clinical trials that may involve dose escalation studies.

An antibody may be administered, for example, once or more than once, e.g., at regular intervals over a period of time. In particular embodiments, the antibody is administered over a period of at least a month or more, e.g., for one, two, or three months or even indefinitely. For treating chronic conditions, long-term treatment is generally most effective. However, for treating acute conditions, administration for shorter periods, e.g. from one to six weeks, may be sufficient. In general, the antibody is administered until the patient manifests a medically relevant degree of improvement over baseline for the chosen indicator or indicators.

Particular embodiments of the present invention involve administering an antibody at a dosage of from about 1 ng of antibody per kg of subject's weight per day ("1 ng/kg/day") to about 10 mg/kg/day, more preferably from about 500 ng/kg/day to about 5 mg/kg/day, and most preferably from about 5 µg/kg/day to about 2 mg/kg/day, to a subject. In additional embodiments, an antibody is administered to adults one time per week, two times per week, or three or more times per week, to treat an IL-4 and/or IL-13 mediated disease, condition or disorder, e.g., a medical disorder disclosed herein. If injected, the effective amount of antibody per adult dose may range from 1-20 mg/m$^2$, and preferably is about 5-12 mg/m$^2$. Alternatively, a flat dose may be administered; the amount may range from 5-100 mg/dose. One range for a flat dose is about 20-30 mg per dose. In one embodiment of the invention, a flat dose of 25 mg/dose is repeatedly administered by injection. If a route of administration other than injection is used, the dose is appropriately adjusted in accordance with standard medical practices. One example of a therapeutic regimen involves injecting a dose of about 20-30 mg of anti-IL-4R antibody to one to three times per week over a period of at least three weeks, though treatment for longer periods may be necessary to induce the desired degree of improvement. For pediatric subjects (age 4-17), one exemplary suitable regimen involves the subcutaneous injection of 0.4 mg/kg, up to a maximum dose of 25 mg of antibody administered two or three times per week.

Particular embodiments of the methods provided herein involve subcutaneous injection of from 0.5 mg to 10 mg, preferably from 3 to 5 mg, of an anti-IL-4R antibody, once or twice per week. Another embodiment is directed to pulmonary administration (e.g., by nebulizer) of 3 or more mg of antibody once a week.

Examples of therapeutic regimens provided herein comprise subcutaneous injection of an anti-IL-4R antibody once a week, at a dose of 1.5 to 3 mg, to treat asthma. pulmonary sarcoidosis, minimal change nephrosis, autoimmune uveitis, sickle cell crisis, Churg-Strauss syndrome, Sjogren's syndrome, autoimmune lymphoproliferative syndrome, pre-eclampsia, autoimmune hemolytic anemia, Barrett's esophagus, Grave's Disease, Kawasaki Disease, and cavitary tuberculosis. Weekly administration of anti-IL-4R antibody is continued until a desired result is achieved, e.g., the subject's symptoms subside. Treatment may resume as needed, or, alternatively, maintenance doses may be administered.

In another embodiment, an antibody is administered to the subject in an amount and for a time sufficient to induce an improvement, preferably a sustained improvement, in at least one indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question. In most instances, an improvement is considered to be sustained if the subject exhibits the improvement on at least two occasions separated by two to four weeks. The degree of improvement generally is determined by a physician, who may make this determination based on signs or symptoms, and who may also employ questionnaires that are administered to the subject, such as quality-of-life questionnaires developed for a given disease.

As one example, in treating benign prostate hyperplasia, an anti-IL-4R antibody is administered to the subject in an amount and for a time effective in scar regression or complete healing. Maintenance doses may be given or treatment resumed as needed.

Elevated levels of IL-4 are associated with a number of disorders, as discussed above. Subjects with a given disorder may be screened, to identify those individuals who have elevated IL-4 levels, or to identify those with an elevated TH2-type immune response, thereby identifying the subjects who may benefit most from treatment with an anti-IL-4R antibody. Thus, treatment methods provided herein optionally comprise a first step of measuring a subject's IL-4 level. An anti-IL-4R antibody may be administered to a subject in whom IL-4 levels are elevated above normal. Alternatively or additionally, a subject may be pre-screened to determine whether the subject has an elevated TH2-type immune response, prior to administration of antibody(-ies) and/or antagonist(s) against one or more TH2-type cytokines.

A subject's levels of IL-4 (and, optionally, of other TH2-type cytokines) may be monitored during and/or after treatment with an anti-IL-4R antibody, to detect reduction in the levels of the cytokines. For some disorders, the incidence of elevated IL-4 levels, and the balance between TH1-type and TH2-type immune responses, may vary according to such factors as the stage of the disease or the particular form of the disease. Known techniques may be employed for measuring IL-4 levels, e.g., in a subject's serum, and for assessing TH2- type immune responses. Cytokine levels in blood samples may be measured by ELISA, or by a LUMINEX™ multi-plex cytokine assay (Luminex Corporation, Austin, Tex.) or DELFIA® (PerkinElmer LifeSciences, Wallac Oy., Turku, Finland), for example.

Particular embodiments of methods and compositions of the invention involve the use of an anti-IL4R antibody and one or more additional IL-4R antagonists, for example, two or more antibodies or antibody derivatives of the invention, or an antibody or antibody derivative of the invention and one or more other IL-4R antagonists. In further embodiments, anti-IL-4R antibodies are administered alone or in combination with other agents useful for treating the condition with which the patient is afflicted. Examples of such agents include both proteinaceous and non-proteinaceous drugs. When multiple therapeutics are co-administered, dosages may be adjusted accordingly, as is recognized in the pertinent art. "Co-administration" and combination therapy are not limited to simultaneous administration, but include treatment regimens in which an IL-4R antibody is administered at least once during a course of treatment that involves administering at least one other therapeutic agent to the patient.

Examples of other agents that may be co-administered with IL-4R antibodies are other antibodies, cytokines, or cytokine receptors, which are chosen according to the particular condition to be treated. Alternatively, non-proteinaceous drugs that are useful in treating one of the particular conditions discussed above may be co-administered with an IL-4R antagonist.

For treating IgE-mediated conditions, an anti-IL-4R antibody may be co-administered with an IgE antagonist. One example is an anti-IgE antibody, e.g., XOLAIR® (Genentech, South San Francisco, Calif.). Humanized anti-IgE monoclonal antibodies are described in, for example, Presta et al., 1993, J. Immunol. 151:2623-32 and Adelroth et al., 2000, J. Allergy Clin. Immunol. 106:253-59.

Anti-IL-4R antibodies may be co-administered with an IL-5 antagonist, which may be a molecule that interferes with the binding of IL-5 to an IL-5 receptor, such as an anti-IL-5R or anti-IL-5 antibody (e.g., a human or humanized anti-IL-5 or anti-IL-5R monoclonal antibody), or a receptor such as a soluble human IL-5 receptor polypeptide. IL-5 has been implicated as playing a role in mediating allergic responses. Thus, administration of antagonist(s) of IL-4R and IL-5 is contemplated for treatment of allergic reactions, including but not limited to allergic asthma.

Further examples of agents that can be used in conjunction with IL-4R antibodies include anti-IL-4 antibodies, IL-4 muteins, IL-4 binding derivatives of IL-4R (as described in, e.g., U.S. Pat. Nos. 5,840,869; 5,599,905, 5,856,296, 5,767,065, 5,717,072, 6,391,581, 6,548,655, 6,472,179, and 5,844,099), IL-13 binding derivatives of IL-13, IL-4 and/or IL-13 binding chimeric derivatives of IL-4R and IL-13R, IL-13 muteins, and antagonists of CD23 (e.g., anti-CD23 antibodies such as IDEC-152™ (IDEC Pharmaceuticals, San Diego, Calif.), Phosphodiesterase 4 (e.g., ROFLUMILAST®, Byk Gulden Pharmaceuticals, Konstanz, Germany), integrins (e.g., R411™, Roche, Nutley, N.J.), TIMs, Gob5, STATE, and leukotrienes.

For treating asthma, an IL-4R antibody may be co-administered with other anti-asthma medications, such as inhaled corticosteroids, beta agonists, leukotriene antagonists, xanthines, fluticasone, salmeterol, albuterol, non-steroidal agents such as cromolyn, and the like. IL-4R antibodies may be co-administered with other anti-allergy medications to treat allergic reactions.

One embodiment of the present invention is directed to co-administration of an antibody or antibody derivative of the invention and fluticasone and/or salmeterol to treat a disorder such as asthma. Compositions comprising an antibody or antibody derivative of the invention, fluticasone, and salmeterol are provided herein. ADVAIR DISKUS® (GlaxoSmithKline, Research Triangle Park, N.C.) comprises fluticasone propionate and salmeterol xinafoate. ADVAIR DISKUS® and the antibody or antibody derivative can be delivered by any route of administration effective for treating or preventing a particular disease, disorder, injury, or condition e.g., by inhalation for treating asthma.

Another example of combination therapy comprises co-administration of an antibody or antibody derivative of the invention and an IL-9 antagonist to a patient who has asthma. Any suitable IL-9 antagonist may be employed, such as an IL-9 receptor (e.g., a soluble form thereof), an antibody that interferes with binding of IL-9 to a cell surface receptor (e.g., an antibody that binds to IL-9 or to an IL-9 receptor polypeptide), or another compound that inhibits IL-9-induced biological activity. IL-9 receptors include those described in WO 93/18047 and U.S. Pat. Nos. 5,789,237 and 5,962,269, which are hereby incorporated by reference herein.

In an additional embodiment of combination therapy, a method for treating ulcerative colitis comprises co-administration of an antibody or antibody derivative of the invention and at least one IL-1 antagonist. Examples of IL-1 antagonists include type I IL-1 receptor, type II IL-1 receptor, IL-1 receptor antagonist (IL-1Ra), antagonistic (blocking) antibodies directed against IL-1, and antagonistic antibodies directed against an IL-1 receptor. Various forms of the receptors may be employed, such as fragments, variants and fusions, for example, a soluble form of type II IL-1 receptor, e.g., as described in U.S. Pat. No. 5,350,683, hereby incorporated by reference herein.

One method of the present invention comprises co-administering an antibody or antibody derivative of the present invention, alone or in combination with an IL-13 antagonist(s), to a patient who has minimal change nephrosis, e.g., to reduce severity of the disease.

Another method provided herein is a method for treating various allergic inflammatory conditions, comprising co-administering an antibody or antibody derivative of the invention and IL-13 antagonist(s). Conditions such as asthma, allergies, and chronic lung diseases such as cystic fibrosis and chronic obstructive pulmonary disease are treated by such a method.

Any suitable IL-13 antagonist may be employed, including but not limited to IL-13 receptors (preferably soluble forms thereof), IL-13 receptor antagonists, antibodies directed against IL-13 or an IL-13R, other proteins that interfere with the binding of IL-13 to an IL-13R, and compounds that inhibit IL-13-mediated signal transduction. IL-13 receptors and heterodimers comprising IL-13R polypeptides as components thereof are described above. Antibodies that are raised against IL-4R may be screened for the ability to also function as IL-13 antagonists, as discussed above.

A method for treating or preventing a condition characterized by reduced epithelial barrier function comprises co-administering an antibody or antibody derivative of the invention and one or more IL-13 antagonists. Such conditions are discussed above. In one embodiment, the condition is asthma. Particular embodiments are directed to co-administering one or more antibodies or antibody derivatives of the invention and one or more IL-13 antagonists to a patient having a condition involving reduction of lung epithelial barrier function or intestinal epithelial barrier function, wherein both IL-4 and IL-13 play a role in the reduced barrier function. The adverse effect of IL-13 on lung and intestinal epithelial barrier function can be confirmed using assay techniques such as those described in Example 3. See also Zund et al., 1996, J. Biol. Chem. 271:7460-64.

Another method provided herein comprises co-administering an antibody or antibody derivative of the invention and interferon-γ (IFN-γ) to a patient having a condition involving reduction of lung epithelial barrier function. Optionally, such a method further comprises co-administering one or more IL-13 antagonists to the patient (i.e., co-administering an antibody or antibody derivative of the invention, IFN-γ, and an IL-13 antagonist). In one embodiment, the patient has asthma. The antibody or antibody derivative of the invention, IFN-γ, and/or IL-13 antagonist can be administered via any method of delivery effective for treating or preventing a particular disease, disorder, condition, or injury, e.g., for treating asthma, via inhalation or injection.

One method provided herein for treating asthma comprises administering an antibody or antibody derivative of the invention and interferon-γ to a human who has asthma. Another method for treating asthma comprises co-administering an antibody or antibody derivative of the invention, IFN-γ, and an IL-13 antagonist to a human who has asthma. In one embodiment, IFN-γ is co-administered to an asthmatic, together with an antibody that functions as an antagonist of both IL-4 and IL-13. Examples of such antibodies are described elsewhere herein.

A single antibody or antibody derivative of the invention may function as an IL-4 antagonist and an IL-13 antagonist, as discussed above. As an example of such an agent, some antibodies raised against IL-4Rα may interfere with the binding of both IL-4 and IL-13 receptor complexes, due to the shared IL-4Rα component in such multi-subunit receptor complexes (discussed above). Thus, a single antibody or antibody derivative of the invention may be employed in a method for inhibiting reduction of barrier function.

An antibody or antibody derivative of the invention may be co-administered with one or more leukotriene receptor antagonists to treat disorders such as allergic inflammatory diseases, e.g., asthma and allergies. Examples of leukotriene receptor antagonists include but are not limited to montelukast (e.g., SINGULAIR®, Merck & Co., Whitehouse, N.J.), pranlukast (e.g., ONON®, Ono Pharmaceuticals, Osaka, Japan), and zafirlukast (e.g., ACCOLATE®, AstraZeneca, Wilmington, Del.). Drugs that function as 5-lipoxygenase inhibitors may be co-administered with an IL-4R antagonist to treat asthma.

Methods provided herein comprise administering an antibody or antibody derivative of the invention and one or more of the following to Churg-Strauss Syndrome patients: IL-4R antagonist(s), IL-5 antagonist(s), IL-13 antagonist(s) and IgE antagonist(s). One example of such a method involves co-administering an antibody or antibody derivative of the invention and IL-5 antagonist(s) to a Churg-Strauss Syndrome patient. In another embodiment, an antibody or antibody derivative of the invention and IgE antagonist(s) are co-administered to the patient. In yet another embodiment, an antibody or antibody derivative of the invention and IL-13 antagonist(s) are co-administered to the patient.

The hormone relaxin may be co-administered with an antibody or antibody derivative of the invention to treat scleroderma (systemic sclerosis), idiopathic pulmonary fibrosis, or any other disorder characterized by pulmonary fibrosis, such as the conditions involving fibrosis of the lung that are discussed above. Recombinant human relaxin is preferred for use in treating humans.

A method for treating benign prostate hyperplasia comprises co-administering an antibody or antibody derivative of the invention and one or more additional anti-inflammatory agents. Examples of agents that inhibit inflammation include tumor necrosis factor (TNF) antagonists and IL-17 antagonists.

Any suitable IL-17 antagonist may be employed, including but not limited to an IL-17 receptor (e.g., soluble forms thereof), IL-17 receptor antagonists, antibodies directed against IL-17 or an IL-17 receptor, other proteins that interfere with the binding of IL-17 to an IL-17 receptor, and compounds that inhibit IL-17-mediated signal transduction. An IL-17 receptor, including soluble forms thereof and oligomers thereof, is described in WO 96/29408, hereby incorporated by reference. An alternative method provided herein comprises administering an IL-17 antagonist to treat a patient with benign prostate hyperplasia.

Likewise, any suitable TNF antagonist may be employed, including but not limited to a TNF receptor (preferably soluble forms thereof), fusion proteins comprising a TNF receptor (or comprising the TNF-binding portion of a TNF receptor), TNF receptor antagonists, antibodies directed against TNF or a TNF receptor, other proteins that interfere with the binding of TNF to a TNF receptor, and compounds that inhibit TNF-mediated signal transduction. Further examples of TNF inhibitors are the drugs thalidomide and pentoxifylline. The TNF receptor protein known as p75 or p80 TNF-R preferably is employed. A preferred TNF antagonist is a soluble human TNF receptor (sTNF-R) in dimeric form, such as dimers of sTNF-R/Fc fusion proteins. One such dimer is etanercept (ENBREL®, Immunex Corporation, Seattle, Wash.). p75/p80 TNF-R, including soluble fragments and other forms thereof, is described in WO 91/03553, hereby incorporated by reference herein.

Accordingly, in one embodiment of the present invention, an antibody or antibody derivative of the invention is co-administered with a TNF antagonist to treat any condition in which undesirable IL-4R-mediated and TNF-induced immune responses play a role, such as inflammation. One method provided herein comprises co-administering an antibody or antibody derivative of the invention and a TNF antagonist to a patient with inflammatory bowel disease, Crohn's disease, or ulcerative colitis. Other embodiments are directed to a method comprising co-administering an antibody or antibody derivative of the invention and a TNF antagonist to a patient who has Kawasaki Disease, autoimmune hemolytic anemia, autoimmune uveoretinitis, autoimmune lymphoproliferative syndrome, Sjogren's syndrome, chronic fatigue syndrome, or hepatotoxicity induced by a drug such as diclofenac.

Another method provided herein comprises co-administering an antibody or antibody derivative of the invention and a TNF antagonist to a pregnant woman who has developed pre-eclampsia. In one embodiment, the administration of the antibody or antibody derivative of the invention TNF-antagonist continues for the duration of the pregnancy.

Suitable dosages of etanercept will vary according to the nature of the disease to be treated, disease severity, the size of the patient (e.g., adult or child), and other factors, as is recognized in the pertinent field. In one embodiment of the methods provided herein, ENBREL® is administered twice a week by subcutaneous injection at a dose of from 1 to 25 mg. One embodiment of a pediatric dosage is 0.4 mg/kg. Particular methods provided herein comprise co-administration of an antibody or antibody derivative of the invention and ENBREL® to a patient has autoimmune lymphoproliferative syndrome or Sjogren's syndrome, wherein ENBREL® is given by subcutaneous injection at a dose of from 1 to 25 mg.

For treating graft versus host disease ("GVHD"), an antibody or antibody derivative of the invention is co-administered with at least one of the following agents: a TNF antagonist, an IL-1 antagonist, steroids, or corticosteroids. In one embodiment, the TNF inhibitor is ENBREL®. In another embodiment, the IL-1 antagonist is a soluble form of type II IL-1 receptor, e.g., as described in U.S. Pat. No. 5,350,683. In another embodiment, the GVHD is associated with (e.g., develops subsequent to) bone marrow transplantation. An antibody or antibody derivative of the invention may be employed in combination with at least one of the above-listed agents, in methods for suppressing an immune response directed against transplanted cells, tissue, and/or alloantigen.

A number of cytokine antagonists and other agents/drugs are disclosed herein as being useful for combination therapy (e.g., co-administration with an antibody or antibody derivative of the invention) in treating particular diseases. It is to be understood that such antagonists, agents, or drugs also find use as single agents in treating those diseases. It also is to be understood that disclosure of methods involving administration of an antagonist to a particular cytokine, to treat a disease, encompasses administration of one type of antagonist, and also encompasses administration of two or more different antagonists for that cytokine, unless specified otherwise.

Example 1

Preparation of Monoclonal Antibodies

This example demonstrates a method of preparing monoclonal antibodies recognizing the human IL-4 receptor.

IL-4 receptor polypeptides may be employed as immunogens in generating monoclonal antibodies by conventional techniques, e.g., techniques described in U.S. Pat. No. 5,599,905, hereby incorporated by reference in its entirety. It is recognized that polypeptides in various forms may be employed as immunogens, e.g., full length proteins, fragments thereof, fusion proteins thereof such as Fc fusions, cells expressing the recombinant protein on the cell surface, etc.

To summarize an example of such a procedure, an IL-4R immunogen emulsified in complete Freund's adjuvant is injected subcutaneously into Lewis rats, in amounts ranging from 10-100 μl. Three weeks later, the immunized animals are boosted with additional immunogen emulsified in incomplete Freund's adjuvant and boosted every three weeks thereafter. Serum samples are periodically taken by retro-orbital bleeding or tail-tip excision for testing by dot-blot assay, ELISA (enzyme-linked immunosorbent assay), or inhibition of binding of $^{125}$I-IL-4 to extracts of IL-4R-expressing cells. Following detection of an appropriate antibody titer, positive animals are given a final intravenous injection of antigen in saline. Three to four days later, the animals are sacrificed, splenocytes harvested, and fused to the murine myeloma cell line AG8653. The resulting hybridoma cell lines are plated in multiple microtiter plates in a HAT selective medium (hypoxanthine, aminopterin, and thymidine) to inhibit proliferation of non-fused cells, myeloma hybrids, and spleen cell hybrids.

Hybridoma clones thus generated are screened for reactivity with IL-4R. Initial screening of hybridoma supernatants utilizes an antibody capture and binding of partially purified $^{125}$I-IL-4 receptor. Hybridomas that are positive in this screening method are tested by a modified antibody capture to detect hybridoma cells lines that are producing blocking antibody. Hybridomas that secrete a monoclonal antibody capable of inhibiting $^{125}$I-IL-4 binding to cells expressing IL-4R are thus detected. Such hydridomas then are injected into the peritoneal cavities of nude mice to produce ascites containing high concentrations (>1 mg/ml) of anti-IL-4R monoclonal antibody. The resulting monoclonal antibodies may be purified by ammonium sulfate precipitation followed by gel exclusion chromatography, and/or affinity chromatography based on binding of antibody to Protein G.

Methods for generating human antibodies in transgenic mice have been described and are well known in the art. See, e.g., Chen et al., 1993, Internat. Immunol. 5: 647-56; Chen et al., 1993, EMBO J. 12: 821-30; Choi et al., 1993, Nature Genetics 4: 117-23; Fishwild et al., 1996, Nature Biotech. 14: 845-51; Harding et al., 1995, Annals New York Acad. Sci.; Lonberg et al., 1994, Nature 368: 856-59; Lonberg, 1994, Handbook Exper. I Pharmacol. 113: 49-101; Lonberg et al., 1995, Internal Rev. Immunol. 13: 65-93; Morrison, S, 1994, Nature 368: 812-13; Neuberger, 1996, Nature Biotech. 14: 826; Taylor et al., 1992, Nuc. Acids Res. 20: 6287-95; Taylor et al., 1994, Internat. Immunol. 6: 579-91; Tomizuka et al., 1997, Nature Genetics 16: 133-43; Tomizuka et al., 2000, Proc. Nat. Acad. Sci. USA 97: 722-27; Tuaillon et al., 1993, Proc. Nat. Acad. Sci. USA 90: 3720-24; Tuaillon et al., 1994, J. Immunol. 152: 2912-20; Russel et al., 2000, Infection and Immunity April 2000: 1820-26; Gallo et al., 2000, Eur. J. Immunol. 30: 534-40; Davis et al., 1999, Cancer Metastasis Rev. 18:421-25; Green, 1999, J. Immunol. Methods 231:11-23; Jakobovits, 1998, Advanced Drug Delivery Rev. 31:33-42; Green et al., 1998, J. Exp. Med. 188: 483-95; Jakobovits, 1998, Exp. Opin. Invest. Drugs 7: 607-14; Tsuda et al., 1997, Genomics 42: 413-21; Mendez et al., 1997, Nature Genetics 15: 146-56; Jakobovits, 1996, Weir's Handbook of Experimental Immunology, The Integrated Immune System Vol. IV, 194.1-194.7; Mendez et al., 1995, Genomics 26: 294-307; Jakobovits, 1994, Current Biol. 4: 761-63; Arbones, 1994, Immunity 1: 247-60; Green et. al., 1994, Nature Genetics 7: 13-21; Jakobovits et al., 1993, Nature 362: 255-58; Jakobovits et al., 1993, Proc. Nat. Acad. Sci. USA 90: 2551-55.

Example 2

Assay for Assessing Blocking Activity

This example demonstrates an assay that can be used to identify antibodies that reduce IL-4 and/or IL-13-dependent expression of CD23. The assay is based on the ability of both IL-4 and IL-13 to enhance the expression of the activation-associated surface antigen CD23 on human B cells.

Antibodies raised against human IL-4R (huIL-4R) are tested either in the form of hybridoma supernatants or purified protein. Prior to addition to cultures, the antibodies are buffer exchanged against culture medium (RPMI 1640 plus 10% heat-inactivated fetal bovine serum) by centrifugation, using Centricon filter devices (Amicon) with a 10 kDa cutoff.

Human peripheral blood B cells are purified as described previously (Morris et al., 1999, J. Biol. Chem. 274:418-23). The B cells ($3 \times 10^5$/well) in culture medium are placed in 96-well round-bottomed microtiter plates and preincubated at room temperature for 30 min with test antibodies at the final concentrations indicated. Recombinant human IL-4 or IL-13 is then added to the cultures at the concentrations indicated, and cells are cultured for 20-24 hours at 37° C. in a humidified atmosphere of 5% $CO_2$. At the end of the culture period, cells are washed once in PBS+0.02% $NaN_3$ in the 96-well culture plate and are resuspended in blocking buffer (2% normal rabbit serum+1% normal goat serum in PBS+$NaN_3$). Phycoerythrin (PE)-conjugated CD23 monoclonal antibody (mAb)

or PE-conjugated isotype control mAb (both from Pharmingen) are then added to cells at a final dilution of 1:10. Cells are incubated for 30 minutes at 4° C., washed ×3 in PBS+NaN$_3$ and analyzed on a FacScan (Becton Dickinson) for CD23 expression.

Cells cultured with hybridoma growth medium or isotype-matched non-blocking human anti-hIL-4R antibody are included as negative controls. An anti-huIL-4R murine mAb (MAB 230, R&D Systems, Minneapolis, Minn.), previously shown to block the binding and function of both hIL-4 and hIL-13, is used as a positive control for neutralization of CD23 induction by IL-4 and IL-13.

Example 3

Assays for Measuring Loss of Barrier Function

This example provides methods of assessing the ability of an IL-4 antagonist to inhibit IL-4 induced damage to epithelial tissue and loss of epithelial barrier function.

In one aspect, the present invention provides a method of using an IL-4 antagonist to inhibit IL-4-induced damage to epithelium, including but not limited to lung epithelium or intestinal epithelium. Damage to epithelium can result in loss of barrier function. The following are non-limiting examples of techniques that may be employed in assessing the ability of an IL-4 antagonist to inhibit IL-4-induced damage to epithelium and loss of epithelial barrier function.

Cells that may be employed in preparing in vitro models of epithelium (epithelial barriers) are known. For example, Calu-3 human lung epithelial cells are suitable for use in barrier function studies (Ahdieh et al., 2001, Am. J. Physiol. Cell Physiol. 281:C2029-38). Another suitable cell line is the human intestinal epithelial cell line designated T84. T84 cells are cultured under conditions that result in formation of a monolayer of epithelial cells on a permeable support, as described in Madara et al., 1985, J. Cell Biol., 101:2124-33, Madara et al., 1989, J. Clin. Invest. 83:724-27, and Youakim et al., 1999, Am. J. Physiol. 276 (Gastrointest. Liver Physiol. 39):G1279-88. The thus-generated epithelial monolayer simulates the intestinal epithelial barrier.

The cultured monolayers are tested for a property (e.g., resistance to passive transepithelial ion flow) that can distinguish an intact epithelium from a damaged epithelium. One such assay determines whether a particular radiolabeled compound is able to cross an epithelial monolayer. Leakage of the radiolabeled compound through the monolayer indicates that the barrier is permeable rather than intact. For example, mannitol flux analysis can be used to detect epithelial damage by assessing the movement of radiolabeled mannitol (e.g., $^3$H mannitol) across a monolayer (see Madara and Stafford, supra).

Other examples of methods for assessing the condition of an epithelial include imaging methods (e.g., those discussed in Madara and Stafford, supra) and transepithelial electrical resistance measurements (e.g., those discussed in Youakim and Ahdieh, supra).

U.S. Pat. No. 6,033,688 ("the '688 patent"), incorporated herein by reference in its entirety, also describes procedures that may be employed in studies of barrier permeability; see, e.g., Examples 1 and 4 of the patent. Human tracheal epithelial cells are cultured under conditions that yield a monolayer exhibiting transepithelial electrical resistance. Transepithelial resistance (indicating an intact barrier) is determined using a voltmeter. The effect of a substance or treatment on the epithelial monolayer is assessed by exposing the monolayer to the substance or treatment, and then measuring ion transport activities in Ussing chambers (column 8, lines 40-56). Similar procedures can be conducted using monolayers that are generated from other types of cells, e.g., bronchial epithelial cells from a human cystic fibrosis patient (see the '688 patent, example 4, column 11).

Thus, the ability of a substance's or treatment's ability to inhibit IL-4-induced reduction in the barrier function of an epithelial layer can be assessed by exposing the epithelial layer to IL-4 and to the substance or treatment, assaying the condition of the epithelial layer, and comparing the condition of the epithelial layer to the condition of an epithelial layer that has been exposed to IL-4 in the absence of the substance or condition. An improvement in the condition of the epithelial layer exposed to the substance or treatment relative to an epithelial layer not exposed to the substance or treatment indicates that the substance or treatment to inhibits IL-4 induced damage to epithelial tissue and loss of epithelial barrier function.

In one such assay, a monolayer of T84 cells served as an in vitro model of an intestinal epithelial barrier, as discussed above. IL-4 added to the basolateral side of polarized epithelial cells was found to reduce barrier function by 70% within 48-72 hours of treatment. When a soluble IL-4 receptor polypeptide consisting of the extracellular domain was added at the same time as IL-4, the reduction in barrier function was prevented, and the barrier was maintained at the same level as untreated (control) cells.

The assay procedure also was conducted on a monolayer derived from lung epithelial cells, which served as an in vitro model of a lung epithelial barrier. IL-4 added to the basolateral side of polarized lung epithelial cells was found to reduce barrier function by 50% within 48-72 hours of treatment. When the IL-4 receptor polypeptide was added at the same time as IL-4, the reduction in barrier function was prevented, and the barrier was maintained at the same level as untreated (control) cells.

Example 4

Assays for Measuring Binding Activity

This example provides methods of assessing the binding activity of an anti-IL-4R antibody.

Anti-huIL-4R (or a variant, derivative, or fragment thereof), is radiolabeled with $^{125}$I using a solid phase chloramine-T analogue (IODOGEN®, Pierce, St. Louis, Mo.) or other, suitable radiolabeling technique, to a specific activity of approximately $3 \times 10^{16}$ cpm/mmol. Loss of bioactivity is assessed by comparing binding inhibition or other biological inhibition assay with the corresponding unlabeled protein. Alternatively, inhibition of radiolabeled IL-4 binding by anti-huIL-4R (or a variant or fragment thereof) can be measured. Equilibrium binding assays on cells expressing IL-4R are performed in 96-well microtiter trays substantially as described in Idzerda, et al., 1990, J. Exp. Med. 171:3 861-73. Briefly, serial dilutions of radiolabeled protein in binding medium (RPMI 1640, 2.5% BSA, 20 mM HEPES, 0.02% sodium azide, pH 7.2), supplemented with 0.5 mg/ml human IgG and 5% human serum), are incubated with cells (2.5×106/well) for 2 hours at 4° C. in a total volume of 150 microliters. Free and bound radiolabeled probes are separated by microfugation through a phthalate-oil separation mixture and counted in a gamma counter. Inhibition assays use radiolabeled protein at a constant concentration of 0.5 nM in the presence or absence of potential inhibitors. Nonspecific binding is determined in the presence of a 100-fold excess of unlabeled protein. Theoretical curves based on single-site competitive inhibition model are fitted to the data as described in Dower et al., 1984, J. Immunol. 132:751. Percent inhibition is calculated according to the equation $I(\%)=[100 \, Ki(I)/[1+Ka(L)+Ki(I)]$, where I is the molar concentration of inhibitor, L is the molar concentration of radiolabeled protein, and Ki and Ka are the affinity constants of inhibitor and protein, respectively.

Equilibrium binding and competitive inhibition isotherms may also determined in 96-well microtiter plates coated with IL-4R/Fc or a control Fc protein, captured through goat anti-human Fc polyclonal antibody (or other suitable anti-human Fc antibody). Briefly, plates are incubated with 5 micrograms/ml anti-human Fc in PBS at 4° C., washed twice with PBS, and then incubated with IL-4R/Fc or a control Fc protein in PBS/0.01% Tween 20 for about 12 hours at 4° C. and washed again twice with PBS. Equilibrium binding isotherms use serial dilutions of $^{125}$I-labeled binding protein in binding medium, and inhibition assays use a constant of 0.5 nM $^{125}$I-labeled anti-huIL-4R in the presence or absence of unlabeled, potential competitive inhibitors, as described above. After 2 hours at 4° C., plates are washed twice in PBS, and specifically bound protein is released with 50 mM citrate (pH 3.0), or SDS treatment, and released $^{125}$I-labeled anti-huIL-4R measured on a gamma counter. Data are processed as described in Dower et al., supra.

Binding activity may also be assessed by surface plasmon resonance using a BIACORE® biosensor (BIAcore International AB, Uppsala, Sweden). Briefly, goat-antihuman IgG, gamma chain-specific (or other suitable gamma chain-specific antibody; GHFC) is covalently coupled to biosensor chips using a standard amine coupling procedure and reagents according to the manufacturer's instructions. Anti-huIL-4R or a control antibody is injected over the immobilized GHFC, and varying amounts of IL-4R are independently passed over a GHFC coated chip (negative control) as well as an anti-huIL-4R-coated chip. Regeneration of the chip is accomplished with one 10-microliter pulse of 100 mM phosphoric acid at 10 microliters/minute. All binding is performed in HBS (10 mM HEPES, 0.15 M NaCl, 3.4 mM EDTA, 0.02% NaN3, 0.005% surfactant P20, pH 7.4).

Example 5

IL-4 Receptor Binding Antibodies

This example provides the amino acid sequences, and the nucleotide sequences encoding them, of the variable domains of the heavy and light chains of antibodies and antibody derivatives that bind to huIL-4R.

A fully human IgG4 antibody comprising the light chain variable region of L1 and the heavy chain variable region of H1 was isolated as described in Example 8 of WO 01/92340 (published Dec. 6, 2001), incorporated herein by reference in its entirety.

The variable region of heavy chain H1 was isolated by cDNA cloning from the hybridoma cell line that produced antibody L1H1 via the polymerase chain reaction (PCR) using the following oligonucleotides as primers:

```
                                          (SEQ ID NO: 70)
GTCGACGCCGCCACCATGGA(A/G)TT(G/T)GGGCTGAGCTGG
Sal I
Degenerate; complementary to VH3030
```

```
                                          (SEQ ID NO: 71)
CTTGACCAGGCAGCCCAGGGC
Complementary to huIgG, 3' of Apa I site
```

The amplification product was inserted as a Sal I/Apa I fragment into pGem-T easy (Promega, Madison, Wis.). In order to improve cleavage, the native H1 leader sequence was replaced with the VH3-30 leader sequence (Matsuda et al., 1993, Nature Genetics 3:88-94).

Oligonucleotide-based mutagenesis of the heavy chain variable domain of H1 was used to create the heavy chain variable domain sequences H2-H14, shown in FIG. 3. Each of these heavy chain variable domain sequences was shown to bind, in combination with the light chain variable domain sequence of L1, to IL-4 receptor alpha using an enzyme-linked immunosorbent assay (ELISA).

Naïve human light chain variable genes were generated by PCR from human B cells and used to construct a variable region cDNA gene library. These were screened in combination with the heavy chain variable region H1 for binding to human IL-4 receptor. Light chain variable regions L2-L6 were identified using this method. Their nucleotide and amino acid sequences are shown in FIGS. 2 and 3, respectively, wherein the CDR regions of each chain are indicated in bold and underlined in L1. The framework (FR) regions also are indicated.

To clone the human kappa constant region, RNA was isolated from a murine hybridoma cell line expressing a human kappa light chain using the RNeasy Mini Kit (Qiagen, Valencia, Calif.). The RNA was reverse transcribed using a First-Strand cDNA Synthesis Kit (Amersham Pharmacia Biotech, Piscataway, N.J.). The human kappa light chain nucleic acid was amplified by PCR from the cDNA as a Bsw I/Not I cassette using primers:

```
                                          (SEQ ID NO: 72)
ATCAAACGTACGGTGGCTGCACCATCTGTCTTCATC
     BsiW I
```

```
                                          (SEQ ID NO: 73)
GTTTAAACGCGGCCGCGGATCCTAACACTCTCCCCTGTTGAAGCTCTTT
     Not I
```

The light chain variable regions L1 and L2 were independently joined to the human kappa light chain constant region as follows: a Nhe I/Bsi WI DNA fragment encoding the light-chain variable region of L1 and the Bsi WI/Not I DNA fragment encoding human kappa constant region DNA fragment were simultaneously subcloned into a pDC409 mammalian expression vector (described in Giri et al., 1994, EMBO J. 13:2822-30 and U.S. Pat. No. 6,642,358, incorporated herein by reference in their entireties) using a VkIII leader sequence. The VkIII leader sequence was constructed as a Sal I/Nhe I cassette by PCR amplification of Kozak (Kozak, 1989, J Cell Biol. 108:229-41) and VkIII A27 (Straubinger et al., 1988, J Mol. Biol. 199:23-34) leader sequences using the following oligonucleotides as primers:

```
                                          (SEQ ID NO: 74)
GTCGACGCCGCCACCATGGAAACCCCAGCGCAGCTTCTCTTCCTCCTGCT
Sal I

ACTCTGGCTCCCAGATACCGCTAGCGAAATTGTGTTGACGCAGTCTCCA
```

```
                                          (SEQ ID NO: 75)
TGGAGACTGCGTCAACACAATTTCGCTAGCGGTATCTGGGAGCCAGAGTA

GCAGGAGGAAGAGAAGCTGCGCTGGGGTTTCCATGGTGGCGGCGTCGAC
                                               Sal I
```

The last six nucleotides in the natural VkIII A27 leader were replaced with the nucleotides encoding an Nhe I site. This resulted in amino acid changes from threonine to glycine and alanine to serine, but did not affect the cleavage site.

Each heavy chain variable region H1, H4, and H14 was joined to a human IgG4 constant region as follows: a Sal I/Apa I DNA fragment encoding the heavy-chain variable region of H1 and an Apa I/Not I DNA fragment encoding human IgG4 constant region (SEQ ID NO:77) were simultaneously inserted into Sal I/Not I digested mammalian expression vector pDC409 (described in Giri et al., 1994, EMBO J. 13:2822-30) using a VH5a leader sequence that was modified at its 3' end to encode an Nhe I site:

```
                                                           (SEQ ID NO: 76)
ATGGGGTCAACCGCCATCCTTGGCCTCCTCCTGGCTGTTCTCCAAGGAGTCGCTAGC
                                                         Nhe I
```

As a result of this change, the last two amino acids are alanine and serine, whereas the last two amino acids of the wild type VH5a are cysteine and alanine. Site-directed mutagenesis was used on the H4-IgG4-encoding construct to make constructs comprising the H12 and H13 heavy chain variable regions. The nucleotide and amino acid sequences of H1-H14 are shown in FIGS. 2 and 3, respectively, wherein the CDR regions of each chain are indicated in bold and underlined in H1. The framework (FR) regions also are indicated.

Antibodies and/or antibody derivatives comprising the variable domain combinations L1H1, L1H2, L1H3, L1H4, L1H5, L1H6, L1H7, L1H8, L1H9, L1H10, L1H11, L2H1, L2H2, L2H3, L2H4, L2H5, L2H6, L2H7, L2H8, L2H9, L2H10, L2H11, L2H12, L2H13, L2H14, L3H1, L4H1, L5H1, and L6H1 were tested using a biochemical binding assay and/or the method of Example 2 and found to bind to IL-4 receptor.

Example 6

Species and Sequence Specificity of Antibodies

This example provides a method for determining the species and sequence specificity of an antibody that binds to the IL-4 receptor.

A fluorescence-activated cell sorter (FACS) binding assay can be used to evaluate the species and/or sequence specificity of an anti-IL-4 receptor antibody. The extracellular domain of IL-4 receptor comprises a cytokine receptor domain (domain I) and a fibronectin type III domain (domain II) (Hage et al., 1999, Cell 97:271-81). Constructs comprising human IL-4 receptor domains I and/or II, murine IL-4 receptor domains I and/or II, combinations of human and murine IL-4 receptor domains I and II, or fragments of human or murine IL-4 receptor domains I and/or II are expressed as C-terminal, in-frame fusions with chicken avidin. (Murine IL-4 receptor sequences are provided in, for example, Schulte et al., 1997, J. Exp. Med. 186:1419-29, Wrighton et al., 1992, Growth Factors 6:103-18, Harada et al., 1990, Proc. Natl. Acad. Sci. U.S.A. 87:857-61, Mosley et al., 1989, Cell 59:335-48.) The fusion protein expression vectors are individually transiently transfected into 293T cells. The conditioned media are used as the source of fusion protein without purification. The avidin tag of the IL-4 receptor construct is captured from solution by a biotin-coated bead. A FITC labeled anti-avidin antibody is used to detect the avidin portion of the fusion construct. An anti-IL-4 receptor antibody is incubated with the biotin-captured IL-4 receptor construct. FITC labeled mouse F(ab')$_2$ anti-human IgG is used as a secondary antibody for detection. The bead-antibody mixture is subjected to FACS analysis on a Becton Dickinson Bioscience FACScan (BD, Franklin Lakes, N.J.).

Using the above method, it was found that several anti-IL-4 receptor antibodies described herein bound well to a construct comprising domains I and II of human IL-4 receptor but did not bind to a construct comprising domains I and II of murine IL-4 receptor. The antibodies bound weakly to a construct comprising domain I of human IL-4 receptor (but not comprising domain II) and not at all to a construct comprising human IL-4 receptor domain II (but not comprising domain I). It was further found that the antibodies bound well to a construct comprising domain I of human IL-4 receptor and domain II of murine IL-4 receptor.

The foregoing examples, both working and prophetic, are non-limiting and are provided to illustrate particular embodiments of the instant invention. All references cited herein are incorporated by reference in their entireties.

---

What is claimed is:

1. An isolated nucleic acid, or its complement, comprising a nucleotide sequence that encodes either
   a) the light chain variable domain of SEQ ID NO:6
   or
   b) the heavy chain variable domain of SEQ ID NO:42
   or
   c) said light chain variable domain of a) and said heavy chain variable domain of b).

2. The isolated nucleic acid of claim 1, or its complement, wherein said nucleotide sequence encodes either
   a) the light chain of an antibody, said light chain comprising the light chain variable domain of SEQ ID NO:6
   or
   b) the heavy chain of an antibody, said heavy chain comprising the heavy chain variable domain of SEQ ID NO:42
   or
   c) said light chain of a) and said heavy chain of b).

3. The isolated nucleic acid of claim 1, or its complement, wherein said nucleotide sequence encodes a combination of light chain variable domain and heavy chain variable domain selected from the group of combinations consisting of L2H1 (SEQ ID NO:6 and 16), L2H2 (SEQ ID NO:6 and 18), L2H3 (SEQ ID NO:6 and 20), L2H4 (SEQ ID NO:6 and 22), L2H5 (SEQ ID NO:6 and 24), L2H6 (SEQ ID NO:6 and 26), L2H7 (SEQ ID NO:6 and 28), L2H8 (SEQ ID NO:6 and 30), L2H9 (SEQ ID NO:6 and 32), L2H10 (SEQ ID NO:6 and 34), L2H11 (SEQ ID NO:6 and 36), L2H12 (SEQ ID NO:6 and 38), L2H13 (SEQ ID NO:6 and 40), and L2H14 (SEQ ID NO:6 and 42).

4. The isolated nucleic acid of claim 2, or its complement, wherein said antibody is a human, or chimeric antibody.

5. The isolated nucleic acid of claim 2, or its complement, wherein said antibody is a monoclonal antibody.

6. The isolated nucleic acid of claim 2, or its complement, wherein said antibody is selected from the group consisting of an IgD, IgE, IgM, IgG1, IgG2, IgG3, IgG4, and IgG4 having at least one mutation in a hinge region that alleviates a tendency to form intra-H chain disulfide bond antibody.

7. The isolated nucleic acid of claim 1, or its complement, wherein said nucleotide sequence comprises at least one sequence selected from the group consisting of SEQ ID NO:5, 7, 9, 11, 13, 17, 19, 21, 23, 25, 27, 29, 31, 33, 35, 37, 39, 41, 43, 45, 47, 49, 51, 53, 55, 57, 59, and 61.

8. A vector comprising said isolated nucleic acid of claim 1, or comprising the complement of said isolated nucleic acid of claim 1.

9. The vector of claim 8 wherein said vector is an expression vector.

10. An isolated cell comprising said nucleic acid of claim 1, or comprising the complement of said isolated nucleic acid of claim 1.

11. The isolated cell of claim 10 wherein said cell is either a hybridoma or a transgenic cell.

12. A method of making an antibody comprising the light chain variable domain of SEQ ID NO:6 and the heavy chain variable domain of SEQ ID NO:42, said method comprising incubating a cell comprising a nucleic acid encoding said light chain and a nucleic acid encoding said heavy chain under conditions that allow said cell to express said light chain and said heavy chain and that allow said light chain and said heavy chain to assemble into said antibody, and isolating said antibody from said cell.

* * * * *

SEQUENCE LISTING

```
<160> NUMBER OF SEQ ID NOS: 77

<210> SEQ ID NO 1
<211> LENGTH: 2475
<212> TYPE: DNA
<213> ORGANISM: Homo sapien
<220> FEATURE:
<221> NAME/KEY: CDS
<222> LOCATION: (1)..(2475)

<400> SEQUENCE: 1 atg ggg tgg ctt tgc tct ggg ctc ctg ttc cct gtg agc tgc ctg gtc        48
Met Gly Trp Leu Cys Ser Gly Leu Leu Phe Pro Val Ser Cys Leu Val
1               5                   10                  15 ctg ctg cag gtg gca agc tct ggg aac atg aag gtc ttg cag gag ccc        96
Leu Leu Gln Val Ala Ser Ser Gly Asn Met Lys Val Leu Gln Glu Pro
                20                  25                  30 acc tgc gtc tcc gac tac atg agc atc tct act tgc gag tgg aag atg       144
Thr Cys Val Ser Asp Tyr Met Ser Ile Ser Thr Cys Glu Trp Lys Met
            35                  40                  45 aat ggt ccc acc aat tgc agc acc gag ctc cgc ctg ttg tac cag ctg       192
```

```
                                                            -continued

Asn Gly Pro Thr Asn Cys Ser Thr Glu Leu Arg Leu Leu Tyr Gln Leu
 50                  55                  60 gtt ttt ctg ctc tcc gaa gcc cac acg tgt atc cct gag aac aac gga       240
Val Phe Leu Leu Ser Glu Ala His Thr Cys Ile Pro Glu Asn Asn Gly
 65                  70                  75                  80 ggc gcg ggg tgc gtg tgc cac ctg ctc atg gat gac gtg gtc agt gcg       288
Gly Ala Gly Cys Val Cys His Leu Leu Met Asp Asp Val Val Ser Ala
                     85                  90                  95 gat aac tat aca ctg gac ctg tgg gct ggg cag cag ctg ctg tgg aag       336
Asp Asn Tyr Thr Leu Asp Leu Trp Ala Gly Gln Gln Leu Leu Trp Lys
            100                 105                 110 ggc tcc ttc aag ccc agc gag cat gtg aaa ccc agg gcc cca gga aac       384
Gly Ser Phe Lys Pro Ser Glu His Val Lys Pro Arg Ala Pro Gly Asn
        115                 120                 125 ctg aca gtt cac acc aat gtc tcc gac act ctg ctg acc tgg agc           432
Leu Thr Val His Thr Asn Val Ser Asp Thr Leu Leu Leu Thr Trp Ser
    130                 135                 140 aac ccg tat ccc cct gac aat tac ctg tat aat cat ctc acc tat gca       480
Asn Pro Tyr Pro Pro Asp Asn Tyr Leu Tyr Asn His Leu Thr Tyr Ala
145                 150                 155                 160 gtc aac att tgg agt gaa aac gac ccg gca gat ttc aga atc tat aac       528
Val Asn Ile Trp Ser Glu Asn Asp Pro Ala Asp Phe Arg Ile Tyr Asn
                    165                 170                 175 gtg acc tac cta gaa ccc tcc ctc cgc atc gca gcc agc acc ctg aag       576
Val Thr Tyr Leu Glu Pro Ser Leu Arg Ile Ala Ala Ser Thr Leu Lys
            180                 185                 190 tct ggg att tcc tac agg gca cgg gtg agg gcc tgg gct cag tgc tat       624
Ser Gly Ile Ser Tyr Arg Ala Arg Val Arg Ala Trp Ala Gln Cys Tyr
        195                 200                 205 aac acc acc tgg agt gag tgg agc ccc agc acc aag tgg cac aac tcc       672
Asn Thr Thr Trp Ser Glu Trp Ser Pro Ser Thr Lys Trp His Asn Ser
    210                 215                 220 tac agg gag ccc ttc gag cag cac ctc ctg ctg ggc gtc agc gtt tcc       720
Tyr Arg Glu Pro Phe Glu Gln His Leu Leu Leu Gly Val Ser Val Ser
225                 230                 235                 240 tgc att gtc atc ctg gcc gtc tgc ctg ttg tgc tat gtc agc atc acc       768
Cys Ile Val Ile Leu Ala Val Cys Leu Leu Cys Tyr Val Ser Ile Thr
                    245                 250                 255 aag att aag aaa gaa tgg tgg gat cag att ccc aac cca gcc cgc agc       816
Lys Ile Lys Lys Glu Trp Trp Asp Gln Ile Pro Asn Pro Ala Arg Ser
            260                 265                 270 cgc ctc gtg gct ata ata atc cag gat gct cag ggg tca cag tgg gag       864
Arg Leu Val Ala Ile Ile Ile Gln Asp Ala Gln Gly Ser Gln Trp Glu
        275                 280                 285 aag cgg tcc cga ggc cag gaa cca gcc aag tgc cca cac tgg aag aat       912
Lys Arg Ser Arg Gly Gln Glu Pro Ala Lys Cys Pro His Trp Lys Asn
    290                 295                 300 tgt ctt acc aag ctc ttg ccc tgt ttt ctg gag cac aac atg aaa agg       960
Cys Leu Thr Lys Leu Leu Pro Cys Phe Leu Glu His Asn Met Lys Arg
305                 310                 315                 320 gat gaa gat cct cac aag gct gcc aaa gag atg cct ttc cag ggc tct      1008
Asp Glu Asp Pro His Lys Ala Ala Lys Glu Met Pro Phe Gln Gly Ser
                    325                 330                 335 gga aaa tca gca tgg tgc cca gtg gag atc agc aag aca gtc ctc tgg      1056
Gly Lys Ser Ala Trp Cys Pro Val Glu Ile Ser Lys Thr Val Leu Trp
            340                 345                 350 cca gag agc atc agc gtg gtg cga tgt gtg gag ttg ttt gag gcc ccg      1104
Pro Glu Ser Ile Ser Val Val Arg Cys Val Glu Leu Phe Glu Ala Pro
        355                 360                 365
```

```
gtg gag tgt gag gag gag gag gag gta gag gaa gaa aaa ggg agc ttc       1152
Val Glu Cys Glu Glu Glu Glu Val Glu Glu Glu Lys Gly Ser Phe
    370                 375                 380 tgt gca tcg cct gag agc agc agg gat gac ttc cag gag gga agg gag       1200
Cys Ala Ser Pro Glu Ser Ser Arg Asp Asp Phe Gln Glu Gly Arg Glu
385                 390                 395                 400 ggc att gtg gcc cgg cta aca gag agc ctg ttc ctg gac ctg ctc gga       1248
Gly Ile Val Ala Arg Leu Thr Glu Ser Leu Phe Leu Asp Leu Leu Gly
                405                 410                 415 gag gag aat ggg ggc ttt tgc cag cag gac atg ggg gag tca tgc ctt       1296
Glu Glu Asn Gly Gly Phe Cys Gln Gln Asp Met Gly Glu Ser Cys Leu
            420                 425                 430 ctt cca cct tcg gga agt acg agt gct cac atg ccc tgg gat gag ttc       1344
Leu Pro Pro Ser Gly Ser Thr Ser Ala His Met Pro Trp Asp Glu Phe
        435                 440                 445 cca agt gca ggg ccc aag gag gca cct ccc tgg ggc aag gag cag cct       1392
Pro Ser Ala Gly Pro Lys Glu Ala Pro Pro Trp Gly Lys Glu Gln Pro
    450                 455                 460 ctc cac ctg gag cca agt cct cct gcc agc ccg acc cag agt cca gac       1440
Leu His Leu Glu Pro Ser Pro Pro Ala Ser Pro Thr Gln Ser Pro Asp
465                 470                 475                 480 aac ctg act tgc aca gag acg ccc ctc gtc atc gca ggc aac cct gct       1488
Asn Leu Thr Cys Thr Glu Thr Pro Leu Val Ile Ala Gly Asn Pro Ala
                485                 490                 495 tac cgc agc ttc agc aac tcc ctg agc cag tca ccg tgt ccc aga gag       1536
Tyr Arg Ser Phe Ser Asn Ser Leu Ser Gln Ser Pro Cys Pro Arg Glu
            500                 505                 510 ctg ggt cca gac cca ctg ctg gcc aga cac ctg gag gaa gta gaa ccc       1584
Leu Gly Pro Asp Pro Leu Leu Ala Arg His Leu Glu Glu Val Glu Pro
        515                 520                 525 gag atg ccc tgt gtc ccc cag ctc tct gag cca acc act gtg ccc caa       1632
Glu Met Pro Cys Val Pro Gln Leu Ser Glu Pro Thr Thr Val Pro Gln
    530                 535                 540 cct gag cca gaa acc tgg gag cag atc ctc cgc cga aat gtc ctc cag       1680
Pro Glu Pro Glu Thr Trp Glu Gln Ile Leu Arg Arg Asn Val Leu Gln
545                 550                 555                 560 cat ggg gca gct gca gcc ccc gtc tcg gcc ccc acc agt ggc tat cag       1728
His Gly Ala Ala Ala Ala Pro Val Ser Ala Pro Thr Ser Gly Tyr Gln
                565                 570                 575 gag ttt gta cat gcg gtg gag cag ggt ggc acc cag gcc agt gcg gtg       1776
Glu Phe Val His Ala Val Glu Gln Gly Gly Thr Gln Ala Ser Ala Val
            580                 585                 590 gtg ggc ttg ggt ccc cca gga gag gct ggt tac aag gcc ttc tca agc       1824
Val Gly Leu Gly Pro Pro Gly Glu Ala Gly Tyr Lys Ala Phe Ser Ser
        595                 600                 605 ctg ctt gcc agc agt gct gtg tcc cca gag aaa tgt ggg ttt ggg gct       1872
Leu Leu Ala Ser Ser Ala Val Ser Pro Glu Lys Cys Gly Phe Gly Ala
    610                 615                 620 agc agt ggg gaa gag ggg tat aag cct ttc caa gac ctc att cct ggc       1920
Ser Ser Gly Glu Glu Gly Tyr Lys Pro Phe Gln Asp Leu Ile Pro Gly
625                 630                 635                 640 tgc cct ggg gac cct gcc cca gtc cct gtc ccc ttg ttc acc ttt gga       1968
Cys Pro Gly Asp Pro Ala Pro Val Pro Val Pro Leu Phe Thr Phe Gly
                645                 650                 655 ctg gac agg gag cca cct cgc agt ccg cag agc tca cat ctc cca agc       2016
Leu Asp Arg Glu Pro Pro Arg Ser Pro Gln Ser Ser His Leu Pro Ser
            660                 665                 670 agc tcc cca gag cac ctg ggt ctg gag ccg ggg gaa aag gta gag gac       2064
Ser Ser Pro Glu His Leu Gly Leu Glu Pro Gly Glu Lys Val Glu Asp
        675                 680                 685
```

```
atg cca aag ccc cca ctt ccc cag gag cag gcc aca gac ccc ctt gtg    2112
Met Pro Lys Pro Pro Leu Pro Gln Glu Gln Ala Thr Asp Pro Leu Val
690                 695                 700 gac agc ctg ggc agt ggc att gtc tac tca gcc ctt acc tgc cac ctg    2160
Asp Ser Leu Gly Ser Gly Ile Val Tyr Ser Ala Leu Thr Cys His Leu
705                 710                 715                 720 tgc ggc cac ctg aaa cag tgt cat ggc cag gag gat ggt ggc cag acc    2208
Cys Gly His Leu Lys Gln Cys His Gly Gln Glu Asp Gly Gly Gln Thr
                725                 730                 735 cct gtc atg gcc agt cct tgc tgt ggc tgc tgc tgt gga gac agg tcc    2256
Pro Val Met Ala Ser Pro Cys Cys Gly Cys Cys Cys Gly Asp Arg Ser
    740                 745                 750 tcg ccc cct aca acc ccc ctg agg gcc cca gac ccc tct cca ggt ggg    2304
Ser Pro Pro Thr Thr Pro Leu Arg Ala Pro Asp Pro Ser Pro Gly Gly
755                 760                 765 gtt cca ctg gag gcc agt ctg tgt ccg gcc tcc ctg gca ccc tcg ggc    2352
Val Pro Leu Glu Ala Ser Leu Cys Pro Ala Ser Leu Ala Pro Ser Gly
        770                 775                 780 atc tca gag aag agt aaa tcc tca tca tcc ttc cat cct gcc cct ggc    2400
Ile Ser Glu Lys Ser Lys Ser Ser Ser Ser Phe His Pro Ala Pro Gly
785                 790                 795                 800 aat gct cag agc tca agc cag acc ccc aaa atc gtg aac ttt gtc tcc    2448
Asn Ala Gln Ser Ser Ser Gln Thr Pro Lys Ile Val Asn Phe Val Ser
            805                 810                 815 gtg gga ccc aca tac atg agg gtc tct                                2475
Val Gly Pro Thr Tyr Met Arg Val Ser
        820                 825

<210> SEQ ID NO 2
<211> LENGTH: 825
<212> TYPE: PRT
<213> ORGANISM: Homo sapien

<400> SEQUENCE: 2

Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
    130                 135                 140

Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
```

-continued

```
            180                 185                 190
Ser Gly Ile Ser Tyr Arg Ala Arg Val Arg Ala Trp Ala Gln Cys Tyr
            195                 200                 205
Asn Thr Thr Trp Ser Glu Trp Ser Pro Ser Thr Lys Trp His Asn Ser
210                 215                 220
Tyr Arg Glu Pro Phe Glu Gln His Leu Leu Gly Val Ser Val Ser
225                 230                 235                 240
Cys Ile Val Ile Leu Ala Val Cys Leu Leu Cys Tyr Val Ser Ile Thr
                245                 250                 255
Lys Ile Lys Lys Glu Trp Trp Asp Gln Ile Pro Asn Pro Ala Arg Ser
            260                 265                 270
Arg Leu Val Ala Ile Ile Gln Asp Ala Gln Gly Ser Gln Trp Glu
            275                 280                 285
Lys Arg Ser Arg Gly Gln Glu Pro Ala Lys Cys Pro His Trp Lys Asn
            290                 295                 300
Cys Leu Thr Lys Leu Leu Pro Cys Phe Leu Glu His Asn Met Lys Arg
305                 310                 315                 320
Asp Glu Asp Pro His Lys Ala Ala Lys Glu Met Pro Phe Gln Gly Ser
                325                 330                 335
Gly Lys Ser Ala Trp Cys Pro Val Glu Ile Ser Lys Thr Val Leu Trp
            340                 345                 350
Pro Glu Ser Ile Ser Val Val Arg Cys Val Glu Leu Phe Glu Ala Pro
            355                 360                 365
Val Glu Cys Glu Glu Glu Glu Val Glu Glu Lys Gly Ser Phe
            370                 375                 380
Cys Ala Ser Pro Glu Ser Ser Arg Asp Asp Phe Gln Glu Gly Arg Glu
385                 390                 395                 400
Gly Ile Val Ala Arg Leu Thr Glu Ser Leu Phe Leu Asp Leu Leu Gly
                405                 410                 415
Glu Glu Asn Gly Gly Phe Cys Gln Gln Asp Met Gly Glu Ser Cys Leu
                420                 425                 430
Leu Pro Pro Ser Gly Ser Thr Ser Ala His Met Pro Trp Asp Glu Phe
            435                 440                 445
Pro Ser Ala Gly Pro Lys Glu Ala Pro Pro Trp Gly Lys Glu Gln Pro
450                 455                 460
Leu His Leu Glu Pro Ser Pro Ala Ser Pro Thr Gln Ser Pro Asp
465                 470                 475                 480
Asn Leu Thr Cys Thr Glu Thr Pro Leu Val Ile Ala Gly Asn Pro Ala
                485                 490                 495
Tyr Arg Ser Phe Ser Asn Ser Leu Ser Gln Ser Pro Cys Pro Arg Glu
                500                 505                 510
Leu Gly Pro Asp Pro Leu Leu Ala Arg His Leu Glu Glu Val Glu Pro
            515                 520                 525
Glu Met Pro Cys Val Pro Gln Leu Ser Glu Pro Thr Thr Val Pro Gln
            530                 535                 540
Pro Glu Pro Glu Thr Trp Glu Gln Ile Leu Arg Arg Asn Val Leu Gln
545                 550                 555                 560
His Gly Ala Ala Ala Pro Val Ser Ala Pro Thr Ser Gly Tyr Gln
                565                 570                 575
Glu Phe Val His Ala Val Glu Gln Gly Gly Thr Gln Ala Ser Ala Val
            580                 585                 590
Val Gly Leu Gly Pro Pro Gly Glu Ala Gly Tyr Lys Ala Phe Ser Ser
            595                 600                 605
```

```
Leu Leu Ala Ser Ser Ala Val Ser Pro Glu Lys Cys Gly Phe Gly Ala
    610                 615                 620

Ser Ser Gly Glu Glu Gly Tyr Lys Pro Phe Gln Asp Leu Ile Pro Gly
625                 630                 635                 640

Cys Pro Gly Asp Pro Ala Pro Val Pro Val Pro Leu Phe Thr Phe Gly
                645                 650                 655

Leu Asp Arg Glu Pro Pro Arg Ser Pro Gln Ser Ser His Leu Pro Ser
            660                 665                 670

Ser Ser Pro Glu His Leu Gly Leu Glu Pro Gly Glu Lys Val Glu Asp
        675                 680                 685

Met Pro Lys Pro Pro Leu Pro Gln Glu Gln Ala Thr Asp Pro Leu Val
    690                 695                 700

Asp Ser Leu Gly Ser Gly Ile Val Tyr Ser Ala Leu Thr Cys His Leu
705                 710                 715                 720

Cys Gly His Leu Lys Gln Cys His Gly Gln Glu Asp Gly Gly Gln Thr
                725                 730                 735

Pro Val Met Ala Ser Pro Cys Cys Gly Cys Cys Cys Gly Asp Arg Ser
            740                 745                 750

Ser Pro Pro Thr Thr Pro Leu Arg Ala Pro Asp Pro Ser Pro Gly Gly
        755                 760                 765

Val Pro Leu Glu Ala Ser Leu Cys Pro Ala Ser Leu Ala Pro Ser Gly
    770                 775                 780

Ile Ser Glu Lys Ser Lys Ser Ser Ser Phe His Pro Ala Pro Gly
785                 790                 795                 800

Asn Ala Gln Ser Ser Ser Gln Thr Pro Lys Ile Val Asn Phe Val Ser
                805                 810                 815

Val Gly Pro Thr Tyr Met Arg Val Ser
            820                 825

<210> SEQ ID NO 3
<211> LENGTH: 327
<212> TYPE: DNA
<213> ORGANISM: Artificial
<220> FEATURE:
<223> OTHER INFORMATION: Light chain variable sequence
<220> FEATURE:
<221> NAME/KEY: CDS
<222> LOCATION: (1)..(327)

<400> SEQUENCE: 3 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
            20                  25                  30 tac tta gcc tgg tac cag cag aaa cct ggc cag gct ccc agg ctc ctc     144
Tyr Leu Ala Trp Tyr Gln Gln Lys Pro Gly Gln Ala Pro Arg Leu Leu
        35                  40                  45 atc ttt ggt gca tcc agc agg gcc act ggc atc cca gac agg ttc agt     192
Ile Phe Gly Ala Ser Ser Arg Ala Thr Gly Ile Pro Asp Arg Phe Ser
    50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
65                  70                  75                  80 cct gaa gat ttt gca gtg tat tac tgt cag cag tat ggt agc tca cct     288
Pro Glu Asp Phe Ala Val Tyr Tyr Cys Gln Gln Tyr Gly Ser Ser Pro
                85                  90                  95
```

```
ccg tgg acg ttc ggc caa ggg acc aag gtg gaa atc aaa          327
Pro Trp Thr Phe Gly Gln Gly Thr Lys Val Glu Ile Lys
        100                 105

<210> SEQ ID NO 4
<211> LENGTH: 109
<212> TYPE: PRT
<213> ORGANISM: Artificial
<220> FEATURE:
<223> OTHER INFORMATION: Synthetic Construct

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Phe Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Trp Thr Phe Gly Gln Gly Thr Lys Val Glu Ile Lys
            100                 105

<210> SEQ ID NO 5
<211> LENGTH: 327
<212> TYPE: DNA
<213> ORGANISM: Artificial
<220> FEATURE:
<223> OTHER INFORMATION: Light chain variable sequence
<220> FEATURE:
<221> NAME/KEY: CDS
<222> LOCATION: (1)..(327)

<400> SEQUENCE: 5 gaa att gtg ttg acg cag tct cca ggc acc ctg tct ttg tct cca ggg     48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc aac agc     96
Glu Arg Ala Thr Leu Ser Cys Arg Ala Ser Gln Ser Val Ser Asn Ser
            20                  25                  30 tac tta gcc tgg tac cag cag aaa cct ggc cag gct ccc agg ctc ctc    144
Tyr Leu Ala Trp Tyr Gln Gln Lys Pro Gly Gln Ala Pro Arg Leu Leu
        35                  40                  45 atc tat ggt gca tcc agc agg gcc cct ggc atc cca gac agg ttc agt    192
Ile Tyr Gly Ala Ser Ser Arg Ala Pro Gly Ile Pro Asp Arg Phe Ser
    50                  55                  60 ggc agt ggg tct ggg aca gac ttc act ctc acc atc agc aga ctg gag    240
Gly Ser Gly Ser Gly Thr Asp Phe Thr Leu Thr Ile Ser Arg Leu Glu
65                  70                  75                  80 cct gaa gat ttt gca gtg tat tac tgt cag cag tat gat cac tca gca    288
Pro Glu Asp Phe Ala Val Tyr Tyr Cys Gln Gln Tyr Asp His Ser Ala
                85                  90                  95 ggg tgg acg ttc ggc caa ggg acc aag gtg gag atc aaa                327
Gly Trp Thr Phe Gly Gln Gly Thr Lys Val Glu Ile Lys
            100                 105

<210> SEQ ID NO 6
```

```
<211> LENGTH: 109
<212> TYPE: PRT
<213> ORGANISM: Artificial
<220> FEATURE:
<223> OTHER INFORMATION: Synthetic Construct

<400> SEQUENCE: 6

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp His Ser Ala
                85                  90                  95

Gly Trp Thr Phe Gly Gln Gly Thr Lys Val Glu Ile Lys
            100                 105

<210> SEQ ID NO 7
<211> LENGTH: 327
<212> TYPE: DNA
<213> ORGANISM: Artificial
<220> FEATURE:
<223> OTHER INFORMATION: Light chain variable sequence
<220> FEATURE:
<221> NAME/KEY: CDS
<222> LOCATION: (1)..(327)

<400> SEQUENCE: 7 gaa att gtg ttg acg cag tct cca ggc acc ctg tct ttg tct ccg ggg      48
Glu Ile Val Leu Thr Gln Ser Pro Gly Thr Leu Ser Leu Ser Pro Gly
1               5                   10                  15 gaa aga gcc acc ctc tcc tgc agg gcc agt cag act gtt aac agc gac      96
Glu Arg Ala Thr Leu Ser Cys Arg Ala Ser Gln Thr Val Asn Ser Asp
            20                  25                  30 tac tta gcc tgg tac cag cag aaa ccg ggc cag gct ccc agg ctc ctc     144
Tyr Leu Ala Trp Tyr Gln Gln Lys Pro Gly Gln Ala Pro Arg Leu Leu
        35                  40                  45 atc tat ggt gca tcc agc agg gcc act ggc atc cca gac agg ttc agt     192
Ile Tyr Gly Ala Ser Ser Arg Ala Thr Gly Ile Pro Asp Arg Phe Ser
    50                  55                  60 ggc agt ggg tct ggg aca gac ttc act ctc acc atc agc aga ctg gag     240
Gly Ser Gly Ser Gly Thr Asp Phe Thr Leu Thr Ile Ser Arg Leu Glu
65                  70                  75                  80 cct gaa gat ttt gca gtc tat tac tgt cag cag tat ggt agg tca cct     288
Pro Glu Asp Phe Ala Val Tyr Tyr Cys Gln Gln Tyr Gly Arg Ser Pro
                85                  90                  95 ccg tgg acg ttc ggc caa ggg acc aaa gtg gat atc aaa                 327
Pro Trp Thr Phe Gly Gln Gly Thr Lys Val Asp Ile Lys
            100                 105

<210> SEQ ID NO 8
<211> LENGTH: 109
<212> TYPE: PRT
<213> ORGANISM: Artificial
<220> FEATURE:
<223> OTHER INFORMATION: Synthetic Construct

<400> SEQUENCE: 8
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Asn Ser Asp
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Pro
                85                  90                  95

Pro Trp Thr Phe Gly Gln Gly Thr Lys Val Asp Ile Lys
                100                 105
```

```
<210> SEQ ID NO 9
<211> LENGTH: 327
<212> TYPE: DNA
<213> ORGANISM: Artificial
<220> FEATURE:
<223> OTHER INFORMATION: Light chain variable sequence
<220> FEATURE:
<221> NAME/KEY: CDS
<222> LOCATION: (1)..(327)

<400> SEQUENCE: 9
```

```
gaa att gtg atg acg cag tct cca ggc acc ctg tct ttg tct cca ggg     48
Glu Ile Val Met Thr Gln Ser Pro Gly Thr Leu Ser Leu Ser Pro Gly
1               5                   10                  15 gaa aga gcc acc ctc tcc tgc agg gcc agt cag agt gtt agc agc gac     96
Glu Arg Ala Thr Leu Ser Cys Arg Ala Ser Gln Ser Val Ser Ser Asp
                20                  25                  30 tac tta gcc tgg tac cag cag aaa cct ggc cag gct ccc agg ctc ctc    144
Tyr Leu Ala Trp Tyr Gln Gln Lys Pro Gly Gln Ala Pro Arg Leu Leu
            35                  40                  45 atc tat ggt gca tct agc agg gcc tct ggc atc cca gac agg ttc agt    192
Ile Tyr Gly Ala Ser Ser Arg Ala Ser Gly Ile Pro Asp Arg Phe Ser
    50                  55                  60 ggc agt ggg ttt ggg aca gac ttc act ctc acc atc agc aga ctg gag    240
Gly Ser Gly Phe Gly Thr Asp Phe Thr Leu Thr Ile Ser Arg Leu Glu
65                  70                  75                  80 cct gaa gat ttt gca ata tat tac tgt cag cag tat ggt agc tca cct    288
Pro Glu Asp Phe Ala Ile Tyr Tyr Cys Gln Gln Tyr Gly Ser Ser Pro
                85                  90                  95 ccg tgg acg ttc ggc caa ggg acc aag gtg gaa atc aaa                327
Pro Trp Thr Phe Gly Gln Gly Thr Lys Val Glu Ile Lys
                100                 105
```

```
<210> SEQ ID NO 10
<211> LENGTH: 109
<212> TYPE: PRT
<213> ORGANISM: Artificial
<220> FEATURE:
<223> OTHER INFORMATION: Synthetic Construct

<400> SEQUENCE: 10
```

```
Glu Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asp
                20                  25                  30
```

```
Tyr Leu Ala Trp Tyr Gln Gln Lys Pro Gly Gln Ala Pro Arg Leu Leu
        35                  40                  45

Ile Tyr Gly Ala Ser Ser Arg Ala Ser Gly Ile Pro Asp Arg Phe Ser
 50                  55                  60

Gly Ser Gly Phe Gly Thr Asp Phe Thr Leu Thr Ile Ser Arg Leu Glu
 65                  70                  75                  80

Pro Glu Asp Phe Ala Ile Tyr Tyr Cys Gln Gln Tyr Gly Ser Ser Pro
                 85                  90                  95

Pro Trp Thr Phe Gly Gln Gly Thr Lys Val Glu Ile Lys
            100                 105
```

<210> SEQ ID NO 11
<211> LENGTH: 327
<212> TYPE: DNA
<213> ORGANISM: Artificial
<220> FEATURE:
<223> OTHER INFORMATION: Light chain variable sequence
<220> FEATURE:
<221> NAME/KEY: CDS
<222> LOCATION: (1)..(327)

<400> SEQUENCE: 11

```
gat att gtg ctg acc cag tct cca gcc acc ctg tct ttg tct cca ggg      48
Asp Ile Val Leu Thr Gln Ser Pro Ala Thr Leu Ser Leu Ser Pro Gly
 1               5                  10                  15 gaa aga gcc acc ctc tcc tgc agg gcc agt cag agt gtt aac agc aac      96
Glu Arg Ala Thr Leu Ser Cys Arg Ala Ser Gln Ser Val Asn Ser Asn
             20                  25                  30 tac tta gcc tgg tac cag cag aaa cct ggc cag gct ccc agg ctc ctc     144
Tyr Leu Ala Trp Tyr Gln Gln Lys Pro Gly Gln Ala Pro Arg Leu Leu
         35                  40                  45 atc tat ggt aca tcc tac agg gcc act ggc atc cca gac agg ttc agt     192
Ile Tyr Gly Thr Ser Tyr Arg Ala Thr Gly Ile Pro Asp Arg Phe Ser
 50                  55                  60 ggc agt ggg tct ggg aca gac ttc act ctc acc atc acc aga ctg gag     240
Gly Ser Gly Ser Gly Thr Asp Phe Thr Leu Thr Ile Thr Arg Leu Glu
 65                  70                  75                  80 cct gaa gat ttt gca gtg tat tac tgt cag cag tat ggt agc tca cca     288
Pro Glu Asp Phe Ala Val Tyr Tyr Cys Gln Gln Tyr Gly Ser Ser Pro
                 85                  90                  95 ccg tgg acg ttc ggc caa ggg aca cga ctg gag att aaa                 327
Pro Trp Thr Phe Gly Gln Gly Thr Arg Leu Glu Ile Lys
            100                 105
```

<210> SEQ ID NO 12
<211> LENGTH: 109
<212> TYPE: PRT
<213> ORGANISM: Artificial
<220> FEATURE:
<223> OTHER INFORMATION: Synthetic Construct

<400> SEQUENCE: 12

```
Asp Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Asn Ser Asn
             20                  25                  30

Tyr Leu Ala Trp Tyr Gln Gln Lys Pro Gly Gln Ala Pro Arg Leu Leu
         35                  40                  45

Ile Tyr Gly Thr Ser Tyr Arg Ala Thr Gly Ile Pro Asp Arg Phe Ser
 50                  55                  60

Gly Ser Gly Ser Gly Thr Asp Phe Thr Leu Thr Ile Thr Arg Leu Glu
```

```
                 65                  70                  75                  80
Pro Glu Asp Phe Ala Val Tyr Tyr Cys Gln Gln Tyr Gly Ser Ser Pro
                     85                  90                  95

Pro Trp Thr Phe Gly Gln Gly Thr Arg Leu Glu Ile Lys
                100                 105

<210> SEQ ID NO 13
<211> LENGTH: 327
<212> TYPE: DNA
<213> ORGANISM: Artificial
<220> FEATURE:
<223> OTHER INFORMATION: Light chain variable sequence
<220> FEATURE:
<221> NAME/KEY: CDS
<222> LOCATION: (1)..(327)

<400> SEQUENCE: 13 gat att gtg ctg acg cag act cca gcc acc ctg tct ttg tct cca ggg        48
Asp Ile Val Leu Thr Gln Thr Pro Ala Thr Leu Ser Leu Ser Pro Gly
1               5                   10                  15 gaa aga gcc acc ctc tcc tgc agg gcc agt cag agt gtt ggc agc agc        96
Glu Arg Ala Thr Leu Ser Cys Arg Ala Ser Gln Ser Val Gly Ser Ser
            20                  25                  30 tac tta gcc tgg tac cag cag aga cct ggc cag gct ccc agg ctc ctc       144
Tyr Leu Ala Trp Tyr Gln Gln Arg Pro Gly Gln Ala Pro Arg Leu Leu
        35                  40                  45 atc tat ggt gca tcc agc agg gcc act ggc atc ccg gac agg ttc agt       192
Ile Tyr Gly Ala Ser Ser Arg Ala Thr Gly Ile Pro Asp Arg Phe Ser
    50                  55                  60 ggc agt ggg tct ggg aca gac ttc act ctc acg atc agc aga ctg gag       240
Gly Ser Gly Ser Gly Thr Asp Phe Thr Leu Thr Ile Ser Arg Leu Glu
65                  70                  75                  80 cct gaa gat ttt gca gtg tat tat tgt cag cag tat gga agt tca cct       288
Pro Glu Asp Phe Ala Val Tyr Tyr Cys Gln Gln Tyr Gly Ser Ser Pro
                85                  90                  95 ccg tgg atg ttc ggc caa ggg acc aag gtg gag atc aaa                   327
Pro Trp Met Phe Gly Gln Gly Thr Lys Val Glu Ile Lys
                100                 105

<210> SEQ ID NO 14
<211> LENGTH: 109
<212> TYPE: PRT
<213> ORGANISM: Artificial
<220> FEATURE:
<223> OTHER INFORMATION: Synthetic Construct

<400> SEQUENCE: 14

Asp Ile Val Leu Thr Gln Thr Pro Ala Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Arg Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Trp Met Phe Gly Gln Gly Thr Lys Val Glu Ile Lys
                100                 105
```

<210> SEQ ID NO 15
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 15

```
gag gtt cag ctg gtg cag tct ggg gga ggc ttg gta cat cct ggg ggg      48
Glu Val Gln Leu Val Gln Ser Gly Gly Gly Leu Val His Pro Gly Gly
1               5                   10                  15 tcc ctg aga ctc tcc tgt gca ggc tct gga ttc acc ttc agt aga aat      96
Ser Leu Arg Leu Ser Cys Ala Gly Ser Gly Phe Thr Phe Ser Arg Asn
            20                  25                  30 gct atg ttc tgg gtt cgc cag gct cca gga aaa ggt ctg gag tgg gta     144
Ala Met Phe Trp Val Arg Gln Ala Pro Gly Lys Gly Leu Glu Trp Val
        35                  40                  45 tca ggt att ggt act ggt ggt gcc aca aac tat gca gac tcc gtg aag     192
Ser Gly Ile Gly Thr Gly Gly Ala Thr Asn Tyr Ala Asp Ser Val Lys
    50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
65                  70                  75                  80 caa atg aac agc ctg aga gcc gag gac atg gct gtg tat tac tgt gca     288
Gln Met Asn Ser Leu Arg Ala Glu Asp Met Ala Val Tyr Tyr Cys Ala
                85                  90                  95 aga ggg agg tac tac ttt gac tac tgg ggc cag gga acc ctg gtc acc     336
Arg Gly Arg Tyr Tyr Phe Asp Tyr Trp Gly Gln Gly Thr Leu Val Thr
            100                 105                 110 gtc tcc tca                                                         345
Val Ser Ser
        115
```

<210> SEQ ID NO 16
<211> LENGTH: 115
<212> TYPE: PRT
<213> ORGANISM: Artificial
<220> FEATURE:
<223> OTHER INFORMATION: Synthetic Construct

<400> SEQUENCE: 16

```
Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Asp Tyr Trp Gly Gln Gly Thr Leu Val Thr
            100                 105                 110

Val Ser Ser
        115
```

<210> SEQ ID NO 17
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 17

```
gag gtt cag ctg gtg cag tct ggg gga ggc ttg gta cat cct ggg ggg    48
Glu Val Gln Leu Val Gln Ser Gly Gly Gly Leu Val His Pro Gly Gly
1               5                   10                  15 tcc ctg aga ctc tcc tgt gca ggc tct gga ttc acc ttc agt aga aat    96
Ser Leu Arg Leu Ser Cys Ala Gly Ser Gly Phe Thr Phe Ser Arg Asn
            20                  25                  30 gct atg ttc tgg gtt cgc cag gct cca gga aaa ggt ctg gag tgg gta   144
Ala Met Phe Trp Val Arg Gln Ala Pro Gly Lys Gly Leu Glu Trp Val
        35                  40                  45 tca ggt att ggt act ggt ggt gcc aca agc tat gca gac tcc gtg aag   192
Ser Gly Ile Gly Thr Gly Gly Ala Thr Ser Tyr Ala Asp Ser Val Lys
    50                  55                  60 ggc cga ttc acc atc tcc aga gac aat gcc aag aac tcc ttg tat ctt   240
Gly Arg Phe Thr Ile Ser Arg Asp Asn Ala Lys Asn Ser Leu Tyr Leu
65                  70                  75                  80 caa atg aac agc ctg agt gcc gag gac atg gct gtg tat tac tgt gca   288
Gln Met Asn Ser Leu Ser Ala Glu Asp Met Ala Val Tyr Tyr Cys Ala
                85                  90                  95 aga ggg agg tac tac ttc acc cac tgg ggc cag gga acc ctg gtc acc   336
Arg Gly Arg Tyr Tyr Phe Thr His Trp Gly Gln Gly Thr Leu Val Thr
            100                 105                 110 gtc tcc tca                                                       345
Val Ser Ser
        115
```

<210> SEQ ID NO 18
<211> LENGTH: 115
<212> TYPE: PRT
<213> ORGANISM: Artificial
<220> FEATURE:
<223> OTHER INFORMATION: Synthetic Construct

<400> SEQUENCE: 18

```
Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Ser Ala Glu Asp Met Ala Val Tyr Tyr Cys Ala
                85                  90                  95

Arg Gly Arg Tyr Tyr Phe Thr His Trp Gly Gln Gly Thr Leu Val Thr
            100                 105                 110

Val Ser Ser
        115
```

<210> SEQ ID NO 19
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 19

```
gag gtt cag ctg gtg cag tct ggg gga ggc ttg gta cat cct ggg ggg      48
Glu Val Gln Leu Val Gln Ser Gly Gly Gly Leu Val His Pro Gly Gly
1               5                   10                  15 tcc ctg aga ctc tcc tgt gca ggc tct gga ttc acc ttc agt aga aat      96
Ser Leu Arg Leu Ser Cys Ala Gly Ser Gly Phe Thr Phe Ser Arg Asn
            20                  25                  30 gct atg ttc tgg gtt cgc cag gct cca gga aaa ggt ctg gag tgg gta     144
Ala Met Phe Trp Val Arg Gln Ala Pro Gly Lys Gly Leu Glu Trp Val
        35                  40                  45 tca ggt att ggt act ggt ggt gcc aca agc tat gca gac tcc gtg aag     192
Ser Gly Ile Gly Thr Gly Gly Ala Thr Ser Tyr Ala Asp Ser Val Lys
    50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
65                  70                  75                  80 caa atg aac agc ctg aga gcc gag gac atg gct gtg tat tac tgt gca     288
Gln Met Asn Ser Leu Arg Ala Glu Asp Met Ala Val Tyr Tyr Cys Ala
                85                  90                  95 aga ggg agg tac tgg tac aac aac tgg ggc cag gga acc ctg gtc acc     336
Arg Gly Arg Tyr Trp Tyr Asn Asn Trp Gly Gln Gly Thr Leu Val Thr
            100                 105                 110 gtc tcc tca                                                         345
Val Ser Ser
        115
```

<210> SEQ ID NO 20
<211> LENGTH: 115
<212> TYPE: PRT
<213> ORGANISM: Artificial
<220> FEATURE:
<223> OTHER INFORMATION: Synthetic Construct

<400> SEQUENCE: 20

```
Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Trp Tyr Asn Asn Trp Gly Gln Gly Thr Leu Val Thr
            100                 105                 110

Val Ser Ser
        115
```

-continued

<210> SEQ ID NO 21
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 21

```
gag gtt cag ttg gtg cag tct ggg gga ggc ttg gta cat cct ggg ggg      48
Glu Val Gln Leu Val Gln Ser Gly Gly Gly Leu Val His Pro Gly Gly
1               5                   10                  15 tcc ctg aga ctc tcc tgt gca ggc tct gga ttc acc ttc agt aga aat      96
Ser Leu Arg Leu Ser Cys Ala Gly Ser Gly Phe Thr Phe Ser Arg Asn
            20                  25                  30 gct atg ttc tgg gtt cgc cag gct cca gga aaa ggt ctg gag tgg gta     144
Ala Met Phe Trp Val Arg Gln Ala Pro Gly Lys Gly Leu Glu Trp Val
        35                  40                  45 tca ggt att ggt act ggt ggt gcc aca aac tat gca gac tcc gtg aag     192
Ser Gly Ile Gly Thr Gly Gly Ala Thr Asn Tyr Ala Asp Ser Val Lys
    50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
65                  70                  75                  80 caa atg aac agc ctg aga gcc gag gac atg gct gtg tat tac tgt gca     288
Gln Met Asn Ser Leu Arg Ala Glu Asp Met Ala Val Tyr Tyr Cys Ala
                85                  90                  95 aga ggg agg tac tac ttc ccg tgg tgg ggc cag gga acc ctg gtc acc     336
Arg Gly Arg Tyr Tyr Phe Pro Trp Trp Gly Gln Gly Thr Leu Val Thr
            100                 105                 110 gtc tcc tca                                                         345
Val Ser Ser
        115
```

<210> SEQ ID NO 22
<211> LENGTH: 115
<212> TYPE: PRT
<213> ORGANISM: Artificial
<220> FEATURE:
<223> OTHER INFORMATION: Synthetic Construct

<400> SEQUENCE: 22

```
Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Pro Trp Trp Gly Gln Gly Thr Leu Val Thr
            100                 105                 110

Val Ser Ser
        115
```

<210> SEQ ID NO 23
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 23

```
gag gtt cag ctg gtg cag tct ggg gga ggc ttg gta cat cct ggg ggg    48
Glu Val Gln Leu Val Gln Ser Gly Gly Gly Leu Val His Pro Gly Gly
1               5                   10                  15 tcc ctg aga ctc tcc tgt gca ggc tct gga ttc acc ttc agt aga aat    96
Ser Leu Arg Leu Ser Cys Ala Gly Ser Gly Phe Thr Phe Ser Arg Asn
            20                  25                  30 gct atg ttc tgg gtt cgc cag gct cca gga aaa ggt ctg gag tgg gta   144
Ala Met Phe Trp Val Arg Gln Ala Pro Gly Lys Gly Leu Glu Trp Val
        35                  40                  45 tca ggt att ggt act ggt ggt gcc aca aac tat gca gac tcc gtg aag   192
Ser Gly Ile Gly Thr Gly Gly Ala Thr Asn Tyr Ala Asp Ser Val Lys
    50                  55                  60 ggc cga ttc acc atc tcc aga gac aat gcc aag aac tcc ttg tat ctt   240
Gly Arg Phe Thr Ile Ser Arg Asp Asn Ala Lys Asn Ser Leu Tyr Leu
65                  70                  75                  80 caa atg aac agc ctg aga gcc gag gac atg gct gtg tat tac tgt gca   288
Gln Met Asn Ser Leu Arg Ala Glu Asp Met Ala Val Tyr Tyr Cys Ala
                85                  90                  95 aga ggg agg tac tac ttc acg agg tgg ggc cag gga acc ctg gtc acc   336
Arg Gly Arg Tyr Tyr Phe Thr Arg Trp Gly Gln Gly Thr Leu Val Thr
            100                 105                 110 gtc tcc tca                                                       345
Val Ser Ser
        115
```

<210> SEQ ID NO 24
<211> LENGTH: 115
<212> TYPE: PRT
<213> ORGANISM: Artificial
<220> FEATURE:
<223> OTHER INFORMATION: Synthetic Construct

<400> SEQUENCE: 24

```
Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Thr Arg Trp Gly Gln Gly Thr Leu Val Thr
            100                 105                 110

Val Ser Ser
        115
```

<210> SEQ ID NO 25
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 25

```
gag gtt cag ttg gtg cag tct ggg gga ggc ttg gta cat cct ggg ggg         48
Glu Val Gln Leu Val Gln Ser Gly Gly Gly Leu Val His Pro Gly Gly
1               5                   10                  15 tcc ctg aga ctc tcc tgt gca ggc tct gga ttc acc ttc agt aga aat         96
Ser Leu Arg Leu Ser Cys Ala Gly Ser Gly Phe Thr Phe Ser Arg Asn
            20                  25                  30 gct atg ttc tgg gtt cgc cag gct cca gga aaa ggt ctg gag tgg gta        144
Ala Met Phe Trp Val Arg Gln Ala Pro Gly Lys Gly Leu Glu Trp Val
        35                  40                  45 tca ggt att ggt act ggt ggt gcc aca aac tat gca gac tcc gtg aag        192
Ser Gly Ile Gly Thr Gly Gly Ala Thr Asn Tyr Ala Asp Ser Val Lys
    50                  55                  60 ggc cga ttc acc atc tcc aga gac aat gcc aag aac tcc ttg tat ctt        240
Gly Arg Phe Thr Ile Ser Arg Asp Asn Ala Lys Asn Ser Leu Tyr Leu
65                  70                  75                  80 caa atg aac agc ctg aga gcc gag gac atg gct gtg tat tac tgt gca        288
Gln Met Asn Ser Leu Arg Ala Glu Asp Met Ala Val Tyr Tyr Cys Ala
                85                  90                  95 aga ggg agg tac tgg tac ccg tgg tgg ggc cag gga acc ctg gtc acc        336
Arg Gly Arg Tyr Trp Tyr Pro Trp Trp Gly Gln Gly Thr Leu Val Thr
            100                 105                 110 gtc tcc tca                                                            345
Val Ser Ser
        115
```

<210> SEQ ID NO 26
<211> LENGTH: 115
<212> TYPE: PRT
<213> ORGANISM: Artificial
<220> FEATURE:
<223> OTHER INFORMATION: Synthetic Construct

<400> SEQUENCE: 26

```
Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Trp Tyr Pro Trp Trp Gly Gln Gly Thr Leu Val Thr
            100                 105                 110

Val Ser Ser
        115
```

<210> SEQ ID NO 27
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 27

```
gag gtt cag ctg gtg cag tct ggg gga ggc ttg gta cat cct ggg ggg      48
Glu Val Gln Leu Val Gln Ser Gly Gly Gly Leu Val His Pro Gly Gly
1               5                   10                  15 tcc ctg aga ctc tcc tgt gca ggc tct gga ttc acc ttc agt aga aat      96
Ser Leu Arg Leu Ser Cys Ala Gly Ser Gly Phe Thr Phe Ser Arg Asn
            20                  25                  30 gct atg ttc tgg gtt cgc cag gct cca gga aaa ggt ctg gag tgg gta     144
Ala Met Phe Trp Val Arg Gln Ala Pro Gly Lys Gly Leu Glu Trp Val
        35                  40                  45 tca ggt att ggt act ggt ggt gcc aca agc tat gca gac tcc gtg aag     192
Ser Gly Ile Gly Thr Gly Gly Ala Thr Ser Tyr Ala Asp Ser Val Lys
    50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
65                  70                  75                  80 caa atg aac agc ctg aga gcc gag gac atg gct gtg tat tac tgt gca     288
Gln Met Asn Ser Leu Arg Ala Glu Asp Met Ala Val Tyr Tyr Cys Ala
                85                  90                  95 aga ggg agg tac tgg tac ccg tgg tgg ggc cag gga acc ctg gtc acc     336
Arg Gly Arg Tyr Trp Tyr Pro Trp Trp Gly Gln Gly Thr Leu Val Thr
            100                 105                 110 gtc tcc tca                                                         345
Val Ser Ser
        115
```

<210> SEQ ID NO 28
<211> LENGTH: 115
<212> TYPE: PRT
<213> ORGANISM: Artificial
<220> FEATURE:
<223> OTHER INFORMATION: Synthetic Construct

<400> SEQUENCE: 28

```
Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Trp Tyr Pro Trp Trp Gly Gln Gly Thr Leu Val Thr
            100                 105                 110

Val Ser Ser
        115
```

<210> SEQ ID NO 29
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 29

| gag | gtt | cag | ttg | gtg | cag | tct | ggg | gga | ggc | ttg | gta | cat | cct | ggg | ggg | 48 |
| Glu | Val | Gln | Leu | Val | Gln | Ser | Gly | Gly | Gly | Leu | Val | His | Pro | Gly | Gly | |
| 1 | | | | 5 | | | | | 10 | | | | | 15 | | |

| tcc | ctg | aga | ctc | tcc | tgt | gca | ggc | tct | gga | ttc | acc | ttc | agt | aga | aat | 96 |
| Ser | Leu | Arg | Leu | Ser | Cys | Ala | Gly | Ser | Gly | Phe | Thr | Phe | Ser | Arg | Asn | |
| | | | 20 | | | | | 25 | | | | | 30 | | | |

| gct | atg | ttc | tgg | gtt | cgc | cag | gct | cca | gga | aaa | ggt | ctg | gag | tgg | gta | 144 |
| Ala | Met | Phe | Trp | Val | Arg | Gln | Ala | Pro | Gly | Lys | Gly | Leu | Glu | Trp | Val | |
| | | 35 | | | | | 40 | | | | | 45 | | | | |

| tca | ggt | att | ggt | act | ggt | ggt | gcc | aca | aac | tat | gca | gac | tcc | gtg | aag | 192 |
| Ser | Gly | Ile | Gly | Thr | Gly | Gly | Ala | Thr | Asn | Tyr | Ala | Asp | Ser | Val | Lys | |
| 50 | | | | | 55 | | | | | 60 | | | | | | |

| ggc | cga | ttc | acc | atc | tcc | aga | gac | aat | gcc | aag | aac | tcc | ttg | tat | ctt | 240 |
| Gly | Arg | Phe | Thr | Ile | Ser | Arg | Asp | Asn | Ala | Lys | Asn | Ser | Leu | Tyr | Leu | |
| 65 | | | | 70 | | | | | 75 | | | | | 80 | | |

| caa | atg | aac | agc | ctg | aga | gcc | gag | gac | atg | gct | gtg | tat | tac | tgt | gca | 288 |
| Gln | Met | Asn | Ser | Leu | Arg | Ala | Glu | Asp | Met | Ala | Val | Tyr | Tyr | Cys | Ala | |
| | | | 85 | | | | | 90 | | | | | 95 | | | |

| aga | ggg | agg | tac | tgg | ttc | ccg | tgg | tgg | ggc | cag | gga | acc | ctg | gtc | acc | 336 |
| Arg | Gly | Arg | Tyr | Trp | Phe | Pro | Trp | Trp | Gly | Gln | Gly | Thr | Leu | Val | Thr | |
| | | 100 | | | | | 105 | | | | | 110 | | | | |

| gtc | tcc | tca | | | | | | | | | | | | | | 345 |
| Val | Ser | Ser | | | | | | | | | | | | | | |
| | | 115 | | | | | | | | | | | | | | |

<210> SEQ ID NO 30
<211> LENGTH: 115
<212> TYPE: PRT
<213> ORGANISM: Artificial
<220> FEATURE:
<223> OTHER INFORMATION: Synthetic Construct

<400> SEQUENCE: 30

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
            85                  90                  95

Arg Gly Arg Tyr Trp Phe Pro Trp Trp Gly Gln Gly Thr Leu Val Thr
        100                 105                 110

Val Ser Ser
    115

-continued

<210> SEQ ID NO 31
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 31

```
gag gtt cag ctg gtg cag tct ggg gga ggc ttg gta cat cct ggg ggg      48
Glu Val Gln Leu Val Gln Ser Gly Gly Gly Leu Val His Pro Gly Gly
1               5                   10                  15 tcc ctg aga ctc tcc tgt gca ggc tct gga ttc acc ttc agt aga aat      96
Ser Leu Arg Leu Ser Cys Ala Gly Ser Gly Phe Thr Phe Ser Arg Asn
            20                  25                  30 gct atg ttc tgg gtt cgc cag gct cca gga aaa ggt ctg gag tgg gta     144
Ala Met Phe Trp Val Arg Gln Ala Pro Gly Lys Gly Leu Glu Trp Val
        35                  40                  45 tca ggt att ggt act ggt ggt gcc aca agc tat gca gac tcc gtg aag     192
Ser Gly Ile Gly Thr Gly Gly Ala Thr Ser Tyr Ala Asp Ser Val Lys
    50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
65                  70                  75                  80 caa atg aac agc ctg aga gcc gag gac atg gct gtg tat tac tgt gca     288
Gln Met Asn Ser Leu Arg Ala Glu Asp Met Ala Val Tyr Tyr Cys Ala
                85                  90                  95 aga ggg agg tac tgg ttc ccg tgg tgg ggc cag gga acc ctg gtc acc     336
Arg Gly Arg Tyr Trp Phe Pro Trp Trp Gly Gln Gly Thr Leu Val Thr
            100                 105                 110 gtc tcc tca                                                         345
Val Ser Ser
        115
```

<210> SEQ ID NO 32
<211> LENGTH: 115
<212> TYPE: PRT
<213> ORGANISM: Artificial
<220> FEATURE:
<223> OTHER INFORMATION: Synthetic Construct

<400> SEQUENCE: 32

```
Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Trp Phe Pro Trp Trp Gly Gln Gly Thr Leu Val Thr
            100                 105                 110

Val Ser Ser
        115
```

<210> SEQ ID NO 33
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 33

```
gag gtt cag ttg gtg cag tct ggg gga ggc ttg gta cat cct ggg ggg      48
Glu Val Gln Leu Val Gln Ser Gly Gly Gly Leu Val His Pro Gly Gly
1               5                   10                  15 tcc ctg aga ctc tcc tgt gca ggc tct gga ttc acc ttc agt aga aat      96
Ser Leu Arg Leu Ser Cys Ala Gly Ser Gly Phe Thr Phe Ser Arg Asn
                20                  25                  30 gct atg ttc tgg gtt cgc cag gct cca gga aaa ggt ctg gag tgg gta     144
Ala Met Phe Trp Val Arg Gln Ala Pro Gly Lys Gly Leu Glu Trp Val
            35                  40                  45 tca ggt att ggt act ggt ggt gcc aca aac tat gca gac tcc gtg aag     192
Ser Gly Ile Gly Thr Gly Gly Ala Thr Asn Tyr Ala Asp Ser Val Lys
        50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
65                  70                  75                  80 caa atg aac agc ctg aga gcc gag gac atg gct gtg tat tac tgt gca     288
Gln Met Asn Ser Leu Arg Ala Glu Asp Met Ala Val Tyr Tyr Cys Ala
                85                  90                  95 aga ggg agg tac tgg tac ccg tgg tgg ggc cag gga acc ctg gtc acc     336
Arg Gly Arg Tyr Trp Tyr Pro Trp Trp Gly Gln Gly Thr Leu Val Thr
            100                 105                 110 gtc tcc tca                                                          345
Val Ser Ser
        115
```

<210> SEQ ID NO 34
<211> LENGTH: 115
<212> TYPE: PRT
<213> ORGANISM: Artificial
<220> FEATURE:
<223> OTHER INFORMATION: Synthetic Construct

<400> SEQUENCE: 34

```
Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
                20                  25                  30

Ala Met Phe Trp Val Arg Gln Ala Pro Gly Lys Gly Leu Glu Trp Val
            35                  40                  45

Ser Gly Ile Gly Thr Gly Gly Ala Thr Asn Tyr Ala Asp Ser Val Lys
        50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Trp Tyr Pro Trp Trp Gly Gln Gly Thr Leu Val Thr
            100                 105                 110

Val Ser Ser
        115
```

<210> SEQ ID NO 35
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 35

```
gag gtt cag ctg gtg cag tct ggg gga ggc ttg gta cat cct ggg ggg      48
Glu Val Gln Leu Val Gln Ser Gly Gly Gly Leu Val His Pro Gly Gly
 1               5                  10                  15 tcc ctg aga ctc tcc tgt gca ggc tct gga ttc acc ttc agt aga aat      96
Ser Leu Arg Leu Ser Cys Ala Gly Ser Gly Phe Thr Phe Ser Arg Asn
             20                  25                  30 gct atg ttc tgg gtt cgc cag gct cca gga aaa ggt ctg gag tgg gta     144
Ala Met Phe Trp Val Arg Gln Ala Pro Gly Lys Gly Leu Glu Trp Val
         35                  40                  45 tca ggt att ggt act ggt ggt gcc aca agc tat gca gac tcc gtg aag     192
Ser Gly Ile Gly Thr Gly Gly Ala Thr Ser Tyr Ala Asp Ser Val Lys
     50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
 65                  70                  75                  80 caa atg aac agc ctg aga gcc gag gac atg gct gtg tat tac tgt gca     288
Gln Met Asn Ser Leu Arg Ala Glu Asp Met Ala Val Tyr Tyr Cys Ala
                 85                  90                  95 aga ggg agg tac tgg tac ccg tgg tgg ggc cag gga acc ctg gtc acc     336
Arg Gly Arg Tyr Trp Tyr Pro Trp Trp Gly Gln Gly Thr Leu Val Thr
            100                 105                 110 gtc tcc tca                                                         345
Val Ser Ser
        115
```

<210> SEQ ID NO 36
<211> LENGTH: 115
<212> TYPE: PRT
<213> ORGANISM: Artificial
<220> FEATURE:
<223> OTHER INFORMATION: Synthetic Construct

<400> SEQUENCE: 36

```
Glu Val Gln Leu Val Gln Ser Gly Gly Gly Leu Val His Pro Gly Gly
 1               5                  10                  15

Ser Leu Arg Leu Ser Cys Ala Gly Ser Gly Phe Thr Phe Ser Arg Asn
             20                  25                  30

Ala Met Phe Trp Val Arg Gln Ala Pro Gly Lys Gly Leu Glu Trp Val
         35                  40                  45

Ser Gly Ile Gly Thr Gly Gly Ala Thr Ser Tyr Ala Asp Ser Val Lys
     50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Met Ala Val Tyr Tyr Cys Ala
                 85                  90                  95

Arg Gly Arg Tyr Trp Tyr Pro Trp Trp Gly Gln Gly Thr Leu Val Thr
            100                 105                 110

Val Ser Ser
        115
```

<210> SEQ ID NO 37
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 37

```
gag gtt cag ctg gtg cag tct ggg gga ggc ttg gta cat cct ggg ggg      48
Glu Val Gln Leu Val Gln Ser Gly Gly Gly Leu Val His Pro Gly Gly
1               5                   10                  15 tcc ctg aga ctc tcc tgt gca ggc tct gga ttc acc ttc agt aga aat      96
Ser Leu Arg Leu Ser Cys Ala Gly Ser Gly Phe Thr Phe Ser Arg Asn
            20                  25                  30 gct atg ttc tgg gtt cgc cag gct cca gga aaa ggt ctg gag tgg gta     144
Ala Met Phe Trp Val Arg Gln Ala Pro Gly Lys Gly Leu Glu Trp Val
        35                  40                  45 tca ggt att ggt act ggt ggt gcc aca agc tat gca gac tcc gtg aag     192
Ser Gly Ile Gly Thr Gly Gly Ala Thr Ser Tyr Ala Asp Ser Val Lys
    50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
65                  70                  75                  80 caa atg aac agc ctg aga gcc gag gac atg gct gtg tat tac tgt gca     288
Gln Met Asn Ser Leu Arg Ala Glu Asp Met Ala Val Tyr Tyr Cys Ala
                85                  90                  95 aga ggg agg tac tac ttc ccg tgg tgg ggc cag gga acc ctg gtc acc     336
Arg Gly Arg Tyr Tyr Phe Pro Trp Trp Gly Gln Gly Thr Leu Val Thr
            100                 105                 110 gtc tcc tca                                                         345
Val Ser Ser
        115
```

<210> SEQ ID NO 38
<211> LENGTH: 115
<212> TYPE: PRT
<213> ORGANISM: Artificial
<220> FEATURE:
<223> OTHER INFORMATION: Synthetic Construct

<400> SEQUENCE: 38

```
Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Gly Arg Tyr Tyr Phe Pro Trp Trp Gly Gln Gly Thr Leu Val Thr
            100                 105                 110

Val Ser Ser
        115
```

<210> SEQ ID NO 39
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 39

```
gag gtt cag ctg gtg cag tct ggg gga ggc ttg gta cat cct ggg ggg    48
Glu Val Gln Leu Val Gln Ser Gly Gly Gly Leu Val His Pro Gly Gly
1               5                   10                  15 tcc ctg aga ctc tcc tgt gca ggc tct gga ttc acc ttc agt aga aat    96
Ser Leu Arg Leu Ser Cys Ala Gly Ser Gly Phe Thr Phe Ser Arg Asn
            20                  25                  30 gct atg ttc tgg gtt cgc cag gct cca gga aaa ggt ctg gag tgg gta   144
Ala Met Phe Trp Val Arg Gln Ala Pro Gly Lys Gly Leu Glu Trp Val
        35                  40                  45 tca ggt att ggt act ggt ggt gcc aca agc tat gca gac tcc gtg aag   192
Ser Gly Ile Gly Thr Gly Gly Ala Thr Ser Tyr Ala Asp Ser Val Lys
    50                  55                  60 ggc cga ttc acc atc tcc aga gac aat gcc aag aac tcc ttg tat ctt   240
Gly Arg Phe Thr Ile Ser Arg Asp Asn Ala Lys Asn Ser Leu Tyr Leu
65                  70                  75                  80 caa atg aac agc ctg agt gcc gag gac atg gct gtg tat tac tgt gca   288
Gln Met Asn Ser Leu Ser Ala Glu Asp Met Ala Val Tyr Tyr Cys Ala
                85                  90                  95 aga ggg agg tac tac ttc ccg tgg tgg ggc cag gga acc ctg gtc acc   336
Arg Gly Arg Tyr Tyr Phe Pro Trp Trp Gly Gln Gly Thr Leu Val Thr
            100                 105                 110 gtc tcc tca                                                       345
Val Ser Ser
        115
```

<210> SEQ ID NO 40
<211> LENGTH: 115
<212> TYPE: PRT
<213> ORGANISM: Artificial
<220> FEATURE:
<223> OTHER INFORMATION: Synthetic Construct

<400> SEQUENCE: 40

```
Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Ser Ala Glu Asp Met Ala Val Tyr Tyr Cys Ala
                85                  90                  95

Arg Gly Arg Tyr Tyr Phe Pro Trp Trp Gly Gln Gly Thr Leu Val Thr
            100                 105                 110

Val Ser Ser
        115
```

<210> SEQ ID NO 41
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 41

```
gag gtt cag ttg gtg gag tct ggg gga ggc ttg gta cag cct ggg ggg      48
Glu Val Gln Leu Val Glu Ser Gly Gly Gly Leu Val Gln Pro Gly Gly
1               5                  10                  15 tcc ctg aga ctc tcc tgt gca gcc tct gga ttc acc ttc agt aga aat      96
Ser Leu Arg Leu Ser Cys Ala Ala Ser Gly Phe Thr Phe Ser Arg Asn
            20                  25                  30 gct atg ttc tgg gtt cgc cag gct cca gga aaa ggt ctg gag tgg gta     144
Ala Met Phe Trp Val Arg Gln Ala Pro Gly Lys Gly Leu Glu Trp Val
        35                  40                  45 tca ggt att ggt act ggt ggt gcc aca agc tat gca gac tcc gtg aag     192
Ser Gly Ile Gly Thr Gly Gly Ala Thr Ser Tyr Ala Asp Ser Val Lys
    50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
65                  70                  75                  80 caa atg aac agc ctg aga gcc gag gac acg gct gtg tat tac tgt gca     288
Gln Met Asn Ser Leu Arg Ala Glu Asp Thr Ala Val Tyr Tyr Cys Ala
                85                  90                  95 aga ggg agg tac tac ttc ccg tgg tgg ggc cag gga acc ctg gtc acc     336
Arg Gly Arg Tyr Tyr Phe Pro Trp Trp Gly Gln Gly Thr Leu Val Thr
            100                 105                 110 gtc tcc tca                                                          345
Val Ser Ser
        115
```

<210> SEQ ID NO 42
<211> LENGTH: 115
<212> TYPE: PRT
<213> ORGANISM: Artificial
<220> FEATURE:
<223> OTHER INFORMATION: Synthetic Construct

<400> SEQUENCE: 42

```
Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Tyr Phe Pro Trp Trp Gly Gln Gly Thr Leu Val Thr
            100                 105                 110

Val Ser Ser
        115
```

<210> SEQ ID NO 43
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 43

```
gag gtt cag ttg gtg gag tct ggg gga ggc ttg gta cag cct ggg ggg        48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttc agt aga aat        96
Ser Leu Arg Leu Ser Cys Ala Ala Ser Gly Phe Thr Phe Ser Arg Asn
            20                  25                  30 gct atg ttc tgg gtt cgc cag gct cca gga aaa ggt ctg gag tgg gta       144
Ala Met Phe Trp Val Arg Gln Ala Pro Gly Lys Gly Leu Glu Trp Val
        35                  40                  45 tca ggt att ggt act ggt ggt gcc aca agc tat gca gac tcc gtg aag       192
Ser Gly Ile Gly Thr Gly Gly Ala Thr Ser Tyr Ala Asp Ser Val Lys
    50                  55                  60 ggc cga ttc acc atc tcc aga gac aat gcc aag aac tcc ttg tat ctt       240
Gly Arg Phe Thr Ile Ser Arg Asp Asn Ala Lys Asn Ser Leu Tyr Leu
65                  70                  75                  80 caa atg aac agc ctg aga gcc gag gac acg gct gtg tat tac tgt gca       288
Gln Met Asn Ser Leu Arg Ala Glu Asp Thr Ala Val Tyr Tyr Cys Ala
                85                  90                  95 aga ggg agg tac tac ttt gac tac tgg ggc cag gga acc ctg gtc acc       336
Arg Gly Arg Tyr Tyr Phe Asp Tyr Trp Gly Gln Gly Thr Leu Val Thr
            100                 105                 110 gtc tcc tca                                                           345
Val Ser Ser
        115
```

<210> SEQ ID NO 44
<211> LENGTH: 115
<212> TYPE: PRT
<213> ORGANISM: Artificial
<220> FEATURE:
<223> OTHER INFORMATION: Synthetic Construct

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Tyr Phe Asp Tyr Trp Gly Gln Gly Thr Leu Val Thr
            100                 105                 110

Val Ser Ser
        115

<210> SEQ ID NO 45
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 45

| gag | gtt | cag | ttg | gtg | gag | tct | ggg | gga | ggc | ttg | gta | cag | cct | ggg | ggg | 48 |
|---|---|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly | |
| 1 | | | | 5 | | | | | 10 | | | | | 15 | | |

| tcc | ctg | aga | ctc | tcc | tgt | gca | gcc | tct | gga | ttc | acc | ttc | agt | aga | aat | 96 |
|---|---|---|---|---|---|---|---|---|---|---|---|---|---|---|---|---|
| Ser | Leu | Arg | Leu | Ser | Cys | Ala | Ala | Ser | Gly | Phe | Thr | Phe | Ser | Arg | Asn | |
| | | | 20 | | | | | 25 | | | | | 30 | | | |

| gct | atg | ttc | tgg | gtt | cgc | cag | gct | cca | gga | aaa | ggt | ctg | gag | tgg | gta | 144 |
|---|---|---|---|---|---|---|---|---|---|---|---|---|---|---|---|---|
| Ala | Met | Phe | Trp | Val | Arg | Gln | Ala | Pro | Gly | Lys | Gly | Leu | Glu | Trp | Val | |
| | | 35 | | | | | 40 | | | | | 45 | | | | |

| tca | ggt | att | ggt | act | ggt | ggt | gcc | aca | agc | tat | gca | gac | tcc | gtg | aag | 192 |
|---|---|---|---|---|---|---|---|---|---|---|---|---|---|---|---|---|
| Ser | Gly | Ile | Gly | Thr | Gly | Gly | Ala | Thr | Ser | Tyr | Ala | Asp | Ser | Val | Lys | |
| 50 | | | | | 55 | | | | | 60 | | | | | | |

| ggc | cga | ttc | acc | atc | tcc | aga | gac | aat | gcc | aag | aac | tcc | ttg | tat | ctt | 240 |
|---|---|---|---|---|---|---|---|---|---|---|---|---|---|---|---|---|
| Gly | Arg | Phe | Thr | Ile | Ser | Arg | Asp | Asn | Ala | Lys | Asn | Ser | Leu | Tyr | Leu | |
| 65 | | | | | 70 | | | | | 75 | | | | | 80 | |

| caa | atg | aac | agc | ctg | aga | gcc | gag | gac | acg | gct | gtg | tat | tac | tgt | gca | 288 |
|---|---|---|---|---|---|---|---|---|---|---|---|---|---|---|---|---|
| Gln | Met | Asn | Ser | Leu | Arg | Ala | Glu | Asp | Thr | Ala | Val | Tyr | Tyr | Cys | Ala | |
| | | | | 85 | | | | | 90 | | | | | 95 | | |

| aga | ggg | agg | tac | tac | ttc | acc | cac | tgg | ggc | cag | gga | acc | ctg | gtc | acc | 336 |
|---|---|---|---|---|---|---|---|---|---|---|---|---|---|---|---|---|
| Arg | Gly | Arg | Tyr | Tyr | Phe | Thr | His | Trp | Gly | Gln | Gly | Thr | Leu | Val | Thr | |
| | | | 100 | | | | | 105 | | | | | 110 | | | |

| gtc | tcc | tca | | | | | | | | | | | | | | 345 |
|---|---|---|---|---|---|---|---|---|---|---|---|---|---|---|---|---|
| Val | Ser | Ser | | | | | | | | | | | | | | |
| | | 115 | | | | | | | | | | | | | | |

<210> SEQ ID NO 46
<211> LENGTH: 115
<212> TYPE: PRT
<213> ORGANISM: Artificial
<220> FEATURE:
<223> OTHER INFORMATION: Synthetic Construct

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Tyr Phe Thr His Trp Gly Gln Gly Thr Leu Val Thr
            100                 105                 110

Val Ser Ser
        115

```
<210> SEQ ID NO 47
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 47 gag gtt cag ttg gtg gag tct ggg gga ggc ttg gta cag cct ggg ggg       48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttc agt aga aat       96
Ser Leu Arg Leu Ser Cys Ala Ala Ser Gly Phe Thr Phe Ser Arg Asn
            20                  25                  30 gct atg ttc tgg gtt cgc cag gct cca gga aaa ggt ctg gag tgg gta      144
Ala Met Phe Trp Val Arg Gln Ala Pro Gly Lys Gly Leu Glu Trp Val
        35                  40                  45 tca ggt att ggt act ggt ggt gcc aca agc tat gca gac tcc gtg aag      192
Ser Gly Ile Gly Thr Gly Gly Ala Thr Ser Tyr Ala Asp Ser Val Lys
    50                  55                  60 ggc cga ttc acc atc tcc aga gac aat gcc aag aac tcc ttg tat ctt      240
Gly Arg Phe Thr Ile Ser Arg Asp Asn Ala Lys Asn Ser Leu Tyr Leu
65                  70                  75                  80 caa atg aac agc ctg aga gcc gag gac acg gct gtg tat tac tgt gca      288
Gln Met Asn Ser Leu Arg Ala Glu Asp Thr Ala Val Tyr Tyr Cys Ala
                85                  90                  95 aga ggg agg tac tgg tac aac aac tgg ggc cag gga acc ctg gtc acc      336
Arg Gly Arg Tyr Trp Tyr Asn Asn Trp Gly Gln Gly Thr Leu Val Thr
            100                 105                 110 gtc tcc tca                                                          345
Val Ser Ser
        115

<210> SEQ ID NO 48
<211> LENGTH: 115
<212> TYPE: PRT
<213> ORGANISM: Artificial
<220> FEATURE:
<223> OTHER INFORMATION: Synthetic Construct

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Trp Tyr Asn Asn Trp Gly Gln Gly Thr Leu Val Thr
            100                 105                 110

Val Ser Ser
        115
```

```
<210> SEQ ID NO 49
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 49 gag gtt cag ttg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttc agt aga aat      96
Ser Leu Arg Leu Ser Cys Ala Ala Ser Gly Phe Thr Phe Ser Arg Asn
            20                  25                  30 gct atg ttc tgg gtt cgc cag gct cca gga aaa ggt ctg gag tgg gta     144
Ala Met Phe Trp Val Arg Gln Ala Pro Gly Lys Gly Leu Glu Trp Val
        35                  40                  45 tca ggt att ggt act ggt ggt gcc aca agc tat gca gac tcc gtg aag     192
Ser Gly Ile Gly Thr Gly Gly Ala Thr Ser Tyr Ala Asp Ser Val Lys
    50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
65                  70                  75                  80 caa atg aac agc ctg aga gcc gag gac acg gct gtg tat tac tgt gca     288
Gln Met Asn Ser Leu Arg Ala Glu Asp Thr Ala Val Tyr Tyr Cys Ala
                85                  90                  95 aga ggg agg tac tac ttc acg agg tgg ggc cag gga acc ctg gtc acc     336
Arg Gly Arg Tyr Tyr Phe Thr Arg Trp Gly Gln Gly Thr Leu Val Thr
            100                 105                 110 gtc tcc tca                                                         345
Val Ser Ser
        115

<210> SEQ ID NO 50
<211> LENGTH: 115
<212> TYPE: PRT
<213> ORGANISM: Artificial
<220> FEATURE:
<223> OTHER INFORMATION: Synthetic Construct

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Tyr Phe Thr Arg Trp Gly Gln Gly Thr Leu Val Thr
            100                 105                 110

Val Ser Ser
        115
```

-continued

<210> SEQ ID NO 51
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 51

```
gag gtt cag ttg gtg gag tct ggg gga ggc ttg gta cag cct ggg ggg        48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttc agt aga aat        96
Ser Leu Arg Leu Ser Cys Ala Ala Ser Gly Phe Thr Phe Ser Arg Asn
            20                  25                  30 gct atg ttc tgg gtt cgc cag gct cca gga aaa ggt ctg gag tgg gta       144
Ala Met Phe Trp Val Arg Gln Ala Pro Gly Lys Gly Leu Glu Trp Val
        35                  40                  45 tca ggt att ggt act ggt ggt gcc aca agc tat gca gac tcc gtg aag       192
Ser Gly Ile Gly Thr Gly Gly Ala Thr Ser Tyr Ala Asp Ser Val Lys
    50                  55                  60 ggc cga ttc acc atc tcc aga gac aat gcc aag aac tcc ttg tat ctt       240
Gly Arg Phe Thr Ile Ser Arg Asp Asn Ala Lys Asn Ser Leu Tyr Leu
65                  70                  75                  80 caa atg aac agc ctg aga gcc gag gac acg gct gtg tat tac tgt gca       288
Gln Met Asn Ser Leu Arg Ala Glu Asp Thr Ala Val Tyr Tyr Cys Ala
                85                  90                  95 aga ggg agg tac tgg tac ccg tgg tgg ggc cag gga acc ctg gtc acc       336
Arg Gly Arg Tyr Trp Tyr Pro Trp Trp Gly Gln Gly Thr Leu Val Thr
            100                 105                 110 gtc tcc tca                                                           345
Val Ser Ser
        115
```

<210> SEQ ID NO 52
<211> LENGTH: 115
<212> TYPE: PRT
<213> ORGANISM: Artificial
<220> FEATURE:
<223> OTHER INFORMATION: Synthetic Construct

<400> SEQUENCE: 52

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Trp Tyr Pro Trp Trp Gly Gln Gly Thr Leu Val Thr
            100                 105                 110

Val Ser Ser
        115
```

<210> SEQ ID NO 53
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 53

```
gag gtt cag ttg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttc agt aga aat      96
Ser Leu Arg Leu Ser Cys Ala Ala Ser Gly Phe Thr Phe Ser Arg Asn
            20                  25                  30 gct atg ttc tgg gtt cgc cag gct cca gga aaa ggt ctg gag tgg gta     144
Ala Met Phe Trp Val Arg Gln Ala Pro Gly Lys Gly Leu Glu Trp Val
        35                  40                  45 tca ggt att ggt act ggt ggt gcc aca aac tat gca gac tcc gtg aag     192
Ser Gly Ile Gly Thr Gly Gly Ala Thr Asn Tyr Ala Asp Ser Val Lys
    50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
65                  70                  75                  80 caa atg aac agc ctg aga gcc gag gac acg gct gtg tat tac tgt gca     288
Gln Met Asn Ser Leu Arg Ala Glu Asp Thr Ala Val Tyr Tyr Cys Ala
                85                  90                  95 aga ggg agg tac tgg tac ccg tgg tgg ggc cag gga acc ctg gtc acc     336
Arg Gly Arg Tyr Trp Tyr Pro Trp Trp Gly Gln Gly Thr Leu Val Thr
            100                 105                 110 gtc tcc tca                                                          345
Val Ser Ser
        115
```

<210> SEQ ID NO 54
<211> LENGTH: 115
<212> TYPE: PRT
<213> ORGANISM: Artificial
<220> FEATURE:
<223> OTHER INFORMATION: Synthetic Construct

<400> SEQUENCE: 54

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Trp Tyr Pro Trp Trp Gly Gln Gly Thr Leu Val Thr
            100                 105                 110

Val Ser Ser
        115
```

-continued

<210> SEQ ID NO 55
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 55

```
gag gtt cag ttg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttc agt aga aat      96
Ser Leu Arg Leu Ser Cys Ala Ala Ser Gly Phe Thr Phe Ser Arg Asn
            20                  25                  30 gct atg ttc tgg gtt cgc cag gct cca gga aaa ggt ctg gag tgg gta     144
Ala Met Phe Trp Val Arg Gln Ala Pro Gly Lys Gly Leu Glu Trp Val
        35                  40                  45 tca ggt att ggt act ggt ggt gcc aca agc tat gca gac tcc gtg aag     192
Ser Gly Ile Gly Thr Gly Gly Ala Thr Ser Tyr Ala Asp Ser Val Lys
    50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
65                  70                  75                  80 caa atg aac agc ctg aga gcc gag gac acg gct gtg tat tac tgt gca     288
Gln Met Asn Ser Leu Arg Ala Glu Asp Thr Ala Val Tyr Tyr Cys Ala
                85                  90                  95 aga ggg agg tac tgg ttc ccg tgg tgg ggc cag gga acc ctg gtc acc     336
Arg Gly Arg Tyr Trp Phe Pro Trp Trp Gly Gln Gly Thr Leu Val Thr
            100                 105                 110 gtc tcc tca                                                         345
Val Ser Ser
        115
```

<210> SEQ ID NO 56
<211> LENGTH: 115
<212> TYPE: PRT
<213> ORGANISM: Artificial
<220> FEATURE:
<223> OTHER INFORMATION: Synthetic Construct

<400> SEQUENCE: 56

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Trp Phe Pro Trp Trp Gly Gln Gly Thr Leu Val Thr
            100                 105                 110

Val Ser Ser
        115
```

<210> SEQ ID NO 57
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 57

```
gag gtt cag ttg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttc agt aga aat      96
Ser Leu Arg Leu Ser Cys Ala Ala Ser Gly Phe Thr Phe Ser Arg Asn
            20                  25                  30 gct atg ttc tgg gtt cgc cag gct cca gga aaa ggt ctg gag tgg gta     144
Ala Met Phe Trp Val Arg Gln Ala Pro Gly Lys Gly Leu Glu Trp Val
        35                  40                  45 tca ggt att ggt act ggt ggt gcc aca aac tat gca gac tcc gtg aag     192
Ser Gly Ile Gly Thr Gly Gly Ala Thr Asn Tyr Ala Asp Ser Val Lys
    50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
65                  70                  75                  80 caa atg aac agc ctg aga gcc gag gac acg gct gtg tat tac tgt gca     288
Gln Met Asn Ser Leu Arg Ala Glu Asp Thr Ala Val Tyr Tyr Cys Ala
                85                  90                  95 aga ggg agg tac tgg ttc ccg tgg tgg ggc cag gga acc ctg gtc acc     336
Arg Gly Arg Tyr Trp Phe Pro Trp Trp Gly Gln Gly Thr Leu Val Thr
            100                 105                 110 gtc tcc tca                                                         345
Val Ser Ser
        115
```

<210> SEQ ID NO 58
<211> LENGTH: 115
<212> TYPE: PRT
<213> ORGANISM: Artificial
<220> FEATURE:
<223> OTHER INFORMATION: Synthetic Construct

<400> SEQUENCE: 58

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Trp Phe Pro Trp Trp Gly Gln Gly Thr Leu Val Thr
            100                 105                 110

Val Ser Ser
        115
```

```
<210> SEQ ID NO 59
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 59 gag gtt cag ttg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttc agt aga aat      96
Ser Leu Arg Leu Ser Cys Ala Ala Ser Gly Phe Thr Phe Ser Arg Asn
            20                  25                  30 gct atg ttc tgg gtt cgc cag gct cca gga aaa ggt ctg gag tgg gta     144
Ala Met Phe Trp Val Arg Gln Ala Pro Gly Lys Gly Leu Glu Trp Val
        35                  40                  45 tca ggt att ggt act ggt ggt gcc aca agc tat gca gac tcc gtg aag     192
Ser Gly Ile Gly Thr Gly Gly Ala Thr Ser Tyr Ala Asp Ser Val Lys
    50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
65                  70                  75                  80 caa atg aac agc ctg aga gcc gag gac acg gct gtg tat tac tgt gca     288
Gln Met Asn Ser Leu Arg Ala Glu Asp Thr Ala Val Tyr Tyr Cys Ala
                85                  90                  95 aga ggg agg tac tgg tac ccg tgg tgg ggc cag gga acc ctg gtc acc     336
Arg Gly Arg Tyr Trp Tyr Pro Trp Trp Gly Gln Gly Thr Leu Val Thr
            100                 105                 110 gtc tcc tca                                                         345
Val Ser Ser
        115

<210> SEQ ID NO 60
<211> LENGTH: 115
<212> TYPE: PRT
<213> ORGANISM: Artificial
<220> FEATURE:
<223> OTHER INFORMATION: Synthetic Construct

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Ser Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Trp Tyr Pro Trp Trp Gly Gln Gly Thr Leu Val Thr
            100                 105                 110

Val Ser Ser
        115
```

<210> SEQ ID NO 61
<211> LENGTH: 345
<212> TYPE: DNA
<213> ORGANISM: Artificial
<220> FEATURE:
<223> OTHER INFORMATION: Heavy chain variable sequence
<220> FEATURE:
<221> NAME/KEY: CDS
<222> LOCATION: (1)..(345)

<400> SEQUENCE: 61

```
gag gtt cag ttg gtg gag tct ggg gga ggc ttg gta cag cct ggg ggg      48
Glu Val Gln Leu Val Glu Ser Gly Gly Gly Leu Val Gln Pro Gly Gly
1               5                   10                  15 tcc ctg aga ctc tcc tgt gca gcc tct gga ttc acc ttc agt aga aat      96
Ser Leu Arg Leu Ser Cys Ala Ala Ser Gly Phe Thr Phe Ser Arg Asn
            20                  25                  30 gct atg ttc tgg gtt cgc cag gct cca gga aaa ggt ctg gag tgg gta     144
Ala Met Phe Trp Val Arg Gln Ala Pro Gly Lys Gly Leu Glu Trp Val
        35                  40                  45 tca ggt att ggt act ggt ggt gcc aca aac tat gca gac tcc gtg aag     192
Ser Gly Ile Gly Thr Gly Gly Ala Thr Asn Tyr Ala Asp Ser Val Lys
    50                  55                  60 ggc cga ttc acc atc tcc aga gac aat gcc aag aac tcc ttg tat ctt     240
Gly Arg Phe Thr Ile Ser Arg Asp Asn Ala Lys Asn Ser Leu Tyr Leu
65                  70                  75                  80 caa atg aac agc ctg aga gcc gag gac acg gct gtg tat tac tgt gca     288
Gln Met Asn Ser Leu Arg Ala Glu Asp Thr Ala Val Tyr Tyr Cys Ala
                85                  90                  95 aga ggg agg tac tgg tac ccg tgg tgg ggc cag gga acc ctg gtc acc     336
Arg Gly Arg Tyr Trp Tyr Pro Trp Trp Gly Gln Gly Thr Leu Val Thr
            100                 105                 110 gtc tcc tca                                                         345
Val Ser Ser
        115
```

<210> SEQ ID NO 62
<211> LENGTH: 115
<212> TYPE: PRT
<213> ORGANISM: Artificial
<220> FEATURE:
<223> OTHER INFORMATION: Synthetic Construct

<400> SEQUENCE: 62

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Ala Met Phe Trp Val Arg Gln Ala Pro Gly Lys Gly Leu Glu Trp Val
        35                  40                  45

Ser Gly Ile Gly Thr Gly Gly Ala Thr Asn Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Arg Tyr Trp Tyr Pro Trp Trp Gly Gln Gly Thr Leu Val Thr
            100                 105                 110

Val Ser Ser
        115
```

<210> SEQ ID NO 63
<211> LENGTH: 109
<212> TYPE: PRT
<213> ORGANISM: Artificial
<220> FEATURE:
<223> OTHER INFORMATION: 27A1 light chain variable region

<400> SEQUENCE: 63

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Trp Thr Phe Gly Gln Gly Thr Lys Val Glu Ile Lys
            100                 105

<210> SEQ ID NO 64
<211> LENGTH: 116
<212> TYPE: PRT
<213> ORGANISM: Artificial
<220> FEATURE:
<223> OTHER INFORMATION: 27A1 heavy chain variable region

<400> SEQUENCE: 64

Gln Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Arg Tyr
            20                  25                  30

Gly Met His Trp Val Arg Gln Ala Pro Gly Arg Gly Leu Glu Trp Val
        35                  40                  45

Ala Ile Ile Trp Phe Glu Gly Asn Asn Gln Tyr Tyr Ala Asp Ser Val
    50                  55                  60

Lys Gly Arg Phe Thr Val Ser Arg Asp Asn Ser Lys Asn Thr Leu Tyr
65                  70                  75                  80

Leu Glu Met Asn Ser Leu Arg Ala Glu Asp Thr Ala Val Tyr Tyr Cys
                85                  90                  95

Ala Arg Gly Lys Tyr Tyr Phe Asp Tyr Trp Gly Gln Gly Thr Leu Val
            100                 105                 110

Thr Val Ser Ser
        115

<210> SEQ ID NO 65
<211> LENGTH: 107
<212> TYPE: PRT
<213> ORGANISM: Artificial
<220> FEATURE:
<223> OTHER INFORMATION: 5A1 light chain variable region

<400> SEQUENCE: 65

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr His Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 66
<211> LENGTH: 123
<212> TYPE: PRT
<213> ORGANISM: Artificial
<220> FEATURE:
<223> OTHER INFORMATION: 5A1 heavy chain variable region

<400> SEQUENCE: 66

Glu Val Gln Leu Val Gln Ser Gly Gly Gly Leu Val His Pro Gly Gly
1               5                   10                  15

Ser Leu Arg Leu Thr Cys Ala Gly Ser Gly Phe Thr Phe Ser Asn Phe
            20                  25                  30

Val Met His Trp Val Arg Gln Thr Pro Gly Gln Gly Leu Glu Trp Val
        35                  40                  45

Ser Ala Ile Gly Thr Gly Gly Thr Tyr Tyr Ala Asp Ser Val Lys
    50                  55                  60

Gly Arg Phe Thr Ile Ser Arg Asp Asn Ala Lys Ser Ser Leu Tyr Leu
65                  70                  75                  80

Gln Met Asn Ser Leu Arg Ala Glu Asp Met Ala Val Tyr Tyr Cys Ala
                85                  90                  95

Arg Asp Arg Pro Met Val Arg Gly Val Ile Ile Asp Tyr Phe Asp Tyr
            100                 105                 110

Trp Gly Gln Gly Thr Leu Val Thr Val Ser Ser
        115                 120

<210> SEQ ID NO 67
<211> LENGTH: 107
<212> TYPE: PRT
<213> ORGANISM: Artificial
<220> FEATURE:
<223> OTHER INFORMATION: 63 light chain variable region

<400> SEQUENCE: 67

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Thr Trp
            20                  25                  30

Leu Ala Trp Tyr Gln His Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105

<210> SEQ ID NO 68
<211> LENGTH: 117
<212> TYPE: PRT
<213> ORGANISM: Artificial
<220> FEATURE:
<223> OTHER INFORMATION: 63 heavy chain variable region

<400> SEQUENCE: 68

Glu Val Gln Val Leu Glu Ser Gly Gly Asn Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Thr Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Phe Tyr Cys
                85                  90                  95

Ala Lys Asp Asn Arg Gly Phe Phe His Tyr Trp Gly Gln Gly Thr Leu
            100                 105                 110

Val Thr Val Ser Ser
        115

<210> SEQ ID NO 69
<211> LENGTH: 107
<212> TYPE: PRT
<213> ORGANISM: Artificial
<220> FEATURE:
<223> OTHER INFORMATION: 1B7 light chain variable region

<400> SEQUENCE: 69

Glu Ile Val Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Arg
            20                  25                  30

Leu Ala Trp Tyr Gln Gln Lys Pro Gly Lys Ala Pro Lys Leu Leu Ile
        35                  40                  45

Tyr Ile Ala Ser Ile Leu Gln Arg Gly Val Pro Ser Arg Phe Ser Gly
    50                  55                  60

Ser Gly Ser Gly Thr Asp Phe Thr Leu Thr Ile Thr Arg Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105

<210> SEQ ID NO 70
<211> LENGTH: 36
<212> TYPE: DNA
<213> ORGANISM: Artificial
<220> FEATURE:
<223> OTHER INFORMATION: Primers
<220> FEATURE:
<221> NAME/KEY: misc_feature
<222> LOCATION: (21)..(21)

```
<223> OTHER INFORMATION: N is A or G
<220> FEATURE:
<221> NAME/KEY: misc_feature
<222> LOCATION: (24)..(24)
<223> OTHER INFORMATION: N is G or T

<400> SEQUENCE: 70
gtcgacgccg ccaccatgga nttngggctg agctgg                           36

<210> SEQ ID NO 71
<211> LENGTH: 21
<212> TYPE: DNA
<213> ORGANISM: Artificial
<220> FEATURE:
<223> OTHER INFORMATION: Primers

<400> SEQUENCE: 71
cttgaccagg cagcccaggg c                                           21

<210> SEQ ID NO 72
<211> LENGTH: 36
<212> TYPE: DNA
<213> ORGANISM: Artificial
<220> FEATURE:
<223> OTHER INFORMATION: Primers

<400> SEQUENCE: 72
atcaaacgta cggtggctgc accatctgtc ttcatc                           36

<210> SEQ ID NO 73
<211> LENGTH: 49
<212> TYPE: DNA
<213> ORGANISM: Artificial
<220> FEATURE:
<223> OTHER INFORMATION: Primers

<400> SEQUENCE: 73
gtttaaacgc ggccgcggat cctaacactc tcccctgttg aagctcttt             49

<210> SEQ ID NO 74
<211> LENGTH: 99
<212> TYPE: DNA
<213> ORGANISM: Artificial
<220> FEATURE:
<223> OTHER INFORMATION: Primers

<400> SEQUENCE: 74
gtcgacgccg ccaccatgga acccagcg cagcttctct tcctcctgct actctggctc   60
ccagataccg ctagcgaaat tgtgttgacg cagtctcca                        99

<210> SEQ ID NO 75
<211> LENGTH: 99
<212> TYPE: DNA
<213> ORGANISM: Artificial
<220> FEATURE:
<223> OTHER INFORMATION: Primers

<400> SEQUENCE: 75
tggagactgc gtcaacacaa tttcgctagc ggtatctggg agccagagta gcaggaggaa 60
gagaagctgc gctggggttt ccatggtggc ggcgtcgac                        99

<210> SEQ ID NO 76
<211> LENGTH: 57
<212> TYPE: DNA
<213> ORGANISM: Artificial
```

```
<220> FEATURE:
<223> OTHER INFORMATION: Primers

<400> SEQUENCE: 76
atggggtcaa ccgccatcct tggcctcctc ctggctgttc tccaaggagt cgctagc       57

<210> SEQ ID NO 77
<211> LENGTH: 327
<212> TYPE: PRT
<213> ORGANISM: Homo sapiens

<400> SEQUENCE: 77
```

| | | | | | | | | | | | | | | |
|---|---|---|---|---|---|---|---|---|---|---|---|---|---|---|
| Ala | Ser | Thr | Lys | Gly | Pro | Ser | Val | Phe | Pro | Leu | Ala | Pro | Cys | Ser | Arg |
| 1 | | | | 5 | | | | | 10 | | | | | 15 | |

| Ser | Thr | Ser | Glu | Ser | Thr | Ala | Ala | Leu | Gly | Cys | Leu | Val | Lys | Asp | Tyr |
|---|---|---|---|---|---|---|---|---|---|---|---|---|---|---|---|
| | | | 20 | | | | | 25 | | | | | 30 | | |

| Phe | Pro | Glu | Pro | Val | Thr | Val | Ser | Trp | Asn | Ser | Gly | Ala | Leu | Thr | Ser |
| | | 35 | | | | | 40 | | | | | 45 | | | |

| Gly | Val | His | Thr | Phe | Pro | Ala | Val | Leu | Gln | Ser | Ser | Gly | Leu | Tyr | Ser |
| 50 | | | | | 55 | | | | | 60 | | | | | |

| Leu | Ser | Ser | Val | Val | Thr | Val | Pro | Ser | Ser | Ser | Leu | Gly | Thr | Lys | Thr |
| 65 | | | | | 70 | | | | | 75 | | | | | 80 |

| Tyr | Thr | Cys | Asn | Val | Asp | His | Lys | Pro | Ser | Asn | Thr | Lys | Val | Asp | Lys |
| | | | | 85 | | | | | 90 | | | | | 95 | |

| Arg | Val | Glu | Ser | Lys | Tyr | Gly | Pro | Pro | Cys | Pro | Ser | Cys | Pro | Ala | Pro |
| | | | 100 | | | | | 105 | | | | | 110 | | |

| Glu | Phe | Leu | Gly | Gly | Pro | Ser | Val | Phe | Leu | Phe | Pro | Pro | Lys | Pro | Lys |
| | | 115 | | | | | 120 | | | | | 125 | | | |

| Asp | Thr | Leu | Met | Ile | Ser | Arg | Thr | Pro | Glu | Val | Thr | Cys | Val | Val | Val |
| 130 | | | | | 135 | | | | | 140 | | | | | |

| Asp | Val | Ser | Gln | Glu | Asp | Pro | Glu | Val | Gln | Phe | Asn | Trp | Tyr | Val | Asp |
| 145 | | | | | 150 | | | | | 155 | | | | | 160 |

| Gly | Val | Glu | Val | His | Asn | Ala | Lys | Thr | Lys | Pro | Arg | Glu | Glu | Gln | Phe |
| | | | | 165 | | | | | 170 | | | | | 175 | |

| Asn | Ser | Thr | Tyr | Arg | Val | Val | Ser | Val | Leu | Thr | Val | Leu | His | Gln | Asp |
| | | | 180 | | | | | 185 | | | | | 190 | | |

| Trp | Leu | Asn | Gly | Lys | Glu | Tyr | Lys | Cys | Lys | Val | Ser | Asn | Lys | Gly | Leu |
| | | 195 | | | | | 200 | | | | | 205 | | | |

| Pro | Ser | Ser | Ile | Glu | Lys | Thr | Ile | Ser | Lys | Ala | Lys | Gly | Gln | Pro | Arg |
| 210 | | | | | 215 | | | | | 220 | | | | | |

| Glu | Pro | Gln | Val | Tyr | Thr | Leu | Pro | Pro | Ser | Gln | Glu | Glu | Met | Thr | Lys |
| 225 | | | | | 230 | | | | | 235 | | | | | 240 |

| Asn | Gln | Val | Ser | Leu | Thr | Cys | Leu | Val | Lys | Gly | Phe | Tyr | Pro | Ser | Asp |
| | | | | 245 | | | | | 250 | | | | | 255 | |

| Ile | Ala | Val | Glu | Trp | Glu | Ser | Asn | Gly | Gln | Pro | Glu | Asn | Asn | Tyr | Lys |
| | | | 260 | | | | | 265 | | | | | 270 | | |

| Thr | Thr | Pro | Pro | Val | Leu | Asp | Ser | Asp | Gly | Ser | Phe | Phe | Leu | Tyr | Ser |
| | | 275 | | | | | 280 | | | | | 285 | | | |

| Arg | Leu | Thr | Val | Asp | Lys | Ser | Arg | Trp | Gln | Glu | Gly | Asn | Val | Phe | Ser |
| 290 | | | | | 295 | | | | | 300 | | | | | |

| Cys | Ser | Val | Met | His | Glu | Ala | Leu | His | Asn | His | Tyr | Thr | Gln | Lys | Ser |
| 305 | | | | | 310 | | | | | 315 | | | | | 320 |

| Leu | Ser | Leu | Ser | Leu | Gly | Lys |
| | | | 325 | | | |